(12) United States Patent
Spiegelman et al.

(10) Patent No.: US 7,354,738 B2
(45) Date of Patent: Apr. 8, 2008

(54) PGC-1β, A NOVEL PGC-1 HOMOLOGUE AND USES THEREFOR

(75) Inventors: Bruce M. Spiegelman, Waban, MA (US); Jiandie Lin, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 11/413,066

(22) Filed: Apr. 27, 2006

(65) Prior Publication Data
US 2007/0009933 A1 Jan. 11, 2007

Related U.S. Application Data

(62) Division of application No. 10/290,544, filed on Nov. 8, 2002, now Pat. No. 7,091,006.

(60) Provisional application No. 60/338,126, filed on Nov. 9, 2001.

(51) Int. Cl.
*C12P 21/06* (2006.01)
(52) U.S. Cl. ............... 435/69.1; 536/23.1; 530/350
(58) Field of Classification Search ............... 435/69.1, 435/252.3, 320.1; 536/23.1; 530/300, 350
See application file for complete search history.

(56) References Cited

FOREIGN PATENT DOCUMENTS

WO WO 02/18424 9/2000
WO WO 02/22818 3/2002

OTHER PUBLICATIONS

Accession No. AAD36095.
Accession No. AAE22761.
Aranda et al., "Nuclear hormone receptors and gene expression," Physiol. Rev. 81(3): 1269-1304 (2001).
Andersson et al., "PGC-1-related coactivator, a novel, serum-inducible coactivator of nuclear respiratory factory 1-dependent transcription in mammalian cells," Mol. Cell. Biol., 21:3728-3749 (2001).
Freedman, L.P., "Increasing the complexity of coactivation in nuclear receptor signaling," Cell, 97:5-8 (1999).
Frieman et al., "Viral mimicry: common mode of association with HCF by VP16 and the cellular protein LZIP," Genes Dev., 11:3122-3127 (1997).
Georgiev, et al., "Two versatile eukaryotic vectors permitting epitope tagging, radiolabelling and nuclear localisation of expressed proteins," Gene, 168: 165-167 (1996).
Herzig et al., "CREB regulates hepatic gluconegenesis through the coactivator PGC-1," Nature, 413:179-183 (2001).
Klaus et al., "Characterization of the novel brown adipocyte cell line HIB 1B. Adrenergic pathways involved in regulation of uncoupling protein gene expression," J. Cell. Sci., 107:313-319 (1994).
Kersten et al., "Peroxisome proliferator-activated receptor α mediates the adaptive response to fasting," J. Clin. Invest., 103:1489-1498 (1999).
Kristie et al., "Nuclear localization of the C1 factor (host cell factor) in sensory neurons correlates with reactivation of herpes simplex virus from latency," Proc. Natl. Acad. Sci. U.S.A., 96:1229-1233 (1999).
Lehman et al., "Peroxisome proliferator-activated receptor γcoactivator-1 promotes cardiac mitochondrial biogenesis," J. Clin. Invest., 106:847-856 (2000).
Michael et al., "Restoration of insulin-sensitive glucose transporter (GLUT4) gene expression in muscle cells by the transcriptional coactivator PGC-1," Proc. Natl. Acad. Sci., U.S.A. 98:3820-3825 (2001).
Monsalve et al., "Direct coupling of transcription and mRNA processing through the thermogenic coactivator PGC-1," Mol. Cell, 6:307-316 (2000).
Nolte et al., "Ligand binding and co-activator assembly of the peroxisome proliferator-activated receptor-γ," Nature, 395:137-143 (1998).
Puigserver et al., "A cold-inducible coactivator of nuclear receptors linked to adaptive thermogenesis," Cell, 92:829-839 (1998).
Rosenfeld et al., "Coregulator codes of transcriptional regulation by nuclear receptors," J. Biol. Chem., 276(40):36865-36868 (2001).
Vega et al., "The coactivator PGC-1 cooperates with peroxisome proliferator-activated receptor α in transcriptional control of nuclear genes encoding mitochondrial fatty acid oxidation enzymes," Mol. Cell. Biol., 20(5):1868-1876 (2000).
Vogel et al., "The novel coactivator C1 (HCF) coordinates multiprotein enhancer formation and mediates transcription activation by GABP," EMBO J., 19:683-690 (2000).
Westin et al., "Interactions controlling the assembly of nuclear-receptor heterodimers and coactivators," Nature, 395: 199-202 (1998).
Wilson et al., "The VP16 accessory protein HCF is a family of polypeptides processed from a large precursor protein," Cell, 74:115-125 (1993).
Wilson et al., "The VP16 targets an amino-terminal domain of HCF involved in cell cycle progression," Mol. Cell. Biol., 17:6139-6146 (1997).
Wu et al, "Mechanisms controlling mitochondrial biogenesis and respiration through the thermogenic coactivator PGC-1," Cell, 98:115-124 (1999).
Yoon et al., "Control of hepatic gluconeogenesis through the transcriptional coactivator PGC-1," Nature, 413:131-138 (2001).
International Search Report, dated Jan. 7, 2005.

*Primary Examiner*—Tekchand Saidha
(74) *Attorney, Agent, or Firm*—Foley Hoag LLP

(57) ABSTRACT

The invention provides isolated nucleic acid molecules, designated PGC-1β nucleic acid molecules, which encode novel PGC-1 related coactivator molecules. The invention also provides antisense nucleic acid molecules, recombinant expression vectors containing PGC-1β nucleic acid molecules, host cells into which the expression vectors have been introduced, and nonhuman transgenic animals in which a PGC-1β gene has been introduced or disrupted. The invention still further provides isolated PGC-1β proteins, fusion proteins, antigenic peptides and anti-PGC-1β antibodies. Diagnostic and therapeutic methods utilizing compositions of the invention are also provided.

5 Claims, 14 Drawing Sheets

```
CTCGCTCCCTCCCCGGGCGGGCCTCGGCCTGACTCGGCCCACGCTGCAGCCGGCGCTGGAAGATGGCGGGGAACGACT         80
GCGGCCGCGCTGCTGGATGAAGAGCTCTCGTCCTTCTTCCTCAACTATCTCTCTTGACACGCAGGGTGGGGACTCTGGAGAG
GAACAGCTGTGTGCTGACTTGCCAGAGCTTGACCTCTCCAGCTGACACGCCAGTGACTTTGACTCAGCCACGTGCTTTGG
GGAGCTGCAGTGGTGCCGGAGACCTCAGAGACAGAGCCCAGCGCAGTGACCCCGATGACTGAGCCTCTTCCAGATTG
ACAGTGAGAATGAAGCTCTCTTGGCTGCCGTTACGAAGAGCCCCAGCACCCTGGATGACATCCCGAAGATGTGGGGCTGGCTGCC         400
TTCCAGAACTGGATGAAGGCGACACACCATGCTGACCAGCCCTCACCTGCCCCTTATCTGCACCCCCAGCCCAC
CCTGGAGAGGCTTCTCTGCTCCCAGCGTCTGACGTGGACGAGCTTTCACTGCTACAGAAGCTCCTCTGGCCACATCCTCC
CAACAGCAAGCTCTGACGCTCTGAAGGACGGGCCGCAGGATCTCAGGACCAGCCTCAGTTCCAGAAGTCAGCGGCCTTGT
GTCAAGGTGGATGGCACCAGGATAAGAAGACCCCCAGCTGCTCCCAAACTCACTGCGAGACCAGCCTCAGTGCTCATAAGCA
AGGAGGAGGAGGTGGGGGAGGATTGCCAAGCCCTTGGCCTGGACTCCAGCCCCCCGAGCCCTCGGCCTCCTCCAAAG
CCTCACTTCGGTGCTGCCCCTGTCCCAGAGTGAAAGCTCGCTCCCAAACTCAGCGCACCCCGAGCCCTCCGCTCCTAGCA
ACGGCCAGCCCGACAGTGCCCAGCCTCCCGAGGATGTAGCTTCGCTACAGCTCATTCGCTACAGGAC
CTGCCTCCTCAGAGAAGCTGCCCCAACGGGCCCCAGAGGCCTGACAGCTCATTCGCTACAGCTCATTCCTA
AACCCCGATCCCCGGCATCCCCCAAAGCCTTCTGGACTGAGTTCTCTATCCCCTAAGGAACTTCTGCCCAAGATATCCTC
TGTGATGTTAGCAAGCCCTACCGCCTGCCATACCTGTCTATGCTTCCCTCACACTGTCTTCCCCAAGGCCCCAAGGCCCAA         1200
GGACAGTCAGGCCTCCCCTGCCACTCTGCCAATGGCAGAAGAGGTGAAGAATCACTCCTAAGGAATCACTGAAGGCCTA
GACCCAGCCTGCGTCCTGAGGCTGGAGAAGAAGCGGATGTTAACAAGCTACAAGGCAGTGGCAGAAGCGGGAAGATGAG
GAGGAGGAAGAAGAAGAAGAAGAAGAAGAAGAAGAAGAGAAGCTACAAGCAAAGCGGGAGGAAGATGAG
TGCCTGCCATGACAAACTAGGAGGAAGATGAGCAGCTCCGTTGCTCCGGTGCCCACTGAAGGAACTTTCCCAAGATGTCG         1600
AGCTGGGTCCTCCTGCCTGACAATTCACTGATGAGCCCTTAGGTGCTCTGCCCTGATGTGCTGGATACAGAGACCACAC
CTGAGGAAGACCTGGGCAGCCTCACAGAGACAGTAGTCAAGGCGGCAGCTCGGGGATCCCAGGATCCCGCCCCTGGA
AAGCCCTGTGAGAGTGGGTGCCGGAGACACAGATGAAGATCCAAGCTGCCACACCTTCCAGAGACTCCTCCAGGT
GCCTCATGCTGGCCTTGTCACAAGCGACTCTCTTGGCAAGAAGAGCTTTGAGGAGTCCCTGACGGTGGAGCTTGCGGC
ACGGCAGGACTCAGCCACCACCACCTCCATACAAGCCAATGGAGGAGGACCCCTTCAAGCCAGACACCAGCTCAG
```

FIGURE 1A

```
CCCAGGGCCAAGACACAGCTCCAGCCTTCCTCCGCTCTTCCGCTCACAGCCACCCAGGAGCCTTCCCACAAGC
TGCCAAGAGGCACCAGAGCGAAGCGAGCCTCCTGTCCCATTTGCAGCATGCCACAACCAGTCTCACAGGCTGGC
CAGAAGCGCCCCTTCTCCTTCCTTTGAGACCACTGCCAGCTGCTCAGGCCAGGCTGCCCTGCAGGAGGAA
GGTGCTGCGGTCCTGGGAGCCAATCGGGGTCCACCTTGAAGACTTGGCCCAGGTGCCCCTCTGCCAACGGAAACAA
AGGCCCTAGGAGGGAGGCAAACCAGAAACTGTGACCTACCACAAGGACAGCCATGCAGTAAGAGACCATGAGATCCGT
GCCAGTCTCACAAAGCACTTTGGGCTGCTGGAGACTGCTCTGGAAGGTGAAGACCTGGGCGTCCTGTAAAAGCCCGAGTA
TGACACCGTATTTGAGGACAGCAGCAGCACCAGTGGGCGAGAGTAGCTTCCTGCTTGAGGAGGAGAAGAAACNAGGAGG
GAGGGGAAGAGGGACGATGAAGGAGGAGGACTCAGGGGTCAGCCCTGCTCTGATCACTGCCCCTACCAGAGCCCACCC
AGTAAGGCCAGTCGGCAGTCTCGCTCCGAAGCCGCTCCAGTTCCAGCGTCCTCGTCTTCCCTGGTCACCAGCCAC
CCGGAAGAACTTCAGACGTGAGACAAGAGGCCCTGTTCAGATGGAACCCCAAGCGTCCCGCCATGCCAAGAACGGCGGG
AAAAGGCCATCGGTGAAGCCGTGTGGTATACATTCGAAATCTCCAGTGACATGAGCTCTCGGGAACTAAAGAAGCGC
TTTGAGGTGTTCGGTGAGATTGTAGAGTGCCAGGTGCTGACGAGAAGTAAAAGAGGCCAGAAGCACGGTTTTATCACCTT
CCGGTGTTCAGAGACGCTGCCCTGTCCGTGAGGAACGGCGCCAGATAAGACCGCCCACCGCAATGAGCCCTCCTTCCACCTGA
GCTATGAGGGCTCCGGCACTTCCGTTGACAGATACACTGACTATGATCCACACATCTGACTGAGTCCCTTCCCTCATCT
GGGAAAGCAAGTACGAAGCCATGGATTTTGACAGCTTACTGAAGAGGCCCAGCAGAGCCTGCATTGATATGAGGCCTTA
ACCTTCGAGGAATACCTCAATACCTCAGACAAGCCCTTCAAATATGTTTACGTTTTCAAAGAAAAGACTATATGAGAAG
GAGAGCAGCGAGCAGCGTGAGCGTAGAGATCACACAGGAGAGAAAAGACTTGAATCTGCTGTCGTT
TCCTTTAAAAAACGAAAAAACAAATCAAATGTTACATTGAACAAAAGCTGCTTCCGTCCGTCTGTCCGT
CCGTCCGTCCGTGAGTTACCATTCTGATGTTCCACTGCCACGTTAGCGTCGTCCTCCAGCGGATCGTC
CTGGGTGCCGCCTCCAAGTGCTGTCAGTCGTCCTCTGCCCCTCCACCGACTTCCTCTGTTAGACTTGAGCTGTG
TTCACATAACATCTTCTGTCTGTAGAGTGTGATGATGACATTGTTACTTGTGAATAGAATCAGGAGTTAGAAACTTCATTT
TTAATTGAAGAAAAAAGTATATCCTTAAAAGAAAAAAAAAACAAATGTAAAAAAAA
```

FIGURE 1B

```
MAGNDCGALL  DEELSSFFLN  YLSDTQGGDS  GEEQLCADLP  ELDLSQLDAS   50
DFDSATCFGE  LQWCPETSET  EPSQYSPDDS  ELFQIDSENE  ALLAALTKTL  100
DDIPEDDVGL  AAFPELDEGD  TPSCTPASPA  PLSAPPSPTL  ERLLSPASDV  150
DELSLLQKLL  LATSSPTASS  DALKDGATWS  QTSLSSRSQR  PCVKVDGTQD  200
KKTPTLRAQS  RPCTELHKHL  TSVLPCPRVK  ACSPTPHPSP  RLLSKEEEE   250
VGEDCPSPWP  TPASPQDSLA  QDTASPDSAQ  PPEEDVRAMV  QLIRYMHTYC  300
LPQRKLPQRA  PEPIPQACSS  LSRQVQPRSR  HPPKAFWTEF  SILRELLAQD  350
ILCDVSKPYR  LAIPVYASLT  PQSRPRPPKD  SQASPAHSAM  AEEVRITASP  400
KSTGPRPSLR  PLRLEVKRDV  NKPTRQKREE  DEEEEEEEE   EEEEKEEEEE  450
EWGRKRPGRG  LPWTKLGRKM  DSSVCPVRRS  RRLNPELGPW  LTFTDEPLGA  500
LPSMCLDTET  HNLEEDLGSL  TDSSQGRQLP  QGSQIPALES  PCESGCGDTD  550
EDPSCPQPTS  RDSSRCLMLA  LSQSDSLGKK  SFEESLTVEL  CGTAGLTPPT  600
TPPYKPMEED  PFKPDTKLSP  GQDTAPSLPS  PEALPLTATP  GASHKLPKRH  650
PERSELLSHL  QHATTQPVSQ  AGQKRPFSCS  FGDHDYCQVL  RPEAALQRKV  700
IRASLTKHFG  LLETALEGED  LASCKSPEYD  TVFEDSSSSS  GESSFLIEEE  750
LRSWEPIGVH  LEDLAQGAP   LPTETKAPRR  EANQNCDPTH  KDSMQLRDHE  800
EEEEEGGEED  DEGEDSGVSP  PCSDHCPYQS  PPSKASRQLC  SRSRSSSGSS  850
SCSSWSPATR  KNFRRESRGP  CSDGTPSVRH  ARKRREKAIG  EGRVVYIRNL  900
SSDMSSRELK  KRFEVFGEIV  ECQVLTRSKR  GQKHGFITFR  CSEHAALSVR  950
NGATLRKRNE  PSFHLSYGGL  RHFRWPRYTD  YDPTSEESLP  SSGKSKYEAM 1000
DFDSLLKEAQ  QSLH
```

FIGURE 2

ATGCCTCCTGTGTATGCCTCTGAGTATGTCTTGCCACTCCAGGGTGGAGG
GTCCGGGGAGGAGCAACTCTATGCTGACTTTCCAGAACTCGACCTCTCCC
AGCTGGATGCCAGCGACTTTGACTCGGCCACCTGCTTTGGGGAGCTGCAG
TGGTGCCCAGAGAACTCAGAGACTGAACCCAACCAGTACAGCCCCGATGA
CTCCGAGCTCTTCCAGATTGACAGTGAGAATGAGGCCCTCCTGGCAGAGC
TCACCAAGACCCTGGATGACATCCCTGAAGATGACGTGGGTCTGGCTGCC
TTCCCAGCCCTGGATGGTGGAGACGCTCTATCATGCACCTCAGCTTCGCC
TGCCCCCTCATCTGCACCCCCAGCCCTGCCCGGAGAAGCCCTCGGCCC
CAGCCCCTGAGGTGGACGAGCTCTCACTGCTGCAGAAGCTCCTCCTGGCC
ACATCCTACCCAACATCAAGCTCTGACACCCAGAAGGAAGGGACCGCCTG
GCGCCAGGCAGGCCTCAGATCTAAAAGTCAACGGCCTTGTGTTAAGGCGG
ACAGCACCCAAGACAAGAAGGCTCCCATGATGCAGTCTCAGAGCCGAAGT
TGTACAGAACTACATAAGCACCTCACCTCGGCACAGTGCTGCCTGCAGGA
TCGGGGTCTGCAGCCACCATGCCTCCAGAGTCCCCGGCTCCTGCCAAGG
AGGACAAGGAGCCGGGTGAGGACTGCCCGAGCCCCAGCCAGCTCCAGCC
TCTCCCCGGGACTCCCTAGCTCTGGGCAGGGCAGACCCCGGTGCCCGGT
TTCCCAGGAAGACATGCAGGCGATGGTGCAACTCATACGCTACATGCACA
CCTACTGCCTCCCCAGAGGAAGCTGCCCCACAGACCCCTGAGCCACTC
CCCAAGGCCTGCAGCAACCCCTCCAGCAGGTCAGATCCCGGCCCTGGTC
CCGGCACCACTCCAAAGCCTCCTGGGCTGAGTTCTCCATTCTGAGGGAAC
TTCTGGCTCAAGACGTGCTCTGTGATGTCAGCAAACCCTACCGTCTGGCC
ACGCCTGTTTATGCCTCCCTCACACCTCGGTCAAGGCCCAGGCCCCCAA
AGACAGTCAGGCCTCCCCTGGTCGCCATCCTCGGTGGAGGAGGTAAGGA
TCGCAGCTTCACCCAAGAGCACCGGGCCCAGACCAAGCCTGCGCCCACTG
CGGCTGGAGGTGAAAAGGGAGGTCCGCCGGCCTGCCAGACTGCAGCAGCA
GGAGGAGGAAGACGAGGAAGAAGAGGAGGAGGAAGAGGAAGAAGAAAAG
AGGAGGAGGAGGAGTGGGGCAGGAAAGGCCAGGCCGAGGCCTGCCATGG
ACGAAGCTGGGGAGGAAGCTGGAGAGCTCTGTGCCCCGTGCGGCGTTC
TCGGAGACTGAACCCTGAGCTGGGCCCTGGCTGACATTTGCAGATGAGC
CGCTGGTCCCCTCGGAGCCCCAAGGTGCTCTGCCCTCACTGTGCCTGGCT
CCCAAGGCCTACGACGTAGAGCGGGAGCTGGGCAGCCCACGGACGAGGA

FIGURE 3A

```
CAGTGGCCAAGACCAGCAGCTCCTACGGGACCCCAGATCCCTGCCCTGG
AGAGCCCTGTGAGAGTGGCGACCCAACTTTTGGCAAGAAGAGCTTTGAG
CAGACCTTGACAGTGGAGCTCTGTGGCACAGCAGGTGAGCCAGGGGCTT
CCACTGGCAGGTGCCTTCAGGAAAACACCCGTGCATCTCTGAGTTTTCA
TCATGCATGGGCAAGGACTCACCCCACCCACCACACCACCGTACAAGCCC
ACAGAGGAGGATCCCTTCAAACCAGACATCAAGCATAGTCTAGGCAAAGA
AATAGCTCTCAGCCTCCCCTCCCTGAGGGCCTCTCACTCAAGGCCACCC
CAGGGGCTGCCCACAAGCTGCCAAAGAAGCACCCAGAGCGAAGTGAGCTC
CTGTCCCACCTGCGACATGCCACAGCCCAGCCAGCCTCCCAGGCTGGCCA
GAAGCGTCCCTTCTCCTGTTCCTTTGGAGACCATGACTACTGCCAGGTGC
TCCGACCAGAAGGCGTCCTGCAAAGGAAGGTGCTGAGGTCCTGGGAGCCG
TCTGGGGTTCACCTTGAGGACTGGCCCCAGCAGGGTGCCCCTTGGGCTGA
GGCACAGGCCCCTGGCAGGGAGGAAGACAGAAGCTGTGATGCTGGCGCCC
CACCCAAGGACAGCACGCTGCTGAGAGACCATGAGATCCGTGCCAGCCTC
ACCAAACACTTTGGGCTGCTGGAGACCGCCCTGGAGGAGGAAGACCTGGC
CTCCTGCAAGAGCCCTGAGTATGACACTGTCTTTGAAGACAGCAGCAGCA
GCAGCGGCGAGAGCAGCTTCCTCCCAGAGGAGGAAGAGGAAGAAGGGGAG
GAGGAGGAGGAGGACGATGAAGAAGAGGACTCAGGGGTCAGCCCCACTTG
CTCTGACCACTGCCCCTACCAGAGCCCACCAAGCAAGGCCAACCGGCAGC
TCTGTTCCCGCAGCCGCTCAAGCTCTGGCTCTTCACCCTGCCACTCCTGG
TCACCAGCCACTCGAAGGAACTTCAGATGTGAGAGCAGAGGGCCGTGTTC
AGACAGAACGCCAAGCATCCGGCACGCCAGGAAGCGGCGGGAAAAGGCCA
TTGGGGAAGGCCGCGTGGTGTACATTCAAATCTCTCCAGCGACATGAGC
TCCCGAGAGCTGAAGAGGCGCTTTGAAGTGTTTGGTGAGATTGAGGAGTG
CGAGGTGCTGACAAGAAATAGGAGAGGCGAGAAGTACGGCTTCATCACCT
ACCGGTGTTCTGAGCACGCGGCCCTCTCTTTGACAAAGGGCGCTGCCCTG
AGGAAGCGCAACGAGCCCTCCTTCCAGCTGAGCTACGGAGGGCTCCGGCA
CTTCTGCTGGCCCAGATACACTGACTACGATTCCAATTCAGAAGAGGCCC
TTCCTGCGTCAGGGAAAAGCAAGTATGAAGCCATGGATTTTGACAGCTTA
CTGAAAGAGGCCCAGCAGAGCCTGCAT<u>TGA</u>
```

FIGURE 3B

MPPVYASEYVLPLQGGGSGEEQLYADFPELDLSQLDASD
FDSATCFGELQWCPENSETEPNQYSPDDSELFQIDSENE
ALLAELTKTLDDIPEDDVGLAAFPALDGGDALSCTSASP
APSSAPPSPAPEKPSAPAPEVDELSLL<u>QKLLL</u>ATSYPTS
SSDTQKEGTAWRQAGLRSKSQRPCVKADSTQDKKAPMMQ
SQSRSCTELHKHLTSAQCCLQDRGLQPPCLQSPRLPAKE
DKEPGEDCPSPQPAPASPRDSLALGRADPGAPVSQEDMQ
AMVQLIRYMHTYCLPQRKLPPQTPEPLPKACSNPSQQVR
SRPWSRHHSKASWAEFSI<u>LRELL</u>AQDVLCDVSKPYRLAT
PVYASLTPRSRPRPPKDSQASPGRPSSVEEVRIAASPKS
TGPRPSLRPLRLEVKREVRRPARLQQQEEDEEEEEEE
EEEKEEEEEWGRKRPGRGLPWTKLGRKLESSVCPVRRSR
RLNPELGPWLTFADEPLVPSEPQGALPSLCLAPKAYDVE
RELGSPTDEDSGQDQQLLRGPQIPALESPCESGDPTFGK
KSFEQTLTVELCGTAGEPGGFHWQVPSGKHPCISEFFIM
HGQGLTPPTTPPYKPTEEDPFKPDIKHSLGKEIALSLPS
PEGLSLKATPGAAHKLPKKHPERSELLSHLRHATAQPAS
QAGQKRPFSCSFG[DHDY]CQVLRPEGVLQRKVLRSWEPSG
VHLEDWPQQGAPWAEQAPGREEDRSCDAGAPPKDSTLL
RDHEIRASLTKHFGLLETALEEDLASCKSPEYDTVFED
SSSSSGESSFLPEEEEEGEEEEDDEEEDSGVSPTCSD
HCPYQSPPSKANRQLCSRSRSSSGSSPCHSWSPATRRNF
RCESRGPCSDRTPSIRHARKRREKAIGEGRVVYIQNLSS
DMSSRELKRRFEVFGEIEECEVLTRNRRGEKYGFITYRC
SEHAALSLTKGAALRKRNEPSFQLSYGGLRHFCWPRYTD
YDSNSEEALPASGKSKYEAMDFDSLLKEAQQSLH

FIGURE 4

PGC-1β, A NOVEL PGC-1 HOMOLOGUE AND USES THEREFOR

RELATED APPLICATIONS

This application is a divisional application of U.S. Ser. No. 10/290,544 filed on Nov. 8, 2002, now U.S. Pat. No. 7,091,006 which claims priority to U.S. Provisional Application No. 60/338,126 filed on Nov. 9, 2001; each application is incorporated herein in its entirety by reference.

GOVERNMENT SUPPORT

Work described herein was supported under grants R37DK31405 and DK54477 awarded by the National Institutes of Health. The U.S. government may have certain rights in this invention.

BACKGROUND OF THE INVENTION

The transcriptional function of many nuclear receptors (NRs) is regulated by ligand-dependent recruitment of coactivators to the carboxyl-terminal ligand-binding domain (Aranda, A., and Pascual, A. (2001) *Physiol. Rev.* 81:1269-1304; Rosenfeld, M. G. and Glass, C. K. (2001) *J. Biol. Chem.* 276:36865-36868). A number of coactivators, including the p160 family, p300/CBP and P/CAF, contain intrinsic histone acetyl transferase activity and regulate transcription by modulating histone acetylation (Aranda and Pascual (2001) supra). Other coactivators, consisting of heterogeneous proteins with little sequence homology, modulate transcription by acting as protein docking interfaces that recruit histone acetyl transferase-containing complexes or associate with basal transcription factors such as RNA polymerase II holoenzyme (Freedman, L. P. (1999) *Cell* 97:5-8). The interaction between NRs and many coactivators requires a conserved LXXLL motif (L is leucine and X is any amino acid), which is believed to form hydrophobic contacts with the receptors (Nolte, R. T. et al. (1998) *Nature* 395:137-143; Westin, S. et al. (1998) *Nature* 395:199-202).

PGC-1 was initially identified as a PPARγ-interacting protein from a brown adipose tissue (BAT) library and was subsequently found to associate with an array of NRs and transcription factors (Puigserver, P. et al. (1998) *Cell* 92:829-839; Wu, Z. et al. (1999) *Cell* 98:115-124; Vega, R. B. et al. (2000) *Mol. Cell. Biol.* 20:1868-1876; Michael, L. F. et al. (2001) *Proc. Natl. Acad. Sci. USA* 98:3820-3825). Importantly, PGC-1 has been shown to coordinately regulate the program of mitochondrial biogenesis and adaptive thermogenesis in BAT and skeletal muscle, mainly through the coactivation of PPARs and nuclear respiratory factor 1 (NRF1), a nuclear transcription factor that regulates the expression of many mitochondrial genes (Puigserver et al. (1998) supra; Wu et al. (1999) supra). In transgenic mice, PGC-1 increases mitochondrial biogenesis and β-oxidation of fatty acids in the heart, likely through augmentation of PPARα and NRF1 transcriptional activity (Lehman, J. J. et al. (2000) *J. Clin. Invest.* 106:847-856). Recently, PGC-1 expression was found to be elevated in fasted liver and several models of type-1 and type-2 diabetes; in addition, PGC-1 can directly control the activation of hepatic gluconeogenesis (Yoon, J. C. et al. (2001) *Nature* 413:131-138; Herzig, S. et al. (2001) *Nature* 413:179-183).

SUMMARY OF THE INVENTION

The present invention is based, at least in part, on the discovery of novel members of the family of PGC-1 molecules, referred to herein as PGC-1β nucleic acid and protein molecules (e.g., human and mouse PGC-1β). The present invention is further based, at least in part, on the discovery that PGC-1β is upregulated during brown fat determination/differentiation, but not during cold exposure. The present invention is further based, at least in part, on the discovery that PGC-1β expression is upregulated in the liver during fasting. The present invention is further based, at least in part, on the discovery that PGC-1β induces mitochondrial biogenesis and fatty acid oxidation gene expression in the liver and cultured murine myotubes. The present invention is further based, at least in part, on the discovery that PGC-1β is highly expressed in brown adipose tissue (BAT) and the heart (tissues that contain high levels of mitochondria and substrate oxidation)and on the discovery that PGC-1β is a potent coactivator of NRF1. The present invention is still further based, at least in part, on the discovery that host cell factor (HCF), a cellular protein that is involved in herpes simplex virus (HSV) infection and cell cycle regulation (Wilson, A. C. et al. (1993) *Cell* 74:115-125; Wilson, A. C. et al. (1997) *Mol. Cell. Biol.* 17:6139-6146), is a binding partner that upregulates the transcriptional activity of both the originally identified PGC-1, hereinafter referred to as PGC-1α, and PGC-1β. The present invention is further based, at least in part, on the discovery that both PGC-1α and PGC-1β induce mitochondrial gene expression in neuroblastoma cells suggesting an important role in neurological disorders. The present invention is yet further based, at least in part, on the discovery that both PGC-1α, and PGC-1β induce the expression of enzymes involved in free radical metabolism such as superoxide dismutase (Mn-SOD) and glutathione peroxidase (GPx), suggesting an important role in the cellular defense against free radical damage.

The PGC-1β nucleic acid and protein molecules of the present invention are useful as modulating agents in regulating a variety of cellular processes, e.g., cellular determination and/or differentiation (e.g., brown adipose determination and/or differentiation), cellular metabolism, fatty acid oxidation, mitochondrial function and/or respiration, cellular signaling, and/or cellular proliferation. Accordingly, in one aspect, this invention provides isolated nucleic acid molecules encoding PGC-1β proteins or biologically active portions thereof, as well as nucleic acid fragments suitable as primers or hybridization probes for the detection of PGC-1β-encoding nucleic acids.

In one embodiment, a PGC-1β nucleic acid molecule of the invention is at least 50%, 55%, 60%, 65%, 70%, 71%, 72%, 73%, 74%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the nucleotide sequence (e.g., to the entire length of the nucleotide sequence) shown in SEQ ID NO:1, 3, 4, or 6, or a complement thereof.

In a preferred embodiment, the isolated nucleic acid molecule includes the nucleotide sequence shown in SEQ ID NO:1, 3, 4, or 6, or a complement thereof. In another preferred embodiment, the isolated nucleic acid molecule includes nucleotides 1-660 of SEQ ID NO:3. In another preferred embodiment, the isolated nucleic acid molecule comprises nucleotides 1-1140 of SEQ ID NO:3. In another preferred embodiment, the nucleic acid molecule consists of the nucleotide sequence shown in SEQ ID NO:1, 3, 4, or 6.

In another embodiment, a PGC-1β nucleic acid molecule includes a nucleotide sequence encoding a protein having an amino acid sequence sufficiently identical to the amino acid sequence of SEQ ID NO:2 or 5. In a preferred embodiment, a PGC-1β nucleic acid molecule includes a nucleotide sequence encoding a protein having an amino acid sequence at least 50%, 55%, 60%, 65%, 70%, 71%, 72%, 73%, 74%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the entire length of the amino acid sequence of SEQ ID NO:2 or 5.

In another preferred embodiment, an isolated nucleic acid molecule encodes the amino acid sequence of human PGC-1β. In another preferred embodiment, an isolated nucleic acid molecule encodes the amino acid sequence of mouse PGC-1β. In yet another preferred embodiment, the nucleic acid molecule includes a nucleotide sequence encoding a protein having the amino acid sequence of SEQ ID NO:2 or 5. In yet another preferred embodiment, the nucleic acid molecule is at least 50, 75, 100, 125, 150, 175, 200, 250, 300, 350, 400, 450, 457, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600 or more nucleotides in length. In a further preferred embodiment, the nucleic acid molecule is at least 50, 75, 100, 125, 150, 175, 200, 250, 300, 350, 400, 450, 457, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600 or more nucleotides in length and encodes a protein having a PGC-1β activity (as described herein).

Another embodiment of the invention features nucleic acid molecules, preferably PGC-1β nucleic acid molecules, which specifically detect PGC-1β nucleic acid molecules relative to nucleic acid molecules encoding non-PGC-1β proteins. For example, in one embodiment, such a nucleic acid molecule is at least 20, 30, 40, 50, 75, 100, 125, 150, 175, 200, 250, 300, 350, 400, 450, 457, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600 or more nucleotides in length and hybridizes under stringent conditions to a nucleic acid molecule comprising the nucleotide sequence shown in SEQ ID NO:1 or 4, or a complement thereof.

In preferred embodiments, the nucleic acid molecules are at least 15 (e.g., 15 contiguous) nucleotides in length and hybridize under stringent conditions to the nucleotide molecules set forth in SEQ ID NO:1 or 4.

In other preferred embodiments, the nucleic acid molecule encodes a naturally occurring allelic variant of a polypeptide comprising the amino acid sequence of SEQ ID NO:2 or 5, wherein the nucleic acid molecule hybridizes to a complement of a nucleic acid molecule comprising SEQ ID NO:1, 3, 4, or 6, respectively, under stringent conditions.

Another embodiment of the invention provides an isolated nucleic acid molecule which is antisense to a PGC-1β nucleic acid molecule, e.g., the coding strand of a PGC-1β nucleic acid molecule.

Another aspect of the invention provides a vector comprising a PGC-1β nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a PGC-1β protein, by culturing in a suitable medium, a host cell, e.g., a mammalian host cell such as a non-human mammalian cell, of the invention containing a recombinant expression vector, such that the protein is produced.

Another aspect of this invention features isolated or recombinant PGC-1β proteins and polypeptides. In one embodiment, an isolated PGC-1β protein includes at least one or more of the following domains: an LXXLL motif, an RRM, an AD, an HBM, and/or a glutamic/aspartic acid rich acidic domain.

In a preferred embodiment, a PGC-1β protein includes at least one or more of the following domains: an LXXLL motif, an RRM, an AD, an HBM, and/or a glutamic/aspartic acid rich acidic domain, and has an amino acid sequence at least about 50%, 55%, 60%, 65%, 67%, 68%, 70%, 71%, 72%, 73%, 74%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the amino acid sequence of SEQ ID NO:2 or 5.

In another preferred embodiment, a PGC-1β protein includes at least one or more of the following domains: an LXXLL motif, an RRM, an AD, an HBM, and/or a glutamic/aspartic acid rich acidic domain, and has a PGC-1β activity (as described herein).

In yet another preferred embodiment, a PGC-1β protein includes at least one or more of the following domains: an LXXLL motif, an RRM, an AD, an HBM, and/or a glutamic/aspartic acid rich acidic domain, and is encoded by a nucleic acid molecule having a nucleotide sequence which hybridizes under stringent hybridization conditions to a complement of a nucleic acid molecule comprising the nucleotide sequence of SEQ ID NO:1, 3, 4, or 6.

In another embodiment, the invention features fragments of the protein having the amino acid sequence of SEQ ID NO:2 or 5, wherein the fragment comprises at least 10, 15, 20, 25, 30, 35, 40, 45, 50, 75, 100, 125, 150, 175, 200, 250, 300, 350, 400, 450, 500, 550, 600, 650, 700, 750, 800, 850, 900, 950, or 1000 amino acids (e.g., contiguous amino acids) of the amino acid sequence of SEQ ID NO:2 or 5. In another embodiment, a PGC-1β protein has the amino acid sequence of SEQ ID NO:2 or 5.

In another embodiment, the invention features a PGC-1β protein which is encoded by a nucleic acid molecule consisting of a nucleotide sequence at least about 50%, 55%, 60%, 65%, 70%, 71%, 72%, 73%, 74%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to a nucleotide sequence of SEQ ID NO:1, 3, 4, or 6, or a complement thereof. This invention further features a PGC-1β protein which is encoded by a nucleic acid molecule consisting of a nucleotide sequence which hybridizes under stringent hybridization conditions to a complement of a nucleic acid molecule comprising the nucleotide sequence of SEQ ID NO:1, 3, 4, or 6, or a complement thereof.

The proteins of the present invention or portions thereof, e.g., biologically active portions thereof, can be operatively linked to a non-PGC-1β polypeptide (e.g., heterologous amino acid sequences) to form fusion proteins. The invention further features antibodies, such as monoclonal or polyclonal antibodies, that specifically bind proteins of the invention, preferably PGC-1β proteins. In addition, the PGC-1β proteins or biologically active portions thereof can be incorporated into pharmaceutical compositions, which optionally include pharmaceutically acceptable carriers.

In another aspect, the present invention provides a method for detecting the presence of a PGC-1β nucleic acid molecule, protein, or polypeptide in a biological sample by contacting the biological sample with an agent capable of detecting a PGC-1β nucleic acid molecule, protein, or polypeptide such that the presence of a PGC-1β nucleic acid molecule, protein or polypeptide is detected in the biological sample.

In another aspect, the present invention provides a method for detecting the presence of PGC-1β activity in a biological sample by contacting the biological sample with an agent capable of detecting an indicator of PGC-1β activity such that the presence of PGC-1β activity is detected in the biological sample.

In another aspect, the invention provides a method for modulating PGC-1β activity comprising contacting a cell capable of expressing PGC-1β with an agent that modulates PGC-1β activity such that PGC-1β activity in the cell is modulated. In one embodiment, the agent inhibits PGC-1β activity. In another embodiment, the agent stimulates PGC-1β activity. In one embodiment, the agent is an antibody that specifically binds to a PGC-1β protein. In another embodiment, the agent modulates expression of PGC-1β by modulating transcription of a PGC-1β gene or translation of a PGC-1β mRNA. In yet another embodiment, the agent is a nucleic acid molecule having a nucleotide sequence that is antisense to the coding strand of a PGC-1β mRNA or a PGC-1β gene.

In one embodiment, the methods of the present invention are used to treat a subject having a disorder characterized by aberrant or unwanted PGC-1β protein or nucleic acid expression or activity by administering an agent which is a PGC-1β modulator to the subject. In one embodiment, the PGC-1β modulator is a PGC-1β protein. In another embodiment the PGC-1β modulator is a PGC-1β nucleic acid molecule. In yet another embodiment, the PGC-1β modulator is a peptide, peptidomimetic, or other small molecule. In a preferred embodiment, the disorder characterized by aberrant or unwanted PGC-1β protein or nucleic acid expression is a PGC-1β-associated disorder, e.g., a metabolic disorder or a neurological disorder, as described herein. In another preferred embodiment, the disorder is characterized by free radical damage.

The present invention also provides diagnostic assays for identifying the presence or absence of a genetic alteration characterized by at least one of (i) aberrant modification or mutation of a gene encoding a PGC-1β protein; (ii) misregulation of the gene; and (iii) aberrant post-translational modification of a PGC-1β protein, wherein a wild-type form of the gene encodes a protein with a PGC-1β activity.

In another aspect the invention provides methods for identifying a compound that binds to or modulates the activity of a PGC-1β protein, by providing an indicator composition comprising a PGC-1β protein having PGC-1β activity, contacting the indicator composition with a test compound, and determining the effect of the test compound on PGC-1β activity in the indicator composition to identify a compound that modulates the activity of a PGC-1β protein.

In other embodiments, the invention provides methods for identifying a subject having a metabolic disorder, or at risk for developing a metabolic disorder; methods for identifying a compound capable of treating a metabolic disorder characterized by aberrant PGC-1 nucleic acid expression or PGC-1 polypeptide activity; and methods for treating a subject having a metabolic disorder characterized by aberrant PGC-1 polypeptide activity or aberrant PGC-1 nucleic acid expression.

In yet other embodiments, the invention provides methods for identifying a subject having a neurological disorder, or at risk for developing a neurological disorder; methods for identifying a compound capable of treating a neurological disorder characterized by aberrant PGC-1 nucleic acid expression or PGC-1 polypeptide activity; and methods for treating a subject having a neurological disorder characterized by aberrant PGC-1 polypeptide activity or aberrant PGC-1 nucleic acid expression.

In yet further embodiments, the invention provides methods for identifying a subject having a disorder characterized by free radical damage to cells, or at risk for developing a disorder characterized by free radical damage to cells; methods for identifying a compound capable of treating a disorder characterized by free radical damage to cells characterized by aberrant PGC-1 nucleic acid expression or PGC-1 polypeptide activity; and methods for treating a subject having such a disorder characterized by aberrant PGC-1 polypeptide activity or aberrant PGC-1 nucleic acid expression.

In another embodiment, the invention provides a method for identifying a compound which modulates the interaction of a PGC-1α protein with an HCF protein comprising contacting, in the presence of the compound, the PGC-1α protein and the HCF protein under conditions which allow binding of the HCF protein to the PGC-1α protein to form a complex; and detecting the formation of a complex of the PGC-1α protein and the HCF protein in which the ability of the compound to modulate the interaction between the PGC-1 protein and the HCF protein is indicated by a change in complex formation as compared to the complex formed (e.g., structure and/or amount of complex formed) in the absence of the compound.

Other features and advantages of the invention will be apparent from the following detailed description and claims.

BRIEF DESCRIPTION OF THE DRAWINGS

FIGS. 1A-1B depict the cDNA sequence of murine PGC-1β. The nucleotide sequence corresponds to nucleic acids 1 to 3664 of SEQ ID NO:1. The translation start codon and the stop codon are underlined.

FIG. 2 depicts the predicted protein sequence of murine PGC-1β. The amino acid sequence corresponds to residues 1 to 1014 of SEQ ID NO:2. The three LXXLL motifs are underlined, the RRM (RNA binding motif) is shown in bold, and the HBM (host cell binding factor motif) is boxed.

FIGS. 3A-3B depict the cDNA sequence of human PGC-1β. The nucleotide sequence corresponds to nucleic acids 1 to 3030 of SEQ ID NO:4. The translation start codon and the stop codon are underlined.

FIG. 4 depicts the predicted protein sequence of human PGC-1β. The amino acid sequence corresponds to residues 1 to 1009 of SEQ ID NO:5. The two LXXLL motifs are underlined, the RRM (RNA binding motif) is shown in bold, and the HBM (host cell binding factor motif) is boxed.

FIG. 9 depicts the interaction and activation of PGC-1 by HCF.

DETAILED DESCRIPTION OF THE INVENTION

Figure 5:
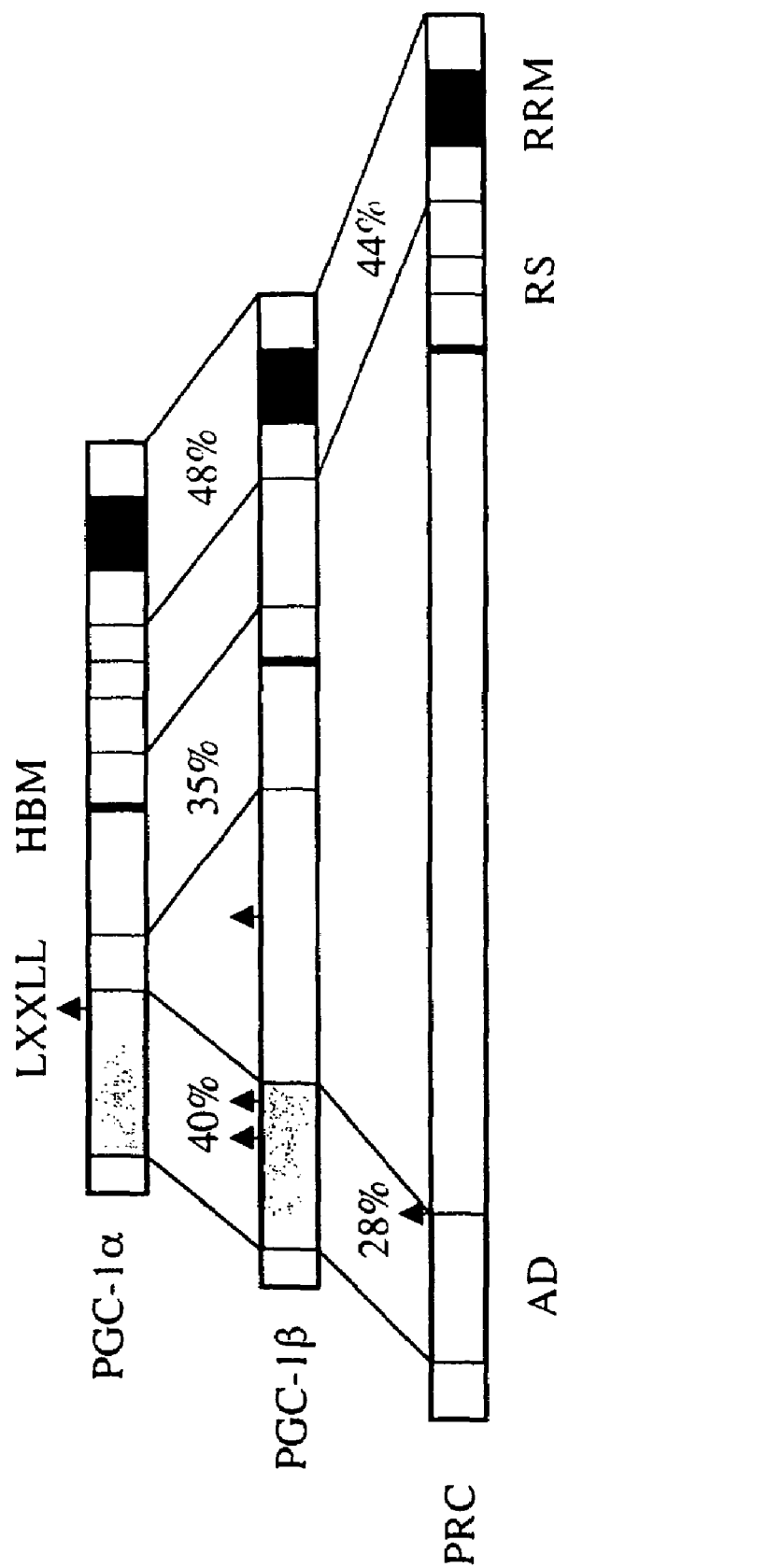
FIG. 5 depicts a schematic diagram of an alignment between murine PGC-1α, PGC-1β and PRC. The percent identity of the regions of each protein to PGC-1β is indicated. Conserved domains and/or motifs include the activation domain (AD), LXXLL and HBM motifs, the RS domain, and the RRM motif. The HBM motif is conserved in all three PGC-1 related proteins.

The present invention is based, at least in part, on the discovery of novel members of the family of PGC-1 molecules, referred to herein as PGC-1β nucleic acid and protein molecules. The present invention is further based, at least in part, on the discovery that PGC-1β is upregulated during brown fat determination/differentiation, but is not regulated in animals upon cold exposure or in brown adipose cells upon treatment with forskolin. The present invention is further based, at least in part, on the discovery that PGC-1β expression is upregulated in the liver during fasting. The present invention is further based, at least in part, on the discovery that PGC-1β induces fatty acid oxidation gene expression in the liver and skeletal muscle. The present invention is further based, at least in part, on the discovery that PGC-1β is highly expressed in brown adipose tissue (BAT) and heart (tissues that contain high levels of mitochondria and substrate oxidation) and on the discovery that PGC-1β is a potent coactivator of NRF1. The present invention is still further based, at least in part, on the discovery that host cell factor (HCF), a cellular protein that is involved in herpes simplex virus (HSV) infection and cell cycle regulation (Wilson, A. C. et al. (1993) *Cell* 74:115-125; Wilson, A. C. et al. (1997) *Mol. Cell. Biol.* 17:6139-6146), is a binding partner that upregulates the transcriptional activity of both the originally identified PGC-1 (hereinafter referred to as PGC-1α), and PGC-1β. The present invention is further based, at least in part, on the discovery that both PGC-1α and PGC-1β induce mitochondrial gene expression in neuroblastoma cells. The present invention is yet further based, at least in part, on the discovery that both PGC-1α, and PGC-1β induce the expression of enzymes involved in free radical metabolism such as superoxide dismutase (Mn-SOD) and glutathione peroxidase (GPx), suggesting an important role in the cellular defense against free radical damage.

The PGC-1β nucleic acid and protein molecules of the present invention are useful as modulating agents in regulating a variety of cellular processes, e.g., cellular determination and/or differentiation (e.g., brown adipose determination and/or differentiation), cellular metabolism, fatty acid oxidation, mitochondrial function and/or respiration, cellular signaling, cellular defense, and/or cellular proliferation.

Thus, the PGC-1β molecules of the present invention provide novel diagnostic targets and therapeutic agents to control metabolic disorders, neurological disorders and free-radical damage-related disorders. As used herein, the term "metabolic disorder" includes, but is not limited to, conditions, disorders, and/or diseases caused or affected by aberrant regulation of metabolism, e.g., aberrant regulation of metabolism caused by aberrant regulation of PGC-1β expression or activity.

For example, in one embodiment, a metabolic disorder includes a "brown adipose cell disorder". As used herein, a "brown adipose cell disorder" includes a disease, disorder, or condition which affects a brown adipose cell or tissue. Brown adipose cell disorders include diseases, disorders, or conditions associated with aberrant thermogenesis or aberrant brown adipose cell content or function. Brown adipose cell disorders can be characterized by a misregulation (e.g., downregulation or upregulation) of PGC-1β expression or activity. Examples of brown adipose cell disorders include disorders such as obesity, overweight, anorexia, cachexia, and diabetes (e.g., type 1 diabetes, type 2 diabetes, and maturity onset diabetes of the young (MODY)). Obesity is defined as a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/2m or more, or 29.9 kg/$^2$m or more, all of which are typically referred to as overweight (National Institute of Health, Clinical Guidelines on the Identification, Evaluation, and Treatment of Overweight and Obesity in Adults (1998)).

Metabolic disorders also include disorders associated with aberrant glucose homeostasis, for example, diabetes (e.g., type 1 diabetes, type 2 diabetes, and maturity onset diabetes of the young (MODY)) and disorders characterized by underproduction of glucose, e.g., hepatic enzyme abnormalities which result in hypoglycemia; and hypoglycemia, e.g., secondary hypoglycemia caused by other diseases, disorders, or conditions. Metabolic disorders may also include any other disorder or condition that is affected by abnormalities of glucose homeostasis, e.g., weight disorders such as obesity, cachexia, anorexia, and disorders associated with insufficient insulin activity. Disorders associated with body weight are disorders associated with abnormal body weight or abnormal control of body weight. As used herein, the language "diseases associated with or characterized by insufficient insulin activity" includes disorders or diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of β cells as in IDDM (type 1 diabetes), secretion, such as impairment of insulin secretory responses as in NIDDM (type 2 diabetes), the form of the insulin molecule itself, e.g., primary, secondary or tertiary structure, effects of insulin on target cells, e.g., insulin-resistance in bodily tissues, e.g., peripheral tissues, and responses of target cells to insulin. See Braunwald, E. et al. eds. Harrison's Principles of Internal Medicine, Eleventh Edition (McGraw-Hill Book Company, New York, 1987) pp. 1778-1797; Robbins, S. L. et al. Pathologic Basis of Disease, 3rd Edition (W.B. Saunders Company, Philadelphia, 1984) p. 972 for further descriptions of abnormal insulin activity in IDDM and NIDDM and other forms of diabetes As used herein, the term "neurological disorder" includes, but is not limited to, conditions, disorders, and/or diseases caused or affected by aberrant regulation of brain energy metabolism, e.g., aberrant regulation of brain energy metabolism caused by aberrant regulation of PGC-1 expression or activity. For example, in one embodiment, a "neurological disorder" includes disorders of the nervous system, including, but not limited to those involving the brain, the central and peripheral nervous system, and the interfaces between muscles and the nerves. Some examples of neurological related disorders include, without limitation, Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease. "Neurological disorders" also includes neurological disorders associated with inflammation, e.g. stroke, traumatic injury to the brain, traumatic injury to the spinal cord, spinal crush, central and peripheral nervous system trauma (CNS disorders).

Examples of CNS disorders such as cognitive and neurodegenerative disorders, include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety. "Neurological disorders" also includes disorders related to free radical damage.

As used herein, the term "free-radical damage-related disorder" includes, but is not limited to, conditions, disorders, and/or diseases caused or affected by aberrant regulation of free radical metabolism, e.g., aberrant regulation of free-radical metabolism caused by aberrant regulation of PGC-1 expression or activity. For example, in one embodiment, a "free-radical damage-related disorder" includes, neurodegenerative diseases and neurodegenerative disorders such as Huntington's (HD), Parkinson's (PD), and Alzheimer's diseases, as well as amyotrophic lateral sclerosis (ALS), commonly known as Lou Gehrig's disease. A "free-radical damage-related disorder" also includes biological senescence or aging defined as an increase in the risk of death which results from deleterious cellular changes produced by free-radical reactions. These cell-damaging processes are largely initiated in the course of mitochondrial respiration, while life span is determined by the rate of damage to the mitochondria. A "free-radical damage-related disorder" further includes all forms of cancer and heart disease as well as all known disorders associated with impaired free-radical metabolism.

Because the PGC-1β molecules of the invention interact with host cell factor (HCF), they may also provide novel diagnostic targets and therapeutic agents to control viral disorders and/or cellular proliferation, growth, and/or differentiation disorders. Viral disorders included disorders, diseases, and/or conditions caused or affected by infection of a cell or a subject by a virus, e.g., herpes simplex virus (HSV). Cellular proliferation, growth, differentiation, disorders include those disorders that affect cell proliferation, growth, and/or differentiation processes. As used herein, a "cellular proliferation, growth, and/or differentiation process" is a process by which a cell increases in number, size or content, by which a cell develops a specialized set of characteristics which differ from that of other cells, or by which a cell moves closer to or further from a particular location or stimulus. Thus, the PGC-1β molecules may modulate cellular growth, and/or differentiation and may play a role in disorders characterized by aberrantly regulated growth, and/or differentiation. Such disorders include cancer, e.g., carcinomas, sarcomas, leukemias, and lymphomas, and in particular, cancers caused by infection with a virus, e.g., herpes simplex virus (HSV); tumor angiogenesis and metastasis; skeletal dysplasia; hepatic disorders; and hematopoietic and/or myeloproliferative disorders.

PGC-1β-associated or related disorders also include disorders affecting tissues in which PGC-1β protein is expressed, e.g., brown adipose tissue, white adipose tissue, liver, and/or heart.

As used herein, "brown adipose cell activity" includes an activity exerted by a brown adipose cell, or an activity that takes place in a brown adipose cell. For example, such activities include cellular processes that contribute to the physiological role of brown adipose cells, such as brown adipose cell differentiation and mitochondrial activity and include, but are not limited to, cell proliferation, differentiation, growth, migration, programmed cell death, uncoupled mitochondrial respiration, and thermogenesis.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, a member of the family of PGC-1β molecules of the invention comprises at least one "LXXLL motif" in the protein or corresponding nucleic acid molecule. As used herein, an "LXXLL motif" refers to a motif wherein X can be any amino acid and which mediates an interaction between an nuclear receptor and a coactivator (Heery et al. (1997) Nature 397:733-736; Torchia et al. (1997) Nature 387:677-684). In a preferred embodiment, a PGC-1β protein has at least two or three LXXLL motifs. Three LXXLL motifs were identified in the amino acid sequence of mouse PGC-1β at about residues 140-144, 156-160, and 343-347 of SEQ ID NO:2 (FIG. 2). Two LXXLL motifs were identified in the amino acid sequence of human PGC-1β at about residues 144-148 and 331-335 of SEQ ID NO:5 (FIG. 4).

In another embodiment of the invention, a PGC-1β molecule of the invention comprises at least one "RNA recognition motif" or "RRM" in the protein or corresponding nucleic acid molecule. As used interchangeably herein, an "RNA recognition motif" or "RRM" is an amino acid sequence which can bind an RNA molecule or a single stranded DNA molecule. In a preferred embodiment an RRM is found near the C-terminus of a PGC-1β protein and comprises about 50-160, 60-150, 70-140, 80-130, 90-120, or preferably about 108 amino acid residues. RRMs are described in Lodish, H., Darnell, J., and Baltimore, D. Molecular Cell Biology, 3rd ed. (W.H. Freeman and Company, New York, N.Y., 1995). An RRM was identified in the amino acid sequence of mouse PGC-1β at about residues 894-958 of SEQ ID NO:2 (FIG. 2). An RRM was identified in the amino acid sequence of human PGC-1β at about residues 889-953 of SEQ ID NO:5 (FIG. 5).

In another embodiment, a PGC-1β molecule of the invention comprises at least one "activation domain" or "AD" in the protein or corresponding nucleic acid molecule. As used interchangeably herein, an "activation domain" or "AD" is a protein domain which has autonomous transcriptional activity when fused to a heterologous DNA binding domain. In a preferred embodiment, an AD is located N-terminal 220 amino acid residues of a PGC-1β protein and comprises about 50-375, 75-350, 100-325, 125-300, 150-275, 175-250, 200-225, or about 220 amino acid residues. An AD was identified in the amino acid sequence of mouse PGC-1β at about amino acid residues 1-220 of SEQ ID NO:2.

In still another embodiment, a PGC-1β molecule of the invention comprises at least one "host cell factor binding motif" in the protein or corresponding nucleic acid molecule. As used interchangeably herein, a "host cell factor binding motif", "host cell factor binding site", or "HBM" includes an amino acid motif capable of mediating the interaction of a PGC-1 molecule and host cell factor (HCF), a protein involved in the regulation of cell cycle progression and the assembly of a multiprotein transcriptional complex during herpes simplex virus (HSV) infection (Freiman, R. N. and Herr, W. (1997) Genes Dev. 11:3122-3127; Andersson, U. and Scarpulla, R. C. (2001) Mol. Cell. Biol. 21:3738-3749). In a preferred embodiment, an HBM has the consensus sequence [D/E]-H-X-Y, wherein [D/E] indicates either D or E at the indicated position, and wherein X indicates any amino acid at the indicated position. An HBM was identified in the amino acid sequence of mouse PGC-1β at about residues 683-686 of SEQ ID NO:2 (FIG. 2). An HBM was also identified in the amino acid sequence of human PGC-1β at about residues 677-680 of SEQ ID NO:5 (FIG. 5). An HBM was also identified in the amino acid sequence of mouse PGC-1α at about residues 382-385 of SEQ ID NO:9, and in the amino acid sequence of human PGC-1α at about residues 383-386 of SEQ ID NO:11.

In another embodiment, a PGC-1β molecule of the invention comprises at least one "glutamic/aspartic acid rich acidic domain" in the protein or corresponding nucleic acid molecule. As used herein, a "glutamic/aspartic acid rich acidic domain" includes a protein domain of about 10-40, 12-35, 14-30, 16-25, or preferably about 18, 21, or 23 amino acid residues. Glutamic/aspartic acid rich acidic domains are found in proteins that regulate diverse biological processes, including transcription, assembly of RNA-protein complexes, and modification of protein structure. In a preferred embodiment, all of the amino acid residues in a glutamic/aspartic acid rich acidic domain are acidic residues (e.g., glutamic acid or aspartic acid). In other embodiments a glutamic/aspartic acid rich acidic domain may have at least 1, 2, 3, 4, 5, 6, 7, or 8 amino acid residues which are not acidic. Preferably, a PGC-1β molecule comprises at least two glutamic/aspartic acid rich acidic domains. Two glutamic/aspartic acid rich acidic domains were identified in the amino acid sequence of mouse PGC-1β at about residues 429-451 and 798-815 of SEQ ID NO:2. Two glutamic/aspartic acid rich acidic domains were identified in the amino acid sequence of human PGC-1β at about residues 418-438 and 793-810 of SEQ ID NO:5.

In a preferred embodiment, the PGC-1β molecules of the invention include at least one or more of the following domains: an LXXLL motif, an RRM, an AD, an HBM, and/or a glutamic/aspartic acid rich acidic domain.

Isolated proteins of the present invention, preferably PGC-1β proteins, have an amino acid sequence sufficiently identical to the amino acid sequence of SEQ ID NO:2 or 5, or are encoded by a nucleotide sequence sufficiently identical to SEQ ID NO:1, 3, 4, or 6. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, an "PGC-1β activity", "biological activity of PGC-1β" or "functional activity of PGC-1β", refers to an activity exerted by a PGC-1β protein, polypeptide or nucleic acid molecule on a PGC-1β responsive cell or tissue, or on a PGC-1β protein substrate, as determined in vivo, or in vitro, according to standard techniques. In one embodiment, a PGC-1β activity is a direct activity, such as an association with a PGC-1β-target molecule. As used herein, a "target molecule" or "binding partner" is a molecule with which a PGC-1β protein binds or interacts in nature, such that PGC-1β-mediated function is achieved. In an exemplary embodiment, a PGC-1β target molecule is a nuclear receptor (e.g., HNF4α, PPARα, retinoic acid receptor α (RARα), thyroid hormone receptor β (TRβ), and glucocorticoid receptor (GR)), host cell factor (HCF), nuclear respiratory factor 1 (NRF1), or a basal transcription factor. Alternatively, a PGC-1β activity is an indirect activity, such as a cellular signaling activity mediated by interaction of the PGC-1β protein with a PGC-1β target molecule. The biological activities of PGC-1β are described herein. For example, the PGC-1β proteins of the present invention can have one or more of the following activities: 1) interaction with a nuclear receptor (e.g., HNF4α, PPARα, retinoic acid receptor α (RARα), thyroid hormone receptor β (TRβ), or glucocorticoid receptor (GR)); 2) interaction with HCF; 3) interaction with NRF1; 4) interaction with a basal transcription factor; 5) modulation of the activity, e.g., the transcriptional activity, of a nuclear receptor and/or NRF1; 6) modulation of brown adipose cell determination and/or differentiation; 7) modulation on intra- or inter-cellular signaling; 8) modulation of viral infection (e.g., via interaction with HCF); 9) modulation of cellular proliferation; 10) modulation of metabolism; 11) modulation of mitochondrial activity and/or biogenesis; and 12) modulation of fatty acid β-oxidation.

Accordingly, another embodiment of the invention features isolated PGC-1β proteins and polypeptides having a PGC-1β activity. Other preferred proteins are PGC-1β proteins having one or more of the following domains: an LXXLL motif, an RRM, an AD, an HBM, and/or a glutamic/aspartic acid rich acidic domain, preferably, a PGC-1β activity.

Additional preferred proteins have at least one or more of an LXXLL motif, an RRM, an AD, an HBM, and/or a glutamic/aspartic acid rich acidic domain, and are, preferably, encoded by a nucleic acid molecule having a nucleotide sequence which hybridizes under stringent hybridization conditions to a complement of a nucleic acid molecule comprising the nucleotide sequence of SEQ ID NO:1, 3, 4, or 6.

The nucleotide sequence of the isolated mouse PGC-1β cDNA is shown in FIGS. 1A-1B and in SEQ ID NO:1, and the predicted amino acid sequence of the mouse PGC-1β polypeptide is shown in FIG. 2 and in SEQ ID NO:2. The nucleotide sequence of the isolated human PGC-1β cDNA is shown in FIGS. 3A-3B and in SEQ ID NO:4, and the predicted amino acid sequence of the human PGC-1β polypeptide is shown in FIG. 4 and in SEQ ID NO:5. These deposits will be maintained under the terms of the Budapest Treaty on the International Recognition of the Deposit of Microorganisms for the Purposes of Patent Procedure. These deposits were made merely as a convenience for those of skill in the art and are not an admission that deposits are required under 35 U.S.C. §112.

The mouse PGC-1β gene, which is approximately 3664 nucleotides in length, encodes a protein having a molecular weight of approximately 111.5 kD and is approximately 1014 amino acid residues in length. The human PGC-1β gene, which is approximately 3030 nucleotides in length, encodes a protein having a molecular weight of approximately 111.0 kD and is approximately 1009 amino acid residues in length.

Various aspects of the invention are described in further detail in the following subsections:

I. ISOLATED NUCLEIC ACID MOLECULES

One aspect of the invention pertains to isolated nucleic acid molecules that encode PGC-1β proteins or biologically active portions thereof, as well as nucleic acid fragments sufficient for use as hybridization probes to identify PGC-1β-encoding nucleic acid molecules (e.g., PGC-1β mRNA) and fragments for use as PCR primers for the amplification or mutation of PGC-1β nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecules of the present invention can be single-stranded or double-stranded, but preferably are double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PGC-1β nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, or 6, or a portion thereof, can be isolated using standard molecular biology techniques and the sequence information provided herein. Using all or portion of the nucleic acid sequence of SEQ ID NO:1, 3, 4, or 6, as a hybridization probe, PGC-1β nucleic acid molecules can be isolated using standard hybridization and cloning techniques (e.g., as described in Sambrook, J., Fritsh, E. F., and Maniatis, T. *Molecular Cloning: A Laboratory Manual*. 2nd ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 4, or 6, can be isolated by the polymerase chain reaction (PCR) using synthetic oligonucleotide primers designed based upon the sequence of SEQ ID NO:1, 3, 4, or 6.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to PGC-1β nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, 4, or 6. This cDNA may comprise sequences encoding the mouse PGC-1β protein (i.e., "the coding region", from nucleotides 65-3106), as well as 5' untranslated sequences (nucleotides 1-64) and 3' untranslated sequences (nucleotides 3107-3664) of SEQ ID NO:1. Alternatively, the nucleic acid molecule can comprise only the coding region of SEQ ID NO:1 (e.g., nucleotides 65-3106, corresponding to SEQ ID NO:3). Accordingly, in another embodiment, an isolated nucleic acid molecule of the invention comprises SEQ ID NO:3 and nucleotides 1-65 of SEQ ID NO:1. In yet another embodiment, the isolated nucleic acid molecule comprises SEQ ID NO:3 and nucleotides 3107-3664 of SEQ ID NO:1. In yet another embodiment, the nucleic acid molecule consists of the nucleotide sequence set forth as SEQ ID NO:1 or SEQ ID NO:3. In still another embodiment, the nucleic acid molecule can comprise the coding region of SEQ ID NO:1 (e.g., nucleotides 65-3106, corresponding to SEQ ID NO:3), as well as a stop codon (e.g., nucleotides 3107-3109 of SEQ ID NO:1).

This cDNA may comprise sequences encoding the human PGC-1β protein (i.e., "the coding region", from nucleotides 1-3027), as well as a stop codon (nucleotides 3028-3030) of SEQ ID NO:4. Alternatively, the nucleic acid molecule can comprise only the coding region of SEQ ID NO:4 (e.g., nucleotides 1-3027, corresponding to SEQ ID NO:6). In yet another embodiment, the nucleic acid molecule consists of the nucleotide sequence set forth as SEQ ID NO:4 or SEQ ID NO:6.

In another preferred embodiment, an isolated nucleic acid molecule of the invention comprises a nucleic acid molecule which is a complement of the nucleotide sequence shown in SEQ ID NO:1, 3, 4, or 6, or a portion of any of these nucleotide sequences. A nucleic acid molecule which is complementary to the nucleotide sequence shown in SEQ ID NO:1, 3, 4, or 6, is one which is sufficiently complementary to the nucleotide sequence shown in SEQ ID NO:1, 3, 4, or 6, such that it can hybridize to the nucleotide sequence shown in SEQ ID NO:1, 3, 4, or 6, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the entire length of the nucleotide sequence shown in SEQ ID NO:1, 3, 4, or 6, or a portion of any of these nucleotide sequences.

Moreover, the nucleic acid molecule of the invention can comprise only a portion of the nucleic acid sequence of SEQ ID NO:1, 3, 4, or 6, for example, a fragment which can be used as a probe or primer or a fragment encoding a portion of a PGC-1β protein, e.g., a biologically active portion of a PGC-1β protein. The nucleotide sequences determined from the cloning of the PGC-1β genes allow for the generation of probes and primers designed for use in identifying and/or cloning other PGC-1β family members, as well as PGC-1β homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 4, or 6, of an anti-sense sequence of SEQ ID NO:1, 3, 4, or 6, or of a naturally occurring allelic variant or mutant of SEQ ID NO:1, 3, 4, or 6. In one embodiment, a nucleic acid molecule of the present invention comprises a nucleotide sequence which is greater than 50, 75, 100, 125, 150, 175, 200, 250, 300, 350, 400, 450, 457, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600 or more nucleotides in length and hybridizes under stringent hybridization conditions to a nucleic acid molecule of SEQ ID NO:1, 3, 4, or 6.

Probes based on the PGC-1β nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PGC-1β protein, such as by measuring a level of a PGC-1β-encoding nucleic acid in a sample of cells from a subject e.g., detecting PGC-1β mRNA levels or determining whether a genomic PGC-1β gene has been mutated or deleted.

A nucleic acid fragment encoding a "biologically active portion of a PGC-1β protein" can be prepared by isolating a portion of the nucleotide sequence of SEQ ID NO:1, 3, 4, or 6, which encodes a polypeptide having a PGC-1β biological activity (the biological activities of the PGC-1β proteins are described herein), expressing the encoded portion of the PGC-1β protein (e.g., by recombinant expression in vitro) and assessing the activity of the encoded portion of the PGC-1β protein.

The invention further encompasses nucleic acid molecules that differ from the nucleotide sequence shown in SEQ ID NO:1, 3, 4, or 6, due to degeneracy of the genetic code and thus encode the same PGC-1β proteins as those encoded by the nucleotide sequence shown in SEQ ID NO:1, 3, 4, or 6, an isolated nucleic acid molecule of the invention has a nucleotide sequence encoding a protein having an amino acid sequence shown in SEQ ID NO:2 or 5.

In addition to the PGC-1β nucleotide sequences shown in SEQ ID NO:1, 3, 4, or 6, it will be appreciated by those skilled in the art that DNA sequence polymorphisms that lead to changes in the amino acid sequences of the PGC-1β proteins may exist within a population (e.g., the human population). Such genetic polymorphism in the PGC-1β genes may exist among individuals within a population due to natural allelic variation. As used herein, the terms "gene" and "recombinant gene" refer to nucleic acid molecules which include an open reading frame encoding a PGC-1β protein, preferably a mammalian PGC-1β protein, and can further include non-coding regulatory sequences, and introns.

Allelic variants of human PGC-1β include both functional and non-functional PGC-1β proteins. Functional allelic variants are naturally occurring amino acid sequence variants of the human PGC-1β protein that maintain the ability to bind a PGC-1β target molecule and or modulate transcriptional and/or cell differentiation and/or proliferation mechanisms. Functional allelic variants will typically contain only conservative substitution of one or more amino acids of SEQ ID NO:2 or 5, or substitution, deletion or insertion of non-critical residues in non-critical regions of the protein.

Non-functional allelic variants are naturally occurring amino acid sequence variants of the mouse or human PGC-1β proteins that do not have the ability to either bind a PGC-1β target molecule and/or modulate any of the PGC-1β activities described herein. Non-functional allelic variants will typically contain a non-conservative substitution, a deletion, or insertion or premature truncation of the amino acid sequence of SEQ ID NO:2 or 5, or a substitution, insertion or deletion in critical residues or critical regions of the protein.

The present invention further provides non-human orthologues of the mouse or human PGC-1β proteins. Orthologues of the mouse or human PGC-1β proteins are proteins that are isolated from non-human organisms and possess the same PGC-1β activities of the mouse or human PGC-1β proteins, as described herein. Orthologues of the mouse or human PGC-1β proteins can readily be identified as comprising an amino acid sequence that is substantially identical to SEQ ID NO:2 or 5.

Moreover, nucleic acid molecules encoding other PGC-1β family members and, thus, which have a nucleotide sequence which differs from the PGC-1β sequences of SEQ ID NO:1, 3, 4, or 6, are intended to be within the scope of the invention. For example, another PGC-1β cDNA can be identified based on the nucleotide sequence of mouse or human PGC-1β. Moreover, nucleic acid molecules encoding PGC-1β proteins from different species, and which, thus, have a nucleotide sequence which differs from the PGC-1β sequences of SEQ ID NO:1, 3, 4, or 6, are intended to be within the scope of the invention. For example, a mouse PGC-1β cDNA can be identified based on the nucleotide sequence of a mouse or human PGC-1β.

Nucleic acid molecules corresponding to natural allelic variants and homologues of the PGC-1β cDNAs of the invention can be isolated based on their homology to the PGC-1β nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the PGC-1β cDNAs of the invention can further be isolated by mapping to the same chromosome or locus as the PGC-1β gene.

Accordingly, in another embodiment, an isolated nucleic acid molecule of the invention is at least 15, 20, 25, 30, 35, 40, 45, 50 or more nucleotides in length and hybridizes under stringent conditions to the nucleic acid molecule comprising the nucleotide sequence of SEQ ID NO:1, 3, 4, or 6. In other embodiment, the nucleic acid is at least 50, 75, 100, 125, 150, 175, 200, 250, 300, 350, 400, 450, 457, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.) = 2(\# of A+T bases) + 4(\# of G+C bases)$. For hybrids between 18 and 49 base pairs in length, $T_m(° C.) = 81.5 + 16.6(\log_{10}[Na^+]) + 0.41(\% G+C) - (600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M NaH$_2$PO$_4$, 1% SDS at 65° C. (see e.g., Church and Gilbert (1984) *Proc. Natl. Acad. Sci. USA* 81:1991-1995), or alternatively 0.2×SSC, 1% SDS.

Preferably, an isolated nucleic acid molecule of the invention that hybridizes under stringent conditions to the sequence of SEQ ID NO:1, 3, 4, or 6, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PGC-1β sequences that may exist in the population, the skilled artisan will further appreciate that changes can be introduced by mutation into the nucleotide sequences of SEQ ID NO:1, 3, 4, or 6, thereby leading to changes in the amino acid sequence of the encoded PGC-1β proteins, without altering the functional ability of the PGC-1β proteins. For example, nucleotide substitutions leading to amino acid substitutions at "non-essential" amino acid residues can be made in the sequence of SEQ ID NO:1, 3, 4, or 6. A "non-essential" amino acid residue is a residue that can be altered from the wild-type sequence of PGC-1β (e.g., the sequence of SEQ ID NO:2 or 5) without altering the biological activity, whereas an "essential" amino acid residue is required for biological activity. For example, amino acid residues that are conserved among the PGC-1β proteins of the present invention, e.g., those present in an activation domain, an LXXLL motif, or an HBM, are predicted to be particularly unamenable to alteration. Furthermore, additional amino acid residues that are conserved between the PGC-1β proteins of the present invention and other members of the PGC-1 family are not likely to be amenable to alteration.

Accordingly, another aspect of the invention pertains to nucleic acid molecules encoding PGC-1β proteins that contain changes in amino acid residues that are not essential for activity. Such PGC-1β proteins differ in amino acid sequence from SEQ ID NO:2 or 5, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to SEQ ID NO:2 or 5.

An isolated nucleic acid molecule encoding a PGC-1β protein identical to the protein of SEQ ID NO:2 or 5 can be created by introducing one or more nucleotide substitutions, additions or deletions into the nucleotide sequence of SEQ ID NO:1, 3, 4, or 6, such that one or more amino acid substitutions, additions or deletions are introduced into the encoded protein. Mutations can be introduced into SEQ ID NO:1, 3, 4, or 6, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a PGC-1β protein is preferably replaced with another amino acid residue from the same side chain family. Alternatively, in another embodiment, mutations can be introduced randomly along all or part of a PGC-1β coding sequence, such as by saturation mutagenesis, and the resultant mutants can be screened for PGC-1β biological activity to identify mutants that retain activity. Following mutagenesis of SEQ ID NO:1, 3, 4, or 6, the encoded protein can be expressed recombinantly and the activity of the protein can be determined.

In a preferred embodiment, a mutant PGC-1β protein can be assayed for the ability to interact with and/or coactivate a nuclear receptor, HCF, and/or NRF1, for the ability to modulate brown adipose cell differentiation, and/or for the ability to modulate mitochondrial activity and/or biogenesis.

In addition to the nucleic acid molecules encoding PGC-1β proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1β coding strand, or to only a portion thereof. In one embodiment, an antisense nucleic acid molecule is antisense to a "coding region" of the coding strand of a nucleotide sequence encoding a PGC-1β. The term "coding region" refers to the region of the nucleotide sequence comprising codons which are translated into amino acid residues (e.g., the coding region of mouse PGC-1β corresponds to SEQ ID NO:3, and the coding region of human PGC-1β corresponds to SEQ ID NO:6). In another embodiment, the antisense nucleic acid molecule is antisense to a "noncoding region" of the coding strand of a nucleotide sequence encoding PGC-1β. The term "noncoding region" refers to 5' and 3' sequences which flank the coding region that are not translated into amino acids (i.e., also referred to as 5' and 3' untranslated regions).

Given the coding strand sequences encoding PGC-1β disclosed herein (e.g., SEQ ID NO:3 or 6), antisense nucleic acids of the invention can be designed according to the rules of Watson and Crick base pairing. The antisense nucleic acid molecule can be complementary to the entire coding region of PGC-1β mRNA, but more preferably is an oligonucleotide which is antisense to only a portion of the coding or noncoding region of PGC-1β mRNA. For example, the antisense oligonucleotide can be complementary to the region surrounding the translation start site of PGC-1β mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PGC-1β protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave PGC-1β mRNA transcripts to thereby inhibit translation of PGC-1β mRNA. A ribozyme having specificity for a PGC-1β-encoding nucleic acid can be designed based upon the nucleotide sequence of a PGC-1β cDNA disclosed herein (i.e., SEQ ID NO:1, 3, 4, or 6). For example, a derivative of a *Tetrahymena* L-19 IVS RNA can be constructed in which the nucleotide sequence of the active site is complementary to the nucleotide sequence to be cleaved in a PGC-1β-encoding mRNA. See, e.g., Cech et al. U.S. Pat. No. 4,987,071; and Cech et al. U.S. Pat. No. 5,116,742. Alternatively, PGC-1β mRNA can be used to select a catalytic RNA having a specific ribonuclease activity from a pool of RNA molecules. See, e.g., Bartel, D. and Szostak, J. W. (1993) *Science* 261:1411-1418.

Alternatively, PGC-1β gene expression can be inhibited by targeting nucleotide sequences complementary to the regulatory region of the PGC-1β (e.g., the PGC-1β promoter and/or enhancers) to form triple helical structures that prevent transcription of the PGC-1β gene in target cells. See generally, Helene, C. (1991) *Anticancer Drug Des.* 6(6): 569-84; Helene, C. et al. (1992) *Ann. N.Y. Acad. Sci.* 660:27-36; and Maher, L. J. (1992) *Bioessays* 14(12):807-15.

In yet another embodiment, the PGC-1β nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670-675.

PNAs of PGC-1β nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PGC-1β nucleic acid molecules can also be used in the analysis of single base pair mutations in a gene, (e.g., by PNA-directed PCR clamping); as 'artificial restriction enzymes' when used in combination with other enzymes, (e.g., Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of PGC-1β can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PGC-1β nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res.* 24 (17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res.* 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) *Biotechniques* 6:958-976) or intercalating agents (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous PGC-1β gene within a cell line or microorganism may be modified by inserting a heterologous DNA regulatory element into the genome of a stable cell line or cloned microorganism such that the inserted regulatory element is operatively linked with the endogenous PGC-1β gene. For example, an endogenous PGC-1β gene which is normally "transcriptionally silent", i.e., a PGC-1β gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous PGC-1β gene may be activated by insertion of a promiscuous regulatory element that works across cell types.

A heterologous regulatory element may be inserted into a stable cell line or cloned microorganism, such that it is operatively linked with an endogenous PGC-1β gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated PGC-1β Proteins and Anti-PGC-1β Antibodies

One aspect of the invention pertains to isolated PGC-1β proteins, and biologically active portions thereof, as well as polypeptide fragments suitable for use as immunogens to raise anti-PGC-1β antibodies. In one embodiment, native PGC-1β proteins can be isolated from cells or tissue sources by an appropriate purification scheme using standard protein purification techniques. In another embodiment, PGC-1β proteins are produced by recombinant DNA techniques. Alternative to recombinant expression, a PGC-1β protein or polypeptide can be synthesized chemically using standard peptide synthesis techniques.

An "isolated" or "purified" protein or biologically active portion thereof is substantially free of cellular material or other contaminating proteins from the cell or tissue source from which the PGC-1β protein is derived, or substantially free from chemical precursors or other chemicals when chemically synthesized. The language "substantially free of cellular material" includes preparations of PGC-1β protein in which the protein is separated from cellular components of the cells from which it is isolated or recombinantly produced. In one embodiment, the language "substantially free of cellular material" includes preparations of PGC-1β protein having less than about 30% (by dry weight) of non-PGC-1β protein (also referred to herein as a "contaminating protein"), more preferably less than about 20% of non-PGC-1β protein, still more preferably less than about 10% of non-PGC-1β protein, and most preferably less than about 5% non-PGC-1β protein. When the PGC-1β protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PGC-1β protein in which the protein is separated from chemical precursors or other chemicals which are involved in the synthesis of the protein. In one embodiment, the language "substantially free of chemical precursors or other chemicals" includes preparations of PGC-1β protein having less than about 30% (by dry weight) of chemical precursors or non-PGC-1β chemicals, more preferably less than about 20% chemical precursors or non-PGC-1β chemicals, still more preferably less than about 10% chemical precursors or non-PGC-1β chemicals, and most preferably less than about 5% chemical precursors or non-PGC-1β chemicals.

As used herein, a "biologically active portion" of a PGC-1β protein includes a fragment of a PGC-1β protein which participates in an interaction between a PGC-1β molecule and a non-PGC-1β molecule. Biologically active portions of a PGC-1β protein include peptides comprising amino acid sequences sufficiently identical to or derived from the amino acid sequence of the PGC-1β protein, e.g., the amino acid sequence shown in SEQ ID NO:2 or 5, which include less amino acids than the full length PGC-1β proteins, and exhibit at least one activity of a PGC-1β protein. Typically, biologically active portions comprise a domain or motif with at least one activity of the PGC-1β protein, e.g., interaction with and/or coactivation of a nuclear receptor, and/or brown adipose cell differentiation. A biologically active portion of a PGC-1β protein can be a polypeptide which is, for example, 25, 50, 75, 100, 125, 150, 175, 200, 250, 300, 350, 400, 450, 500, 550, 600, 650, 700, 750, 800, 850, 900, 950, 1000 or more amino acids in length. Biologically active portions of a PGC-1β protein can be used as targets for developing agents which modulate a PGC-1β mediated activity, e.g., a transcriptional response.

It is to be understood that a preferred biologically active portion of a PGC-1β protein of the present invention may contain one or more of the following domains: an LXXLL motif, an RRM, an AD, an HBM, and/or a glutamic/aspartic acid rich acidic domain. Moreover, other biologically active portions, in which other regions of the protein are deleted, can be prepared by recombinant techniques and evaluated for one or more of the functional activities of a native PGC-1β protein.

In a preferred embodiment, the PGC-1β protein has an amino acid sequence shown in SEQ ID NO:2 or 5. In other embodiments, the PGC-1β protein is substantially identical to SEQ ID NO:2 or 5, and retains the functional activity of the protein of SEQ ID NO:2 or 5, yet differs in amino acid sequence due to natural allelic variation or mutagenesis, as described in detail in subsection I above. Accordingly, in another embodiment, the PGC-1β protein is a protein which comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to SEQ ID NO:2 or 5.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the mouse PGC-1β amino acid sequence of SEQ ID NO:2 having 1014 amino acid residues, at least 304, preferably at least 406, more preferably at least 507, even more preferably at least 608, and even more preferably at least 710, 811, 913 or more amino acid residues are aligned; when aligning a second sequence to the PGC-1β amino acid sequence of SEQ ID NO:5 having 1009 amino acid residues, at least 303, preferably at least 404, more preferably at least 505, even more preferably at least 605, and even more preferably at least 706, 807, 908 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online through the website of the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the website of the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers, E. and Miller, W. (*Comput. Appl. Biosci.* 4:11-17 (1988)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to PGC-1β nucleic acid molecules of the invention. BLAST protein searches can be performed with the XBLAST program, score=100, wordlength=3 to obtain amino acid sequences homologous to PGC-1β protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See the website of the National Center for Biotechnology Information.

The invention also provides PGC-1β chimeric or fusion proteins. As used herein, a PGC-1β "chimeric protein" or "fusion protein" comprises a PGC-1β polypeptide operatively linked to a non-PGC-1β polypeptide. An "PGC-1β polypeptide" refers to a polypeptide having an amino acid sequence corresponding to a PGC-1β molecule, whereas a "non-PGC-1β polypeptide" refers to a polypeptide having an amino acid sequence corresponding to a protein which is not substantially homologous to the PGC-1β protein, e.g., a protein which is different from the PGC-1β protein and which is derived from the same or a different organism. Within a PGC-1β fusion protein the PGC-1β polypeptide can correspond to all or a portion of a PGC-1β protein. In a preferred embodiment, a PGC-1β fusion protein comprises at least one biologically active portion of a PGC-1β protein. In another preferred embodiment, a PGC-1β fusion protein comprises at least two biologically active portions of a PGC-1β protein. Within the fusion protein, the term "operatively linked" is intended to indicate that the PGC-1β polypeptide and the non-PGC-1β polypeptide are fused in-frame to each other. The non-PGC-1β polypeptide can be fused to the N-terminus or C-terminus of the PGC-1β polypeptide.

For example, in one embodiment, the fusion protein is a GST-PGC-1β fusion protein in which the PGC-1β sequences are fused to the C-terminus of the GST sequences. Such fusion proteins can facilitate the purification of recombinant PGC-1β.

In another embodiment, the fusion protein is a PGC-1β protein containing a heterologous signal sequence at its N-terminus. In certain host cells (e.g., mammalian host cells), expression and/or secretion of PGC-1β can be increased through use of a heterologous signal sequence.

The PGC-1β fusion proteins of the invention can be incorporated into pharmaceutical compositions and administered to a subject in vivo. The PGC-1β fusion proteins can be used to affect the bioavailability of a PGC-1β target molecule. Use of PGC-1β fusion proteins may be useful therapeutically for the treatment of disorders caused by, for example, (i) aberrant modification or mutation of a gene encoding a PGC-1β protein; (ii) mis-regulation of the PGC-1β gene; and (iii) aberrant post-translational modification of a PGC-1β protein.

Moreover, the PGC-1β-fusion proteins of the invention can be used as immunogens to produce anti-PGC-1 antibodies in a subject, to purify PGC-1 P ligands and in screening assays to identify molecules which inhibit the interaction of PGC-1 P with a PGC-1 substrate.

Preferably, a PGC-1 P chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PGC-1β-encoding nucleic acid can be cloned into such an expression vector such that the fusion moiety is linked in-frame to the PGC-1β protein.

The present invention also pertains to variants of the PGC-1β proteins which function as either PGC-1β agonists (mimetics) or as PGC-1β antagonists. Variants of the PGC-1β proteins can be generated by mutagenesis, e.g., discrete point mutation or truncation of a PGC-1β protein. An agonist of the PGC-1β proteins can retain substantially the same, or a subset, of the biological activities of the naturally occurring form of a PGC-1β protein. An antagonist of a PGC-1β protein can inhibit one or more of the activities of the naturally occurring form of the PGC-1β protein by, for example, competitively modulating a PGC-1β-mediated activity of a PGC-1β protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PGC-1β protein.

In one embodiment, variants of a PGC-1β protein which function as either PGC-1β agonists (mimetics) or as PGC-1β antagonists can be identified by screening combinatorial libraries of mutants, e.g., truncation mutants, of a PGC-1β protein for PGC-1β protein agonist or antagonist activity. In one embodiment, a variegated library of PGC-1β variants is generated by combinatorial mutagenesis at the nucleic acid level and is encoded by a variegated gene library. A variegated library of PGC-1β variants can be produced by, for example, enzymatically ligating a mixture of synthetic oligonucleotides into gene sequences such that a degenerate set of potential PGC-1β sequences is expressible as individual polypeptides, or alternatively, as a set of larger fusion proteins (e.g., for phage display) containing the set of PGC-1β sequences therein. There are a variety of methods which can be used to produce libraries of potential PGC-1β variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1β sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477.

In addition, libraries of fragments of a PGC-1β protein coding sequence can be used to generate a variegated population of PGC-1β fragments for screening and subsequent selection of variants of a PGC-1β protein. In one embodiment, a library of coding sequence fragments can be generated by treating a double stranded PCR fragment of a PGC-1β coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1β protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1β proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1β variants (Arkin and Youvan (1992) *Proc. Natl. Acad. Sci. USA* 89:7811-7815; Delagrave et al. (1993) *Protein Eng.* 6(3):327-331).

In one embodiment, cell based assays can be exploited to analyze a variegated PGC-1β library. For example, a library of expression vectors can be transfected into a cell line, e.g., a brown adipose cell line such as HIB1B, which ordinarily responds to a PGC-1β target molecule in a particular PGC-1β target molecule-dependent manner. The transfected cells are then contacted with a PGC-1β target molecule and the effect of expression of the mutant on, e.g., on the transcriptional activity of PGC-1 P or the target molecule can be detected. Plasmid DNA can then be recovered from the cells which score for inhibition, or alternatively, potentiation of signaling by the PGC-1β target molecule, and the individual clones further characterized.

An isolated PGC-1β protein, or a portion or fragment thereof, can be used as an immunogen to generate antibodies that bind PGC-1β using standard techniques for polyclonal and monoclonal antibody preparation. A full-length PGC-1β protein can be used or, alternatively, the invention provides antigenic peptide fragments of PGC-1β for use as immunogens. The antigenic peptide of PGC-1β comprises at least 8 amino acid residues of the amino acid sequence shown in SEQ ID NO:2 or 5 and encompasses an epitope of PGC-1β such that an antibody raised against the peptide forms a specific immune complex with the PGC-1β protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PGC-1β that are located on the surface of the protein, e.g., hydrophilic regions, as well as regions with high antigenicity.

A PGC-1β immunogen typically is used to prepare antibodies by immunizing a suitable subject, (e.g., rabbit, goat, mouse or other mammal) with the immunogen. An appropriate immunogenic preparation can contain, for example, recombinantly expressed PGC-1β protein or a chemically synthesized PGC-1β polypeptide. The preparation can further include an adjuvant, such as Freund's complete or incomplete adjuvant, or similar immunostimulatory agent. Immunization of a suitable subject with an immunogenic PGC-1β preparation induces a polyclonal anti-PGC-1β antibody response.

Accordingly, another aspect of the invention pertains to anti-PGC-1β antibodies. The term "antibody" as used herein refers to immunoglobulin molecules and immunologically active portions of immunoglobulin molecules, i.e., molecules that contain an antigen binding site which specifically binds (immunoreacts with) an antigen, such as a PGC-1β. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PGC-1β molecules. The term "monoclonal antibody" or "monoclonal antibody composition", as used herein, refers to a population of antibody molecules that contain only one species of an antigen binding site capable of immunoreacting with a particular epitope of PGC-1β. A monoclonal antibody composition thus typically displays a single binding affinity for a particular PGC-1β protein with which it immunoreacts.

Polyclonal anti-PGC-1β antibodies can be prepared as described above by immunizing a suitable subject with a PGC-1β immunogen. The anti-PGC-1β antibody titer in the immunized subject can be monitored over time by standard techniques, such as with an enzyme linked immunosorbent assay (ELISA) using immobilized PGC-1β. If desired, the antibody molecules directed against PGC-1β can be isolated from the mammal (e.g., from the blood) and further purified by well known techniques, such as protein A chromatography to obtain the IgG fraction. At an appropriate time after immunization, e.g., when the anti-PGC-1β antibody titers are highest, antibody-producing cells can be obtained from the subject and used to prepare monoclonal antibodies by standard techniques, such as the hybridoma technique originally described by Kohler and Milstein (1975) *Nature* 256: 495-497) (see also, Brown et al. (1981) *J. Immunol.* 127: 539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with a PGC-1β immunogen as described above, and the culture supernatants of the resulting hybridoma cells are screened to identify a hybridoma producing a monoclonal antibody that binds PGC-1β.

Any of the many well known protocols used for fusing lymphocytes and immortalized cell lines can be applied for the purpose of generating an anti-PGC-1β monoclonal antibody (see, e.g., Galfre, G. et al. (1977) *Nature* 266:55052; Gefter et al. (1977) supra; Lerner (1981) supra; Kenneth (1980 supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1β, e.g., using a standard ELISA assay.

Alternative to preparing monoclonal antibody-secreting hybridomas, a monoclonal anti-PGC-1β antibody can be identified and isolated by screening a recombinant combinatorial immunoglobulin library (e.g., an antibody phage display library) with PGC-1β to thereby isolate immunoglobulin library members that bind PGC-1β. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348: 552-554.

Additionally, recombinant anti-PGC-1β antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PGC-1β antibody (e.g., monoclonal antibody) can be used to isolate PGC-1β by standard techniques, such as affinity chromatography or immunoprecipitation. An anti-PGC-1β antibody can facilitate the purification of natural PGC-1β from cells and of recombinantly produced PGC-1β expressed in host cells. Moreover, an anti-PGC-1β antibody can be used to detect PGC-1β protein (e.g., in a cellular lysate or cell supernatant) in order to evaluate the abundance and pattern of expression of the PGC-1β protein. Anti-PGC-1β antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a PGC-1β protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PGC-1β proteins, mutant forms of PGC-1β proteins, fusion proteins, and the like).

The recombinant expression vectors of the invention can be designed for expression of PGC-1β proteins in prokaryotic or eukaryotic cells. For example, PGC-1β proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PGC-1β activity assays, (e.g., direct assays or competitive assays described in detail below), or to generate antibodies specific for PGC-1β proteins, for example. In a preferred embodiment, a PGC-1β fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the PGC-1β expression vector is a yeast expression vector. Examples of vectors for expression in yeast *S. cerevisiae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (Invitrogen Corp, San Diego, Calif.).

Alternatively, PGC-1β proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1 987) *Genes Dev.* 1:268-277), lymphoid-specific promoters (Calame and Eaton (1988) *Adv. Immunol.* 43:23 5-275), in particular promoters of T cell receptors (Winoto and Baltimore (1 989) *EMBO J.* 8:729-733) and immunoglobulins (Baneiji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1β mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of anti sense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Anti sense RNA as a molecular tool for genetic analysis, *Reviews—Trends in Genetics*, Vol. 1(1) 1986.

Another aspect of the invention pertains to host cells into which a PGC-1β nucleic acid molecule of the invention is introduced, e.g., a PGC-1β nucleic acid molecule within a recombinant expression vector or a PGC-1β nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PGC-1β protein can be expressed in bacterial cells such as E. coli, insect cells, yeast or mammalian cells (such as Chinese hamster ovary cells (CHO), COS cells, BOSC cells, or HIB1B cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PGC-1β protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PGC-1β protein. Accordingly, the invention further provides methods for producing a PGC-1β protein using the host cells of the invention. In one embodiment, the method comprises culturing the host cell of the invention (into which a recombinant expression vector encoding a PGC-1β protein has been introduced) in a suitable medium such that a PGC-1β protein is produced. In another embodiment, the method further comprises isolating a PGC-1β protein from the medium or the host cell.

The host cells of the invention can also be used to produce non-human transgenic animals. For example, in one embodiment, a host cell of the invention is a fertilized oocyte or an embryonic stem cell into which PGC-1β-coding sequences have been introduced. Such host cells can then be used to create non-human transgenic animals in which exogenous PGC-1β sequences have been introduced into their genome or homologous recombinant animals in which endogenous PGC-1β sequences have been altered. Such animals are useful for studying the function and/or activity of a PGC-1β and for identifying and/or evaluating modulators of PGC-1β activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PGC-1β gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PGC-1β-encoding nucleic acid into the male pronuclei of a fertilized oocyte, e.g., by microinjection, retroviral infection, and allowing the oocyte to develop in a pseudopregnant female foster animal. The PGC-1β cDNA sequence of SEQ ID NO:1 or 4 can be introduced as a transgene into the genome of a non-human animal. Alternatively, a nonhuman homologue of a human PGC-1β gene, such as a rat PGC-1β gene, can be used as a transgene. Alternatively, a PGC-1β gene homologue, such as another PGC-1β family member, can be isolated based on hybridization to the PGC-1β cDNA sequences of SEQ ID NO:1, 3, 4, or 6, (described further in subsection I above) and used as a transgene. Intronic sequences and polyadenylation signals can also be included in the transgene to increase the efficiency of expression of the transgene. A tissue-specific regulatory sequence(s) can be operably linked to a PGC-1β transgene to direct expression of a PGC-1β protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a PGC-1β transgene in its genome and/or expression of PGC-1β mRNA in tissues or cells of the animals. A transgenic founder animal can then be used to breed additional animals carrying the transgene. Moreover, transgenic animals carrying a transgene encoding a PGC-1β protein can further be bred to other transgenic animals carrying other transgenes.

To create a homologous recombinant animal, a vector is prepared which contains at least a portion of a PGC-1β gene into which a deletion, addition or substitution has been introduced to thereby alter, e.g., functionally disrupt, the PGC-1β gene. The PGC-1β gene can be a human gene (e.g., the cDNA of SEQ ID NO:6), but more preferably, is the mouse gene of SEQ ID NO:3, or another non-human homologue of a human PGC-1β gene (e.g., a cDNA isolated by stringent hybridization with the nucleotide sequence of SEQ ID NO:1 or 4). For example, the mouse PGC-1β gene can be used to construct a homologous recombination nucleic acid molecule, e.g., a vector, suitable for altering an endogenous PGC-1β gene in the mouse genome. In a preferred embodiment, the homologous recombination nucleic acid molecule is designed such that, upon homologous recombination, the endogenous PGC-1β gene is functionally disrupted (i.e., no longer encodes a functional protein; also referred to as a "knock out" vector). Alternatively, the homologous recombination nucleic acid molecule can be designed such that, upon homologous recombination, the endogenous PGC-1β gene is mutated or otherwise altered but still encodes functional protein (e.g., the upstream regulatory region can be altered to thereby alter the expression of the endogenous PGC-1β protein). In the homologous recombination nucleic acid molecule, the altered portion of the PGC-1β gene is flanked at its 5' and 3' ends by additional nucleic acid sequence of the PGC-1β gene to allow for homologous recombination to occur between the exogenous PGC-1β gene carried by the homologous recombination nucleic acid molecule and an endogenous PGC-1β gene in a cell, e.g., an embryonic stem cell. The additional flanking PGC-1β nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced PGC-1β gene has homologously recombined with the endogenous PGC-1β gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Curr. Opin. Biotechnol.* 2:823-829 and in PCT International Publication Nos. WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The PGC-1β nucleic acid molecules, fragments of PGC-1β proteins, PGC-1β modulators, and anti-PGC-1β antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PGC-1β modulator, a fragment of a PGC-1β protein or an anti-PGC-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of PGC-1β activity is administered in combination with other agents (e.g., a small molecule), or in conjunction with another, complementary treatment regime. For example, in one embodiment, a modulator of PGC-1β activity is used to treat a metabolic disorder. Accordingly, modulation of PGC-1β activity may be used in conjunction with, for example, another agent used to treat the disorder (e.g., another agent used to treat diabetes, e.g., insulin, metformin, or a thiazoladinedione such as rosiglitizone or pioglitizone). In another embodiment, a modulator of PGC-1β activity is used to treat a neurodegenerative disorder. Accordingly, modulation of PGC-1β activity may be used in conjunction with, for example, another agent used to treat the disorder (e.g., another agent used to treat Parkinson's disease, e.g., tolcapone (Tasmar), or another COMT inhibitor or levodopa, levodopa/carbidopa, symmetrel, anticholinergics, selegiline or deprenyl (Eldepryl) or dopamine agonists).

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, small molecules, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a PGC-1β protein of the invention has one or more of the following activities: 1) it interacts with a nuclear receptor (e.g., HNF4α, PPARα, retinoic acid receptor α (RARα), thyroid hormone receptor β (TRβ), or glucocorticoid receptor (GR)); 2) it interacts with HCF; 3) it interacts with NRF1; 4) it interacts with a basal transcription factor; 5) it modulates the activity, e.g., the transcriptional activity, of a nuclear receptor and/or NRF1; 6) it modulates brown adipose cell determination and/or differentiation; 7) it modulates intra- or inter-cellular signaling; 8) it modulates viral infection (e.g., via interaction with HCF); 9) it modulates cellular proliferation; 10) it modulates metabolism; 11) it modulates mitochondrial activity and/or biogenesis; and 12) it modulates fatty acid β-oxidation.

The isolated nucleic acid molecules of the invention can be used, for example, to express PGC-1β protein (e.g., via a recombinant expression vector in a host cell in gene therapy applications), to detect PGC-1β mRNA (e.g., in a biological sample) or a genetic alteration in a PGC-1β gene, and to modulate PGC-1β activity, as described further below. The PGC-1β proteins can be used to treat disorders characterized by insufficient or excessive production of a PGC-1β target molecule or production of PGC-1β inhibitors. In addition, the PGC-1β proteins can be used to screen for naturally occurring PGC-1β target molecules, to screen for drugs or compounds which modulate PGC-1β activity, as well as to treat disorders characterized by insufficient or excessive production of PGC-1β protein or production of PGC-1β protein forms which have decreased, aberrant or unwanted activity compared to PGC-1β wild type protein (e.g., metabolic disorders, such as diabetes, insulin resistance, obesity, overweight, anorexia, and cachexia; cellular growth or differentiation disorders; and viral disorders). Moreover, the anti-PGC-1β antibodies of the invention can be used to detect and isolate PGC-1β proteins, regulate the bioavailability of PGC-1β proteins, and modulate PGC-1β activity.

A. Screening Assays:

The invention provides a method (also referred to herein as a "screening assay") for identifying modulators, e.g., candidate or test compounds or agents (e.g., peptides, peptidomimetics, small molecules or other drugs) which bind to PGC-1β proteins, have a stimulatory or inhibitory effect on, for example, PGC-1β expression or PGC-1β activity, or have a stimulatory or inhibitory effect on, for example, the expression or activity of a PGC-1β target molecule. The invention further provides a method (also referred to herein as a "screening assay") for identifying modulators, e.g., candidate or test compounds or agents (e.g., peptides, peptidomimetics, small molecules or other drugs) which modulate, e.g., upregulate or downregulated, the interaction between PGC-1α and HCF via the HCF binding motif (HBM). Those of skill in the art will appreciate that any of the following methods may be used to identify compounds which modulate the PGC-1α-HCF interaction in order to identify compounds which modulate cellular proliferation and/or viral infection. The nucleotide and amino acid sequences of mouse PGC-1α are set forth in SEQ ID NOs:8 and 9, respectively, and are described in U.S. Pat. No. 6,166,192; PCT International Publication No. WO 00/32215; Puigserver, P. et al. (1998) *Cell* 92(6):829-39, the contents of all of which are incorporated herein by reference. The nucleotide and amino acid sequences of human PGC-1α are set forth in SEQ ID NOs:10 and 111, respectively, and are described in PCT International Publication No. WO 00/32215.

In one embodiment, the invention provides assays for screening candidate or test compounds which are target molecules of a PGC-1β protein or polypeptide or biologically active portion thereof (e.g., nuclear receptors or other transcription factors). In another embodiment, the invention provides assays for screening candidate or test compounds which bind to or modulate the activity of a PGC-1β protein or polypeptide or biologically active portion thereof (e.g., cofactor or coenzyme analogs, or inhibitory molecules). The l0 test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.).

In one embodiment, an assay is a cell-based assay in which a cell which expresses a PGC-1β protein or biologically active portion thereof is contacted with a test compound and the ability of the test compound to modulate PGC-1β activity is determined. Determining the ability of the test compound to modulate PGC-1β activity can be accomplished by monitoring, for example, the interaction with and/or coactivation of a known target molecule (e.g., a nuclear receptor or HCF), by monitoring the autonomous transcriptional activity of PGC-1β, by monitoring the production of one or more specific metabolites in a cell which expresses PGC-1β (e.g., $^{14}C$ glucose), by monitoring expression of mitochondrial genes, or by monitoring mitochondrial content or function in the cell. The cell, for example, can be of mammalian origin, e.g., a brown adipose cell such as a HIB1B cell, a heart cell, or a liver cell.

The ability of the test compound to modulate PGC-1β binding to a target molecule (e.g., a nuclear receptor or HCF) can also be determined. Determining the ability of the test compound to modulate PGC-1β binding to a target molecule can be accomplished, for example, by coupling the PGC-1β target molecule with a radioisotope or enzymatic label such that binding of the PGC-1β target molecule to PGC-1β can be determined by detecting the labeled PGC-1β target molecule in a complex. Alternatively, PGC-1β could be coupled with a radioisotope or enzymatic label to monitor the ability of a test compound to modulate PGC-1β binding to a PGC-1β target molecule in a complex. Determining the ability of the test compound to bind PGC-1β can be accomplished, for example, by coupling the compound with a radioisotope or enzymatic label such that binding of the compound to PGC-1β can be determined by detecting the labeled PGC-1β compound in a complex. For example, compounds (e.g., PGC-1β target molecule, including small molecules) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PGC-1β target molecule) to interact with PGC-1β without the labeling of any of the interactants. For example, a microphysiometer can be used to detect the interaction of a compound with PGC-1β without the labeling of either the compound or the PGC-1β. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PGC-1β.

The ability of a test compound to modulate PGC-1β activity can be measured by contacting a cell, e.g., an undifferentiated HIB1B cell, and determining the ability of the compound to modulate differentiation of the cell into a brown adipose cell. The ability of a test compound to modulate PGC-1β activity can also be measured by contacting a cell (e.g., a brown adipose cell) with the test compound and measuring the number of mitochondria or the level of mitochondrial function in the cell as compared to a control cell not contacted with the test compound. The number of mitochondria can be measured, for example, by counting the mitochondria present in electron microscopy sections of the cell, or by analyzing the amount of mitochondrial DNA present in the cell, for example, by Southern blotting. Mitochondrial function can be determined by measuring expression levels of mitochondrial genes such as cytochrome c oxidase or by measuring oxygen consumption by the cell.

Exemplary methods for measuring mitochondrial function can further be found in: U.S. Pat. No. 6,166,192; PCT International Publication No. WO 00/32215; Puigserver, P. et al. (1998) *Cell* 92(6):829-39; Vidal-Puig, A. J. et al. (2000) *J. Biol. Chem*. 275(21):16258-66; and Wu, Z. et al. (1999) *Cell* 98(1):115-24, the entire contents of all of which are incorporated herein by reference.

The ability of a test compound to modulate insulin sensitivity of a cell can be determined by performing an assay in which a cell which express PGC-1β, e.g., a brown adipose cell such as a HIB1B cell, is contacted with the test compound, e.g., transformed to express the test compound; incubated with radioactively labeled glucose ($^{14}C$ glucose); and treated with insulin. An increase or decrease in glucose in the cells containing the test compound as compared to control cells indicates that the test compound can modulate insulin sensitivity of the cells. Alternatively, the cells containing the test compound can be incubated with a radioactively labeled phosphate source (e.g., [$^{32}P$]ATP) and treated with insulin. Phosphorylation of proteins in the insulin pathway, e.g., the insulin receptor, can then be measured. An increase or decrease in phosphorylation of a protein in the insulin pathway in cells containing the test compound as compared to the control cells indicates that the test compound can modulate insulin sensitivity of the cells.

In another embodiment, an assay is a cell-based assay comprising contacting a cell expressing a PGC-1β target molecule (e.g., a nuclear receptor or HCF) with a test compound and determining the ability of the test compound to modulate (e.g., stimulate or inhibit) the activity of the PGC-1β target molecule. Determining the ability of the test compound to modulate the activity of a PGC-1β target molecule can be accomplished, for example, by determining the ability of the PGC-1β protein to bind to or interact with the PGC-1β target molecule. Determining the ability of the test compound to modulate the activity of a PGC-1β target molecule can be accomplished, for example, by determining the transcriptional activity of the PGC-1β target molecule.

Determining the ability of the PGC-1β protein, or a biologically active fragment thereof, to bind to or interact with a PGC-1β target molecule can be accomplished by one of the methods described above for determining direct binding. In a preferred embodiment, determining the ability of the PGC-1β protein to bind to or interact with a PGC-1β target molecule can be accomplished by determining the activity of the target molecule. For example, the activity of the target molecule can be determined by detecting induction of a cellular response (i.e., changes in cellular proliferation, mitochondrial activity or content, or gluconeogenesis), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a PGC-1β protein or biologically active portion thereof is contacted with a test compound and the ability of the test compound to bind to the PGC-1β protein or biologically active portion thereof is determined. Preferred biologically active portions of the PGC-1β proteins to be used in assays of the present invention include fragments which participate in interactions with non-PGC-1β molecules, e.g., fragments with high surface probability scores. Binding of the test compound to the PGC-1β protein can be determined either directly or indirectly as described above. In a preferred embodiment, the assay includes contacting the PGC-1β protein or biologically active portion thereof with a known compound which binds PGC-1β to form an assay mixture, contacting the assay mixture with a test compound, and determining the ability of the test compound to interact with a PGC-1β protein, wherein determining the ability of the test compound to interact with a PGC-1β protein comprises determining the ability of the test compound to preferentially bind to PGC-1β or biologically active portion thereof as compared to the known compound.

In another embodiment, the assay is a cell-free assay in which a PGC-1β protein or biologically active portion thereof is contacted with a test compound and the ability of the test compound to modulate (e.g., stimulate or inhibit) the activity of the PGC-1β protein or biologically active portion thereof is determined. Determining the ability of the test compound to modulate the activity of a PGC-1β protein can be accomplished, for example, by determining the ability of the PGC-1β protein to bind to a PGC-1β target molecule by one of the methods described above for determining direct binding. Determining the ability of the PGC-1β protein to bind to a PGC-1β target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PGC-1β protein can be accomplished by determining the ability of the PGC-1β protein to further modulate the activity of a downstream effector of a PGC-1β target molecule. For example, the activity of the effector molecule on an appropriate target can be determined or the binding of the effector to an appropriate target can be determined as previously described.

In yet another embodiment, the cell-free assay involves contacting a PGC-1β protein or biologically active portion thereof with a known compound which binds the PGC-1β protein to form an assay mixture, contacting the assay mixture with a test compound, and determining the ability of the test compound to interact with the PGC-1β protein, wherein determining the ability of the test compound to interact with the PGC-1β protein comprises determining the ability of the PGC-1β protein to preferentially bind to or catalyze the transfer of a hydride moiety to or from the target substrate.

In more than one embodiment of the above assay methods of the present invention, it may be desirable to immobilize either PGC-1β or its target molecule to facilitate separation of complexed from uncomplexed forms of one or both of the proteins, as well as to accommodate automation of the assay. Binding of a test compound to a PGC-1β protein, or interaction of a PGC-1β protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PGC-1β fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PGC-1β protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PGC-1β binding or activity determined using standard techniques.

Other techniques for immobilizing proteins on matrices can also be used in the screening assays of the invention. For example, either a PGC-1β protein or a PGC-1β target molecule can be immobilized utilizing conjugation of biotin and streptavidin. Biotinylated PGC-1β protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1β protein or target molecules but which do not interfere with binding of the PGC-1β protein to its target molecule can be derivatized to the wells of the plate, and unbound target or PGC-1β protein trapped in the wells by antibody conjugation. Methods for detecting such complexes, in addition to those described above for the GST-immobilized complexes, include immunodetection of complexes using antibodies reactive with the PGC-1β protein or target molecule, as well as enzyme-linked assays which rely on detecting an enzymatic activity associated with the PGC-1β protein or target molecule.

In another embodiment, modulators of PGC-1β expression are identified in a method wherein a cell is contacted with a candidate compound and the expression of PGC-1β mRNA or protein in the cell is determined. The level of expression of PGC-1β mRNA or protein in the presence of the candidate compound is compared to the level of expression of PGC-1β mRNA or protein in the absence of the candidate compound. The candidate compound can then be identified as a modulator of PGC-1β expression based on this comparison. For example, when expression of PGC-1β mRNA or protein is greater (statistically significantly greater) in the presence of the candidate compound than in its absence, the candidate compound is identified as a stimulator of PGC-1β mRNA or protein expression. Alternatively, when expression of PGC-1β mRNA or protein is less (statistically significantly less) in the presence of the candidate compound than in its absence, the candidate compound is identified as an inhibitor of PGC-1β mRNA or protein expression. The level of PGC-1β mRNA or protein expression in the cells can be determined by methods described herein for detecting PGC-1β mRNA or protein.

In yet another aspect of the invention, the PGC-1β proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with PGC-1β ("PGC-1β-binding proteins" or "PGC-1β-bp") and are involved in PGC-1β activity. Such PGC-1β-binding proteins are also likely to be involved in the propagation of signals by the PGC-1β proteins or PGC-1β targets as, for example, downstream elements of a PGC-1β-mediated signaling pathway.

Alternatively, such PGC-1β-binding proteins are likely to be PGC-1β inhibitors.

The two-hybrid system is based on the modular nature of most transcription factors, which consist of separable DNA-binding and activation domains. Briefly, the assay utilizes two different DNA constructs. In one construct, the gene that codes for a PGC-1β protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PGC-1β-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PGC-1β protein.

In another aspect, the invention pertains to a combination of two or more of the assays described herein. For example, a modulating agent can be identified using a cell-based or a cell free assay, and the ability of the agent to modulate the activity of a PGC-1β protein can be confirmed in vivo, e.g., in an animal such as an animal model for in an animal such as an animal model for obesity, diabetes, anorexia, or cachexia. Examples of animals that can be used include the transgenic mouse described in U.S. Pat. No. 5,932,779 that contains a mutation in an endogenous melanocortin-4-receptor (MC4-R) gene; animals having mutations which lead to syndromes that include obesity symptoms (described in, for example, Friedman, J. M. et al. (1991) *Mamm. Genome* 1:130-144; Friedman, J. M. and Liebel, R. L. (1992) *Cell* 69:217-220; Bray, G. A. (1992) *Prog. Brain Res.* 93:333-341; and Bray, G. A. (1989) *Amer. J. Clin. Nutr.* 5:891-902); the animals described in Stubdal H. et al. (2000) *Mol. Cell Biol.* 20(3):878-82 (the mouse tubby phenotype characterized by maturity-onset obesity); the animals described in Abadie J. M. et al. *Lipids* (2000) 35(6):613-20 (the obese Zucker rat (ZR), a genetic model of human youth-onset obesity and type 2 diabetes mellitus); the animals described in Shaughnessy S. et al. (2000) *Diabetes* 49(6):904-11 (mice null for the adipocyte fatty acid binding protein); or the animals described in Loskutoff D. J. et al. (2000) *Ann. N. Y Acad. Sci.* 902:272-81 (the fat mouse). Other examples of animals that may be used include non-recombinant, non-genetic animal models of obesity such as, for example, rabbit, mouse, or rat models in which the animal has been exposed to either prolonged cold or long-term over-eating, thereby, inducing hypertrophy of BAT and increasing BAT thermogenesis (Himms-Hagen, J. (1990), supra). Additionally, animals created by ablation of BAT through use of targeted expression of a toxin gene (Lowell, B. et al. (1993) *Nature* 366:740-742) may be used. Animals deficient in PGC-1 (e.g., PGC-1 knockout mice) may be deficient in the ability to induce thermogenesis and therefore may be useful in determining whether a test compound can induce thermogenesis by bypassing PGC-1 and directly modulating the activity of DHDR-2.

In another embodiment of the invention, the ability of the agent to modulate the activity of a PGC-1β protein can be tested in an animal such as an animal model for a cellular proliferation disorder, e.g., tumorigenesis. Animal based models for studying tumorigenesis in vivo are well known in the art (reviewed in Animal Models of Cancer Predisposition Syndromes, Hiai, H. and Hino, O. (eds.) 1999, *Progress in Experimental Tumor Research*, Vol. 35; Clarke, A. R. (2000) *Carcinogenesis* 21:435-41) and include, for example, carcinogen-induced tumors (Rithidech, K. et al. (1999) *Mutat. Res.* 428:33-39; Miller, M. L. et al. (2000) *Environ. Mol. Mutagen.* 35:319-327), injection and/or transplantation of tumor cells into an animal, as well as animals bearing mutations in growth regulatory genes, for example, oncogenes (e.g., ras) (Arbeit, J. M. et al. (1993) *Am. J. Pathol.* 142:1187-1197; Sinn, E. et al. (1987) *Cell* 49:465-475; Thorgeirsson, S S et al. *Toxicol Lett* (2000) 112-113:553-555) and tumor suppressor genes (e.g., p53) (Vooijs, M. et al. (1999) *Oncogene* 18:5293-5303; Clark A. R. (1995) *Cancer Metast. Rev.* 14:125-148; Kumar, T. R. et al. (1995) *J. Intern. Med.* 238:233-238; Donehower, L. A. et al. (1992) *Nature* 356215-221). Furthermore, experimental model systems are available for the study of, for example, ovarian cancer (Hamilton, T. C. et al. (1984) *Semin. Oncol.* 11:285-298; Rahman, N. A. et al. (1998) *Mol. Cell. Endocrinol.* 145:167-174; Beamer, W. G. et al. (1998) *Toxicol. Pathol.* 26:704-710), gastric cancer (Thompson, J. et al. (2000) *Int. J. Cancer* 86:863-869; Fodde, R. et al. (1999) *Cytogenet. Cell Genet.* 86:105-111), breast cancer (Li, M. et al. (2000) *Oncogene* 19:1010-1019; Green, J. E. et al. (2000) *Oncogene* 19:1020-1027), melanoma (Satyamoorthy, K. et al. (1999) *Cancer Metast. Rev.* 18:401-405), and prostate cancer (Shirai, T. et al. (2000) *Mutat. Res.* 462:219-226; Bostwick, D. G. et al. (2000) *Prostate* 43:286-294). Animal based models for studying Parkinson's disease are also well known in the art (Dawson et al., Neuron. Jul. 18, 2002;35 (2):219-22)

This invention further pertains to novel agents identified by the above-described screening assays. Accordingly, it is within the scope of this invention to further use an agent identified as described herein in an appropriate animal model, as described above. For example, an agent identified as described herein (e.g., a PGC-1β modulating agent, an antisense PGC-1β nucleic acid molecule, a PGC-1β-specific antibody, or a PGC-1β-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PGC-1β nucleotide sequences, described herein, can be used to map the location of the PGC-1β genes on a chromosome. The mapping of the PGC-1β sequences to chromosomes is an important first step in correlating these sequences with genes associated with disease.

Briefly, PGC-1β genes can be mapped to chromosomes by preparing PCR primers (preferably 15-25 bp in length) from the PGC-1β nucleotide sequences. Computer analysis of the PGC-1β sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PGC-1β sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio P. et al. (1983) *Science* 220: 919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PGC-1β nucleotide sequences to design oligonucleotide primers, sublocalization can be achieved with panels of fragments from specific chromosomes. Other mapping strategies which can similarly be used to map a PGC-1β sequence to its chromosome include in situ hybridization (described in Fan, Y. et al. (1990) *Proc. Natl. Acad. Sci. USA* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature* 325:783-787.

Moreover, differences in the DNA sequences between individuals affected and unaffected with a disease associated with the PGC-1β gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PGC-1β sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PGC-1β nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PGC-1β nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 4 can comfortably provide positive individual identification with a panel of perhaps 10 to 1,000 primers which each yield a noncoding amplified sequence of 100 bases. If predicted coding sequences, such as those in SEQ ID NO:3 or 6 are used, a more appropriate number of primers for positive individual identification would be 500-2,000.

If a panel of reagents from PGC-1β nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of PGC-1β Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or 4 are particularly appropriate for this use as greater numbers of polymorphisms occur in the noncoding regions, making it easier to differentiate individuals using this technique. Examples of polynucleotide reagents include the PGC-1β nucleotide sequences or portions thereof, e.g., fragments derived from the noncoding regions of SEQ ID NO:1 or 4 having a length of at least 20 bases, preferably at least 30 bases.

The PGC-1β nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such PGC-1β probes can be used to identify tissue by species and/or by organ type.

In a similar fashion, these reagents, e.g., PGC-1β primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PGC-1β protein and/or nucleic acid expression as well as PGC-1β activity, in the context of a biological sample (e.g., blood, serum, cells, ascites, tissue) to thereby determine whether an individual is afflicted with a disease or disorder, or is at risk of developing a disorder, associated with aberrant or unwanted PGC-1β expression or activity (e.g., a metabolic disorder or a cellular proliferation disorder). The invention also provides for prognostic (or predictive) assays for determining whether an individual is at risk of developing a disorder associated with PGC-1β protein, nucleic acid expression or activity. For example, mutations in a PGC-1β gene can be assayed in a biological sample. Such assays can be used for prognostic or predictive purpose to thereby prophylactically treat an individual prior to the onset of a disorder characterized by or associated with PGC-1β protein, nucleic acid expression or activity.

Another aspect of the invention pertains to monitoring the influence of agents (e.g., drugs, compounds) on the expression or activity of PGC-1β in clinical trials.

These and other agents are described in further detail in the following sections.

1. Diagnostic Assays

An exemplary method for detecting the presence or absence of PGC-1β protein or nucleic acid in a biological sample involves obtaining a biological sample from a test subject and contacting the biological sample with a compound or an agent capable of detecting PGC-1β protein or nucleic acid (e.g., mRNA, or genomic DNA) that encodes PGC-1β protein such that the presence of PGC-1β protein or nucleic acid is detected in the biological sample. A preferred agent for detecting PGC-1β mRNA or genomic DNA is a labeled nucleic acid probe capable of hybridizing to PGC-1β mRNA or genomic DNA. The nucleic acid probe can be, for example, the PGC-1β nucleic acid set forth in SEQ ID NO:1, 3, 4, or 6, or a portion thereof, such as an oligonucleotide of at least 15, 30, 50, 100, 250 or 500 nucleotides in length and sufficient to specifically hybridize under stringent conditions to PGC-1β mRNA or genomic DNA. Other suitable probes for use in the diagnostic assays of the invention are described herein.

A preferred agent for detecting PGC-1β protein is an antibody capable of binding to PGC-1β protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PGC-1β mRNA, protein, or genomic DNA in a biological sample in vitro as well as in vivo. For example, in vitro techniques for detection of PGC-1β mRNA include Northern hybridizations and in situ hybridizations. In vitro techniques for detection of PGC-1β protein include enzyme linked immunosorbent assays (ELISAs), Western blots, immunoprecipitations and immunofluorescence. In vitro techniques for detection of PGC-1β genomic DNA include Southern hybridizations. Furthermore, in vivo techniques for detection of PGC-1β protein include introducing into a subject a labeled anti-PGC-1β antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PGC-1β protein, mRNA, or genomic DNA, such that the presence of PGC-1β protein, mRNA or genomic DNA is detected in the biological sample, and comparing the presence of PGC-1β protein, mRNA or genomic DNA in the control sample with the presence of PGC-1β protein, mRNA or genomic DNA in the test sample.

The invention also encompasses kits for detecting the presence of PGC-1β in a biological sample. For example, the kit can comprise a labeled compound or agent capable of detecting PGC-1β protein or mRNA in a biological sample; means for determining the amount of PGC-1β in the sample; and means for comparing the amount of PGC-1β in the sample with a standard. The compound or agent can be packaged in a suitable container. The kit can further comprise instructions for using the kit to detect PGC-1β protein or nucleic acid.

2. Prognostic Assays

The diagnostic methods described herein can furthermore be utilized to identify subjects having or at risk of developing a disease or disorder associated with aberrant or unwanted PGC-1β expression or activity (e.g., a metabolic disorder or a cellular proliferation disorder). As used herein, the term "aberrant" includes a PGC-1β expression or activity which deviates from the wild type PGC-1β expression or activity. Aberrant expression or activity includes increased or decreased expression or activity, as well as expression or activity which does not follow the wild type developmental pattern of expression or the subcellular pattern of expression. For example, aberrant PGC-1β expression or activity is intended to include the cases in which a mutation in the PGC-1β gene causes the PGC-1β gene to be under-expressed or over-expressed and situations in which such mutations result in a non-functional PGC-1β protein or a protein which does not function in a wild-type fashion, e.g., a protein which does not interact with a PGC-1β target molecule, or one which interacts with a non-PGC-1β target molecule. As used herein, the term "unwanted" includes an unwanted phenomenon involved in a biological response such as cellular proliferation. For example, the term unwanted includes a PGC-1β expression or activity which is undesirable in a subject.

The assays described herein, such as the preceding diagnostic assays or the following assays, can be utilized to identify a subject having or at risk of developing a disorder associated with a misregulation in PGC-1β protein activity or nucleic acid expression, such as a metabolic disorder or a cellular proliferation disorder. Alternatively, the prognostic assays can be utilized to identify a subject having or at risk for developing a disorder associated with a misregulation in PGC-1β protein activity or nucleic acid expression, such as a metabolic disorder or a cellular proliferation disorder. Thus, the present invention provides a method for identifying a disease or disorder associated with aberrant or unwanted PGC-1β expression or activity in which a test sample is obtained from a subject and PGC-1β protein or nucleic acid (e.g., mRNA or genomic DNA) is detected, wherein the presence of PGC-1β protein or nucleic acid is diagnostic for a subject having or at risk of developing a disease or disorder associated with aberrant or unwanted PGC-1β expression or activity. As used herein, a "test sample" refers to a biological sample obtained from a subject of interest. For example, a test sample can be a biological fluid (e.g., blood, ascites, cerebrospinal fluid, or serum), cell sample, or tissue sample (e.g., a fat, heart, or liver sample).

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted PGC-1β expression or activity. For example, such methods can be used to determine whether a subject can be effectively treated with an agent for a metabolic disorder or a cellular proliferation disorder. Thus, the present invention provides methods for determining whether a subject can be effectively treated with an agent for a disorder associated with aberrant or unwanted PGC-1β expression or activity in which a test sample is obtained and PGC-1β protein or nucleic acid expression or activity is detected (e.g., wherein the abundance of PGC-1β protein or nucleic acid expression or activity is diagnostic for a subject that can be administered the agent to treat a disorder associated with aberrant or unwanted PGC-1β expression or activity).

The methods of the invention can also be used to detect genetic alterations in a PGC-1β gene, thereby determining if a subject with the altered gene is at risk for a disorder characterized by misregulation in PGC-1β protein activity or nucleic acid expression, such as a metabolic disorder or a cellular proliferation disorder. In preferred embodiments, the methods include detecting, in a sample of cells from the subject, the presence or absence of a genetic alteration characterized by at least one of an alteration affecting the integrity of a gene encoding a PGC-1β-protein, or the mis-expression of the PGC-1β gene. For example, such genetic alterations can be detected by ascertaining the existence of at least one of 1) a deletion of one or more nucleotides from a PGC-1β gene; 2) an addition of one or more nucleotides to a PGC-1β gene; 3) a substitution of one or more nucleotides of a PGC-1β gene, 4) a chromosomal rearrangement of a PGC-1β gene; 5) an alteration in the level of a messenger RNA transcript of a PGC-1β gene, 6) aberrant modification of a PGC-1β gene, such as of the methylation pattern of the genomic DNA, 7) the presence of a non-wild type splicing pattern of a messenger RNA transcript of a PGC-1β gene, 8) a non-wild type level of a PGC-1β-protein, 9) allelic loss of a PGC-1β gene, and 10) inappropriate post-translational modification of a PGC-1β-protein. As described herein, there are a large number of assays known in the art which can be used for detecting alterations in a PGC-1β gene. A preferred biological sample is a tissue (e.g., a fat, heart, or liver sample), blood, or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a PGC-1β gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a PGC-1β gene under conditions such that hybridization and amplification of the PGC-1β gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PGC-1β gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PGC-1β can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244-255; Kozal, M. J. et al. (1996) *Nat. Med.* 2:753-759). For example, genetic mutations in PGC-1β can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PGC-1β gene and detect mutations by comparing the sequence of the sample PGC-1β with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the PGC-1β gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type PGC-1β sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PGC-1β cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a PGC-1β sequence, e.g., a wild-type PGC-1β sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PGC-1β genes. For example, single strand conformation polymorphism (SSCP) may be used to detect differences in electrophoretic mobility between mutant and wild type nucleic acids (Orita et al. (1989) *Proc Natl. Acad. Sci USA*:86:2766, see also Cotton (1993) *Mutat. Res.* 285:125-144; and Hayashi (1992) *Genet. Anal. Tech. Appl.* 9:73-79). Single-stranded DNA fragments of sample and control PGC-1β nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in l0 the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PGC-1β gene.

Furthermore, any cell type or tissue in which PGC-1β is expressed may be utilized in the prognostic assays described herein.

3. Monitoring of Effects During Clinical Trials

Monitoring the influence of agents (e.g., drugs) on the expression or activity of a PGC-1β protein (e.g., the modulation of brown adipose differentiation, metabolism, and/or cellular proliferation) can be applied not only in basic drug screening, but also in clinical trials. For example, the effectiveness of an agent determined by a screening assay as described herein to increase PGC-1β gene expression, protein levels, or upregulate PGC-1β activity, can be monitored in clinical trials of subjects exhibiting decreased PGC-1β gene expression, protein levels, or downregulated PGC-1β activity. Alternatively, the effectiveness of an agent determined by a screening assay to decrease PGC-1β gene expression, protein levels, or downregulate PGC-1β activity, can be monitored in clinical trials of subjects exhibiting increased PGC-1β gene expression, protein levels, or upregulated PGC-1β activity. In such clinical trials, the expression or activity of a PGC-1β gene, and preferably, other genes that have been implicated in, for example, a PGC-1β-associated disorder can be used as a "read out" or markers of the phenotype of a particular cell.

For example, and not by way of limitation, genes, including PGC-1β, that are modulated in cells by treatment with an agent (e.g., compound, drug or small molecule) which modulates PGC-1β activity (e.g., identified in a screening assay as described herein) can be identified. Thus, to study the effect of agents on PGC-1β-associated disorders (e.g., disorders characterized by deregulated brown adipose differentiation, gluconeogenesis, and/or cell proliferation), for example, in a clinical trial, cells can be isolated and RNA prepared and analyzed for the levels of expression of PGC-1β and other genes implicated in the PGC-1β-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PGC-1β or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a PGC-1β protein, mRNA, or genomic DNA in the preadministration sample; (iii) obtaining one or more post-administration samples from the subject; (iv) detecting the level of expression or activity of the PGC-1β protein, mRNA, or genomic DNA in the post-administration samples; (v) comparing the level of expression or activity of the PGC-1β protein, mRNA, or genomic DNA in the pre-administration sample with the PGC-1β protein, mRNA, or genomic DNA in the post administration sample or samples; and (vi) altering the administration of the agent to the subject accordingly. For example, increased administration of the agent may be desirable to increase the expression or activity of PGC-1β to higher levels than detected, i.e., to increase the effectiveness of the agent. Alternatively, decreased administration of the agent may be desirable to decrease expression or activity of PGC-1β to lower levels than detected, i.e., to decrease the effectiveness of the agent. According to such an embodiment, PGC-1β expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted PGC-1β expression or activity, e.g., a metabolic disorder or a cellular proliferation disorder. As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the PGC-1β molecules of the present invention or PGC-1β modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted PGC-1β expression or activity, by administering to the subject a PGC-1β or an agent which modulates PGC-1β expression or at least one PGC-1β activity. Subjects at risk for a disease which is caused or contributed to by aberrant or unwanted PGC-1β expression or activity can be identified by, for example, any or a combination of diagnostic or prognostic assays as described herein. Administration of a prophylactic agent can occur prior to the manifestation of symptoms characteristic of the PGC-1β aberrancy, such that a disease or disorder is prevented or, alternatively, delayed in its progression. Depending on the type of PGC-1β aberrancy, for example, a PGC-1β, PGC-1β agonist or PGC-1β antagonist agent can be used for treating the subject. The appropriate agent can be determined based on screening assays described herein.

2. Therapeutic Methods

Another aspect of the invention pertains to methods of modulating PGC-1β expression or activity for therapeutic purposes. Accordingly, in an exemplary embodiment, the modulatory method of the invention involves contacting a cell with a PGC-1β or agent that modulates one or more of the activities of PGC-1β protein activity associated with the cell. An agent that modulates PGC-1β protein activity can be an agent as described herein, such as a nucleic acid or a protein, a naturally-occurring target molecule of a PGC-1β protein (e.g., a nuclear receptor or HCF), a PGC-1β antibody, a PGC-1β agonist or antagonist, a peptidomimetic of a PGC-1β agonist or antagonist, or other small molecule. In one embodiment, the agent stimulates one or more PGC-1β activities. Examples of such stimulatory agents include active PGC-1β protein and a nucleic acid molecule encoding PGC-1β that has been introduced into the cell. In another embodiment, the agent inhibits one or more PGC-1β activities. Examples of such inhibitory agents include antisense PGC-1β nucleic acid molecules, anti-PGC-1β antibodies, and PGC-1β inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a PGC-1β protein or nucleic acid molecule. In one embodiment, the method involves administering an agent (e.g., an agent identified by a screening assay described herein), or combination of agents that modulates (e.g., upregulates or downregulates) PGC-1β expression or activity. In another embodiment, the method involves administering a PGC-1β protein or nucleic acid molecule as therapy to compensate for reduced, aberrant, or unwanted PGC-1β expression or activity.

Stimulation of PGC-1β activity is desirable in situations in which PGC-1β is abnormally downregulated and/or in which increased PGC-1β activity is likely to have a beneficial effect. Likewise, inhibition of PGC-1β activity is desirable in situations in which PGC-1β is abnormally upregulated and/or in which decreased PGC-1β activity is likely to have a beneficial effect.

3. Pharmacogenomics

The PGC-1β molecules of the present invention, as well as agents, or modulators which have a stimulatory or inhibitory effect on PGC-1β activity (e.g., PGC-1β gene expression) as identified by a screening assay described herein can be administered to individuals to treat (prophylactically or therapeutically) PGC-1β-associated disorders (e.g., metabolic disorders or a cellular proliferation disorders) associated with aberrant or unwanted PGC-1β activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PGC-1β molecule or PGC-1β modulator as well as tailoring the dosage and/or therapeutic regimen of treatment with a PGC-1β molecule or PGC-1β modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PGC-1β protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a PGC-1β molecule or PGC-1β modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PGC-1β molecule or PGC-1β modulator, such as a modulator identified by one of the exemplary screening assays described herein.

E. Electronic Apparatus Readable Media and Arrays

Electronic apparatus readable media comprising PGC-1β sequence information is also provided. As used herein, "PGC-1β sequence information" refers to any nucleotide and/or amino acid sequence information particular to the PGC-1β molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said PGC-1β sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon PGC-1β sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the PGC-1β sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the PGC-1β sequence information.

By providing PGC-1β sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a metabolic or cellular proliferation disease, disorder, or pre-disease condition or a pre-disposition to a metabolic or cellular proliferation disease, disorder, or pre-disease condition, wherein the method comprises the steps of determining PGC-1β sequence information associated with the subject and based on the PGC-1β sequence information, determining whether the subject has a metabolic or cellular proliferation disease, disorder, or pre-disease condition or a pre-disposition to a metabolic or cellular proliferation disease, disorder, or pre-disease condition, and/or recommending a particular treatment for the disease, disorder, or pre-disease condition.

The present invention further provides in an electronic system and/or in a network, a method for determining whether a subject has a metabolic or cellular proliferation disease, disorder, or pre-disease condition or a pre-disposition to a metabolic or cellular proliferation disease, disorder, or pre-disease condition wherein the method comprises the steps of determining PGC-1β sequence information associated with the subject, and based on the PGC-1β sequence information, determining whether the subject has a metabolic or cellular proliferation disease, disorder, or pre-disease condition or a pre-disposition to a metabolic or cellular proliferation disease, disorder, or pre-disease condition, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a metabolic or cellular proliferation disease, disorder, or pre-disease condition or a pre-disposition to a metabolic or cellular proliferation disease, disorder, or pre-disease condition, said method comprising the steps of receiving PGC-1β sequence information from the subject and/or information related thereto, receiving phenotypic information associated with the subject, acquiring information from the network corresponding to PGC-1β and/or a metabolic or cellular proliferation disease, disorder, or pre-disease condition, and based on one or more of the phenotypic information, the PGC-1β information (e.g., sequence information and/or information related thereto), and the acquired information, determining whether the subject has a metabolic or cellular proliferation disease, disorder, or pre-disease condition or a metabolic or cellular proliferation disease, disorder, or pre-disease condition. The method may further comprise the step of recommending a particular treatment for the disease, disorder or pre-disease condition.

The present invention also provides a business method for determining whether a subject has a metabolic or cellular proliferation disease, disorder, or pre-disease condition or a pre-disposition to a metabolic or cellular proliferation disease, disorder, or pre-disease condition, said method comprising the steps of receiving information related to PGC-1β (e.g., sequence information and/or information related thereto), receiving phenotypic information associated with the subject, acquiring information from the network related to PGC-1β and/or related to a metabolic or cellular proliferation disease, disorder, or pre-disease condition, and based on one or more of the phenotypic information, the PGC-1β information, and the acquired information, determining whether the subject has a metabolic or cellular proliferation disease, disorder, or pre-disease condition r or a pre-disposition to a metabolic or cellular proliferation disease, disorder, or pre-disease condition. The method may further comprise the step of recommending a particular treatment for the disease, disorder or pre-disease condition.

The invention also includes an array comprising a PGC-1β sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be PGC-1β. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a metabolic or cellular proliferation disease, disorder, or pre-disease condition, progression of a metabolic or cellular proliferation disease, disorder, or pre-disease condition, and processes, such a cellular transformation associated with the metabolic or cellular proliferation disease, disorder, or pre-disease condition.

The array is also useful for ascertaining the effect of the expression of a gene on the expression of other genes in the same cell or in different cells (e.g., ascertaining the effect of PGC-1β expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including PGC-1β) that could serve as a molecular target for diagnosis or therapeutic intervention.

This invention is further illustrated by the following examples which should not be construed as limiting. The contents of all references, patents, and published patent applications cited throughout this application, as well as the figures and the sequence listing, are incorporated herein by reference.

EXAMPLES

Materials and Methods

All experiments were performed using the mouse PGC-1β, unless otherwise noted.

Plasmid Construction

The full-length mouse PGC-1β cDNA clone was obtained by ligating the 5'end of the PGC-1β cDNA generated by GENERACER (Invitrogen, CA) to an EST cDNA clone (GenBank Accession No. AA288169) that contained the 3' end. The presence of PGC-1β transcript in vivo was confirmed by RT-PCR using primers located throughout the cDNA sequence. GST-PGC-1β (N350) was generated by inserting a PCR fragment coding for the N-terminal 350 amino acids of SEQ ID NO:2 in frame into pGEX-5×1 vector. Fusion constructs between GAL4-DBD and various regions of PGC-1β or HCF were generated by subcloning PCR-amplified cDNA fragments in frame into pCMX-Gal4 plasmid (Puigserver, P. et al. (1998) *Cell* 92:829-839). N-terminal Flag-tagged PGC-1β (amino acids 2-1014 of SEQ ID NO:2) was obtained by subcloning the cDNA insert into pCATCH Flag plasmid (Georgiev, O. et al. (1996) *Gene* 168:165-167). All PCR fragments were verified by sequencing.

Transient Transfection

BOSC cells and COS cells were maintained in Dulbecco's modified Eagle's medium (DMEM) plus 10% fetal bovine serum (FBS). The cells were transfected using FuGENE (Roche, Switzerland) according to manufacturer's instructions. In some experiments, ligands were added to the culture in DMEM plus 0.5% bovine serum albumin (BSA) at 50 nM for T3 or 1 μM for dexamethasone 24 hours after transfection. Luciferase assays were performed 24 hours after the addition of ligands.

RNA Expression Analysis

Total RNA was isolated from frozen mouse tissues using Trizol (Gibco, NJ). For cold exposure, C57/B16 mice were maintained at 4° C. for 6 hours before sacrifice. HIB1B cells were maintained in DMEM plus 10% cosmic calf serum. To induce differentiation, confluent cells were grown in DMEM plus 10% FBS, 1 μM dexamethasone, 50 nM T3, 50 nM insulin, and 0.5 mM Isobutylmethylxanthine (IBMX) for 48 hours. The differentiating cells were then maintained in DMEM plus 10% FBS, 50 nM T3 and 50 nM insulin. To induce UCP-1 expression, differentiated HIB1B cells were treated with 10 μM forskolin for 6 hours before RNA isolation. For RNA analysis, 20 μg of total RNA were separated by gel electrophoresis, transferred to a nylon membrane, and subsequently hybridized with specific probes for various genes.

Protein Interaction Studies

Binding assays were performed as described in Puigserver et al. (1998) supra. Briefly, glutathione beads containing approximately 1 μg of GST or GST-PGC-1α or PGC-1β fusion proteins were incubated with 5 μl of in vitro translated protein for 1 hour at room temperature in 250 μl binding buffer (20 mM HEPES, pH 7.9, 75 mM KCl, 0.1 mM EDTA, 2.5 mM $MgCl_2$, 0.05% NP40, 2 mM DTT, and 10% glycerol; TNT coupled transcription/translation system, Promega, WI). Ligands were included in some binding reactions as indicated. The beads were subsequently washed four times with binding buffer and resuspended in SDS-PAGE buffer. The samples were separated on a denaturing SDS gel that was dried prior to autoradiography.

For coimmunoprecipitation assays, BOSC cells were transiently transfected with various combinations of plasmids using FuGENE. After 36 hours of transfection, cells were lysed in IP buffer (100 mM Tris, pH 8.0, 250 mM NaCl, 1% NP40, 1 mM EDTA, 1 mM $MgCl_2$, and protease inhibitors), and the lysate was incubated with 10 μl anti-Flag sepharose beads (Sigma, MO) for 1 hour at room temperature. The beads were washed four times with IP buffer and resuspended in SDS-PAGE buffer. The samples were then processed for immunoblotting analysis.

Example 1

Identification and Characterization of Murine and Human PGC-1β cDNAs

In this example, the identification and characterization of the genes encoding mouse and human PGC-1β is described.

Isolation of the PGC-1β cDNA

The invention is based, at least in part, on the discovery of novel genes encoding novel proteins, referred to herein as PGC-1β. The N-terminus of mouse PGC-1α was used to search genomic and EST databases. A partial transcript in the Celera mouse genome database (Accession No. mCT4723), which encoded a novel protein sharing a high degree of sequence identity with PGC-1α, was designated PGC-1β. The full-length mouse PGC-1β cDNA sequence was obtained by ligating the 5' end of the cDNA generated by RACE to fragments derived from an EST clone (GenBank Accession No. AA288169). The murine PGC-1β is localized to chromosome 18 (FIG. 6).

The entire sequence of the 3.6 kb murine PGC-1β cDNA was determined and found to contain an open reading frame encoding a protein of 1014 amino acid residues. The murine cDNA sequence is set forth in FIGS. 1A-1B and in SEQ ID NO:1. The amino acid sequence of the murine PGC-1β is set forth in FIG. 2 and in SEQ ID NO:2. The coding region (open reading frame) of SEQ ID NO:1 is set forth as SEQ ID NO:3. The human PGC-1β was identified in the publicly available sequence database of the Human Genome Project (GenBank Accession No. NT_023152) based on homology to the mouse PGC-1β sequence. The entire sequence of the human PGC-1β cDNA was determined and found to contain an open reading frame encoding a protein of 1009 amino acid residues. The human cDNA sequence is set forth in FIGS. 3A-3B and in SEQ ID NO:4. The amino acid sequence of the human PGC-1β is set forth in FIG. 4 and in SEQ ID NO:5.

Figure 6:
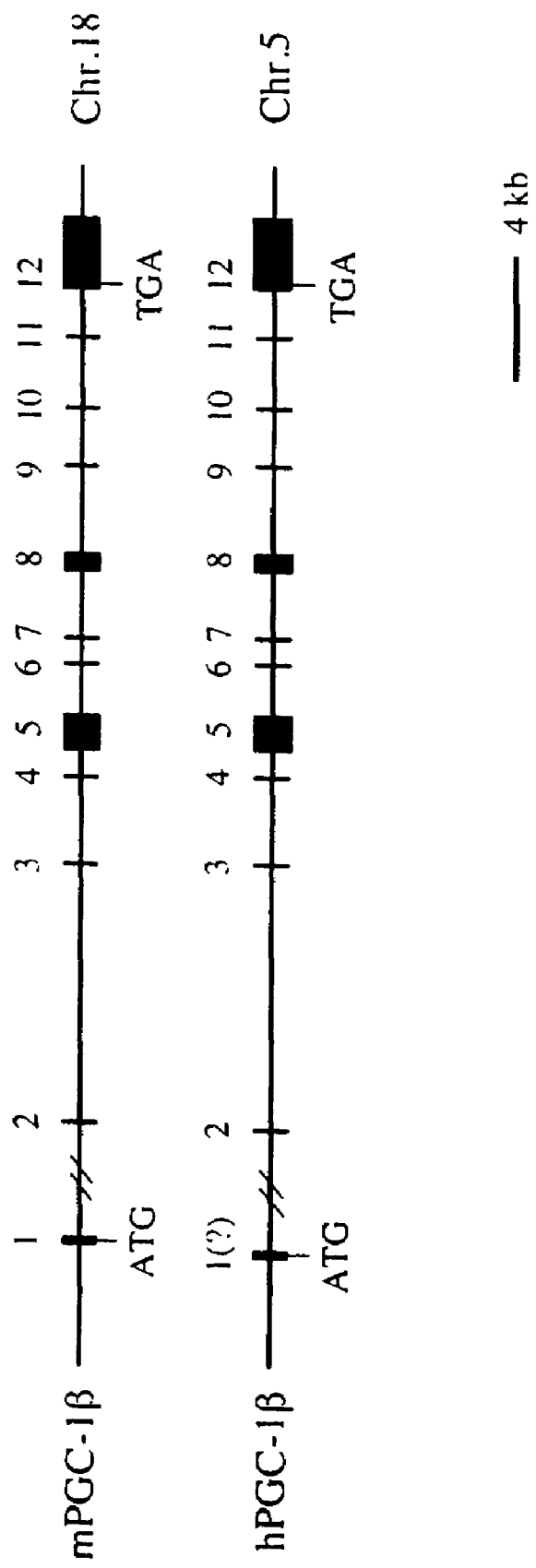
FIG. 6 depicts a schematic diagram of the genomic structure and chromosomal localization of the murine and human PGC-1β genes.

The human PGC-1β protein of SEQ ID NO:5, which is about 70% identical to the murine PGC-1β protein of SEQ ID NO:2, is localized to the chromosomal region 5q33 (FIG. 6). BLAST searches revealed that the PGC-1 family is well conserved in other species such as chicken (GenBank Accession No. BG709977), zebrafish (GenBank Accession No. AI477804), and *Xenopus* (GenBank Accession Nos. BI448917 and BI448253).

Analysis of the PGC-1β Molecules

Sequence analysis revealed that the mouse PGC-1β protein has similarity to PGC-1α over the entire length of the molecule, including three LXXLL motifs at the N-terminus and one RNA recognition motif (RRM) at the C-terminus (see FIGS. 2 and 5). The human PGC-1β has a similar structure, but has only two LXXLL motifs (see FIG. 4). The identity between mouse PGC-1α and mouse PGC-1β is especially high in the N-terminal activation domain (40% identical) and the C-terminal RNA-binding domain (48% identical), as shown in FIG. 5.

Sequence comparison of all PGC-1 family members, including PGC-1 Related Coactivator (PRC) (Andersson, U. and Scarpulla, R. C. (2001) *Mol. Cell. Biol.* 21(11):3738-49) revealed a novel conserved region containing a tetrapeptide motif (DHDY; SEQ ID NO:7), located at about residues 683-686 of SEQ ID NO:2, and at about residues 677-680 of SEQ ID NO:5, that has been previously identified in other proteins as a putative binding site for host cell factor (HCF), a protein involved in the regulation of cell cycle progression and the assembly of a multiprotein transcriptional complex during herpes simplex virus (HSV) infection (Freiman, R. N. and Herr, W. (1997) *Genes Dev.* 11:3122-3127; Andersson, U. and Scarpulla, R. C. (2001) *Mol. Cell. Biol.* 21:3738-3749). Analysis of the PGC-1β amino acid sequence further resulted in the identification of two glutamic/aspartic acid rich acidic domains. However unlike PGC-1α, PGC-1β lacks most of the arginine/serine rich domain (RS), a region that has been implicated in the regulation of RNA processing (Monsalve, M et al. (2000) *Mol. Cell* 6:307-316).

Example 2

Analysis of Murine PGC-1β Expression Patterns

Northern hybridization analysis revealed that PGC-1β is expressed in a highly tissue selective manner. PGC-1β mRNA is most abundantly present in brown adipose tissue (BAT), heart and brain, all tissues notable for containing very high concentrations of mitochondria. These results strongly suggest that PGC-1β may play an important role in mitochondrial function, respiration, and/or thermogenesis. Two predominant species of PGC-1β mRNA (5 kb and 9 kb) were detected, which may be the result of the use of two alternative polyadenylation signals present in the 3' end of the PGC-1β gene. Moderate levels of PGC-1β mRNA were also observed in skeletal muscle, liver, and white adipose tissue (WAT). The difference in mRNA abundance between BAT and WAT was more than 10-fold.

PGC-1α was initially identified as a transcriptional coactivator that controls mitochondrial biogenesis and adaptive thermogenesis in skeletal muscle and brown fat. In contrast to the cold-inducible expression of PGC-1α, the expression of PGC-1β in BAT is not increased in response to cold exposure. Given its abundant expression in BAT, it was hypothesized that PGC-1β might be involved in the determination and/or differentiation of brown adipocytes. To test whether PGC-1β is regulated during BAT differentiation, the mouse brown fat cell line HIB1B was induced to undergo differentiation and examined for PGC-1β expression. Compared to undifferentiated cells, the expression of PGC-1β is upregulated on days 3 and 5 of differentiation, parallel with a concomitant downregulation in PGC-1α expression. Upon treatment with forskolin, an activator of adenylyl cyclase, PGC-1α expression is rapidly induced, along with the key uncoupling protein of brown fat, UCP1 (Klaus, S. et al. (1994) *J. Cell Sci.* 107:313-319). In contrast, PGC-1β expression is slightly decreased. These results indicate that PGC-1α and PGC-1β are likely to perform distinct roles in brown fat regulation and the regulation of other brown fat functions such as adaptive thermogenesis.

PGC-1α expression is highly induced in the liver during fasting, and it has been shown to play a direct role in the activation of hepatic gluconeogenesis in cultured primary hepatocytes and in rats (Yoon, J. C. et al. (2001) *Nature* 413:131-138; Herzig, S. et al. (2001) *Nature* 413:179-183). Elevated expression of PGC-1α has also been shown in models of both type-1 and type-2 diabetes (Yoon et al. (2001) supra). The expression of PGC-1β is significantly increased in the liver during fasting, a pattern that is strikingly similar to the regulation of PGC-1α expression. These results suggest that PGC-1β may be part of the regulatory pathways that activate the hepatic adaptation during fasting, such as the elevation of gluconeogenesis, β-oxidation of fatty acids and ketogenesis.

Figure 10:
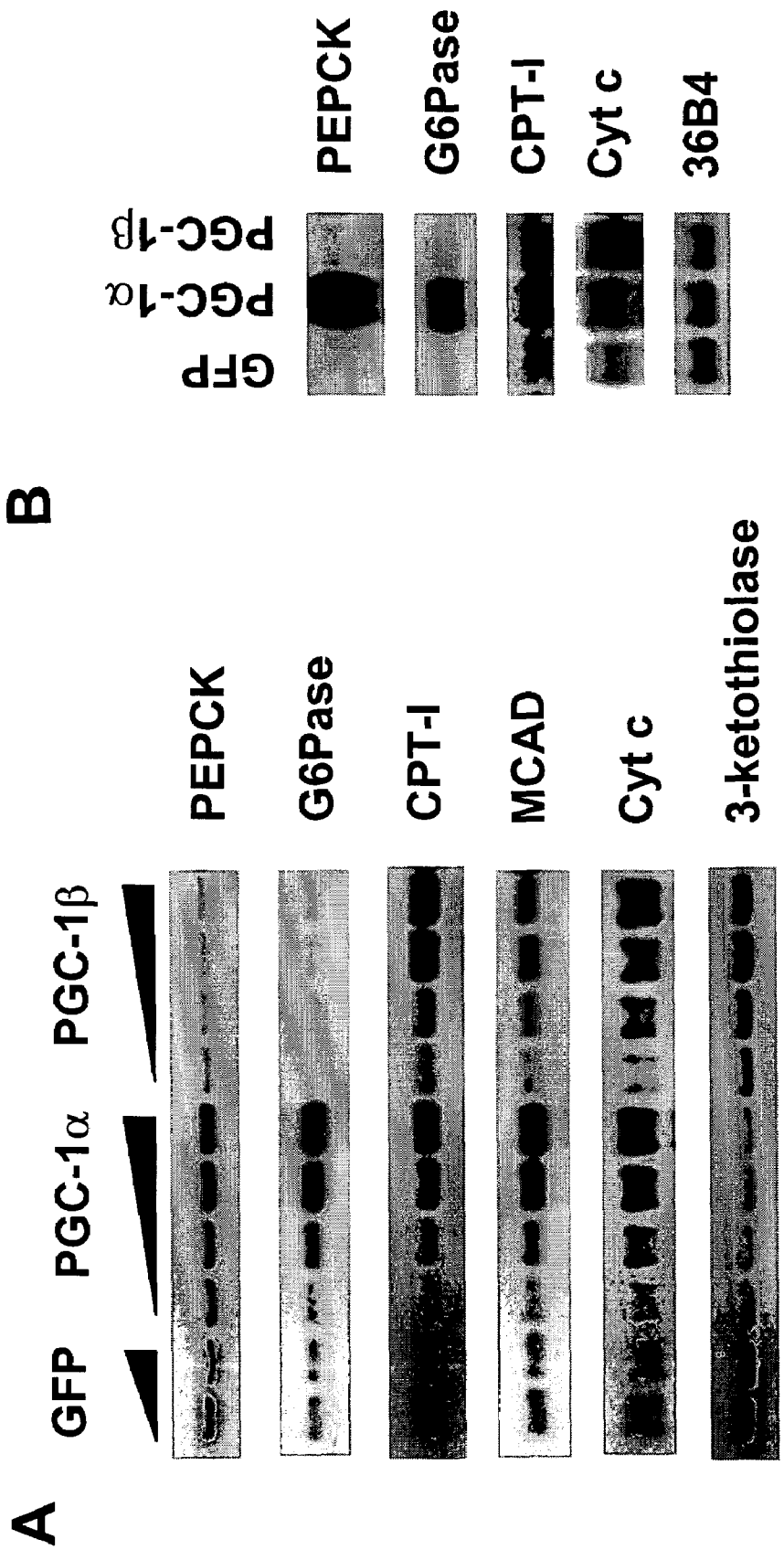
FIGS. 10A-10B depict that PGC-1β induces mitochondrial gene expression but not gluconeogenesis in hepatocytes. FAO hepatoma cells (FIG. 10A) or primary rat hepatocytes (FIG. 10B) were infected with varying doses of recombinant GFP, PGC-1α or PGC-1β viruses for 48 hours. Total RNA was isolated and analyzed by Northern hybridization to examine the expression of various genes using gene-specific probes such as PEPCK and G6Pase for gluconeogenesis and CPT-1, MCAD and Cytochrome C for fatty acid oxidation. The results indicate that PGC-1α activates both gluconeogenesis and fatty acid oxidation as evidenced by increased expression of PEPCK, G6Pase, CPT-1, MCAD and Cytochrome C, but PGC-1β only induces the mitochondrial fatty acid oxidation genes CPT-1, MCAD and Cytochrome C.

To test whether PGC-1β plays a direct role in the activation of hepatic gluconeogenesis in cultured primary hepatocytes and rats, FAO hepatoma cells (FIG. 10A) or primary rat hepatocytes (FIG. 10B) were infected with varying doses of recombinant GFP, PGC-1α or PGC-1β viruses for 48 hours. Total RNA was isolated and analyzed by Northern hybridization to examine the expression of various genes using gene-specific probes such as PEPCK and G6Pase for gluconeogenesis and CPT-1, MCAD and CytC for fatty acid oxidation. The results indicate that PGC-1α activates both gluconeogenesis and fatty acid oxidation as evidenced by increased expression of PEPCK, G6Pase, CPT-1, MCAD and CytC, but PGC-1β only induces the mitochondrial fatty acid oxidation genes CPT-1, MCAD and CytC. Thus, PGC-1β induces mitochondrial gene expression but not gluconeogenesis in hepatocytes. The inability of PGC-1β to induce gluconeogenesis, in contrast to PGC-1α, is an important distinguishing characteristic of PGC-1β in the arena of therapeutics for metabolic disorders, e.g., diabetes, where gluconeogenesis-related side-effects are undesirable.

Example 3

Interaction of Murine PGC-1β with Nuclear Receptors

Figure 7B:
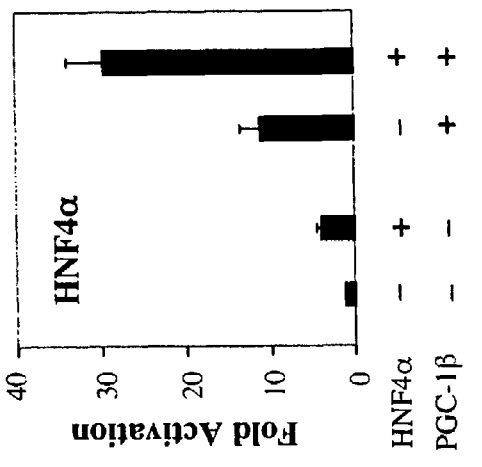
FIGS. 7A-7D depict the results of transcriptional analysis of the coactivation of nuclear receptors by murine PGC-1β. COS cells were cotransfected with vectors expressing GR (FIG. 7A), HNF4α (FIG. 7B), NRF1 (FIG. 7C), or TRβ (FIG. 7D), along with reporter plasmids alone or in the presence of PGC-1β. For GR and TRβ transfection, ligands (Dex, 1 µM dexamethasone, and 50 nM T3, respectively) were added 24 hours before the cells were lysed and assayed for luciferase activity.
Figure 7D:
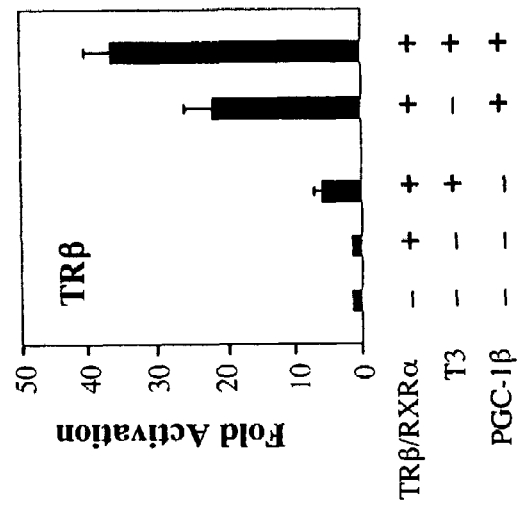
Figure 7A:
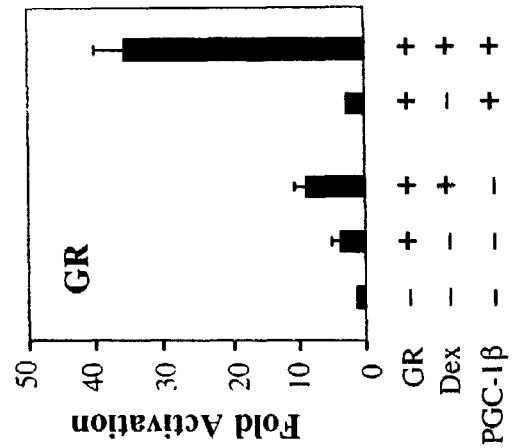
Figure 7C:
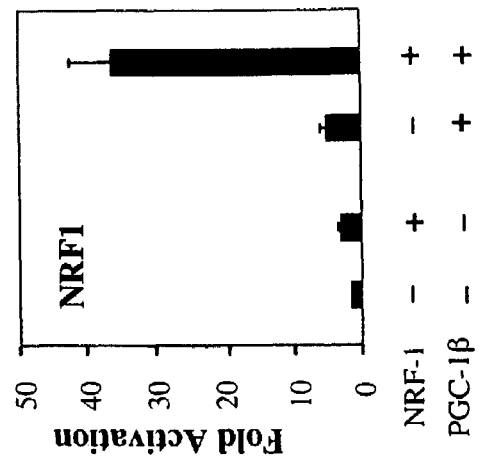

PPARα and HNF4α are important transcription regulators implicated in hepatic fatty acid oxidation and gluconeogenesis during periods of food deprivation (Kersten, S. et al. (1999) *J. Clin. Invest.* 103:1489-1498). It was therefore determined whether PGC-1β, like PGC-1α, could physically interact with and coactivate these transcription factors. The N-terminus of PGC-1β (amino acid residues 1-350 of SEQ ID NO:2), which contains three putative nuclear receptor binding motifs (LXXLL motifs) is able to "pulldown" in vitro translated HNF4α and PPARα with similar efficiency as PGC-1α. Furthermore, the full-length PGC-1α is readily coimmunoprecipitated with HNF4α when coexpressed in BOSC cells, indicating in vivo association of these two proteins. The interaction between PGC-1β and PPARα is slightly increased in the presence of Wy-14643, a PPARα ligand. In contrast, the recruitment of PGC-1β by RARα (retinoic acid receptor α) and TRβ (thyroid hormone receptor β) is highly dependent on their respective ligands. Consistent with a potential role in regulating hepatic gluconeogenesis, PGC-1β potently enhances the transcriptional activity of GR (glucocorticoid receptor) and HNF4α on reporter constructs containing multimerized cognate binding sites (FIGS. 7A and 7B, respectively). Coactivation of GR by PGC-1β is strictly dependent on the presence of dexamethasone, a synthetic glucocorticoid, indicating ligand-dependent recruitment of the coactivator to the receptor; the latter is also observed for TRβ and RARα (FIG. 7D). In addition to coactivating NRs, PGC-1β is also a potent regulator of the transcriptional activity of NRF1, a central transcription factor in the control of mitochondrial biogenesis (FIG. 7C). These results demonstrate that PGC-1β regulates the transcriptional activity of an array of nuclear receptors and other transcription factors through direct physical association with these factors. Significantly, these include factors known to be important in mitochondrial biogenesis, fatty acid oxidation, and gluconeogenesis.

Example 4

Analysis of PGC-1β Transcriptional Activity

Figure 8:
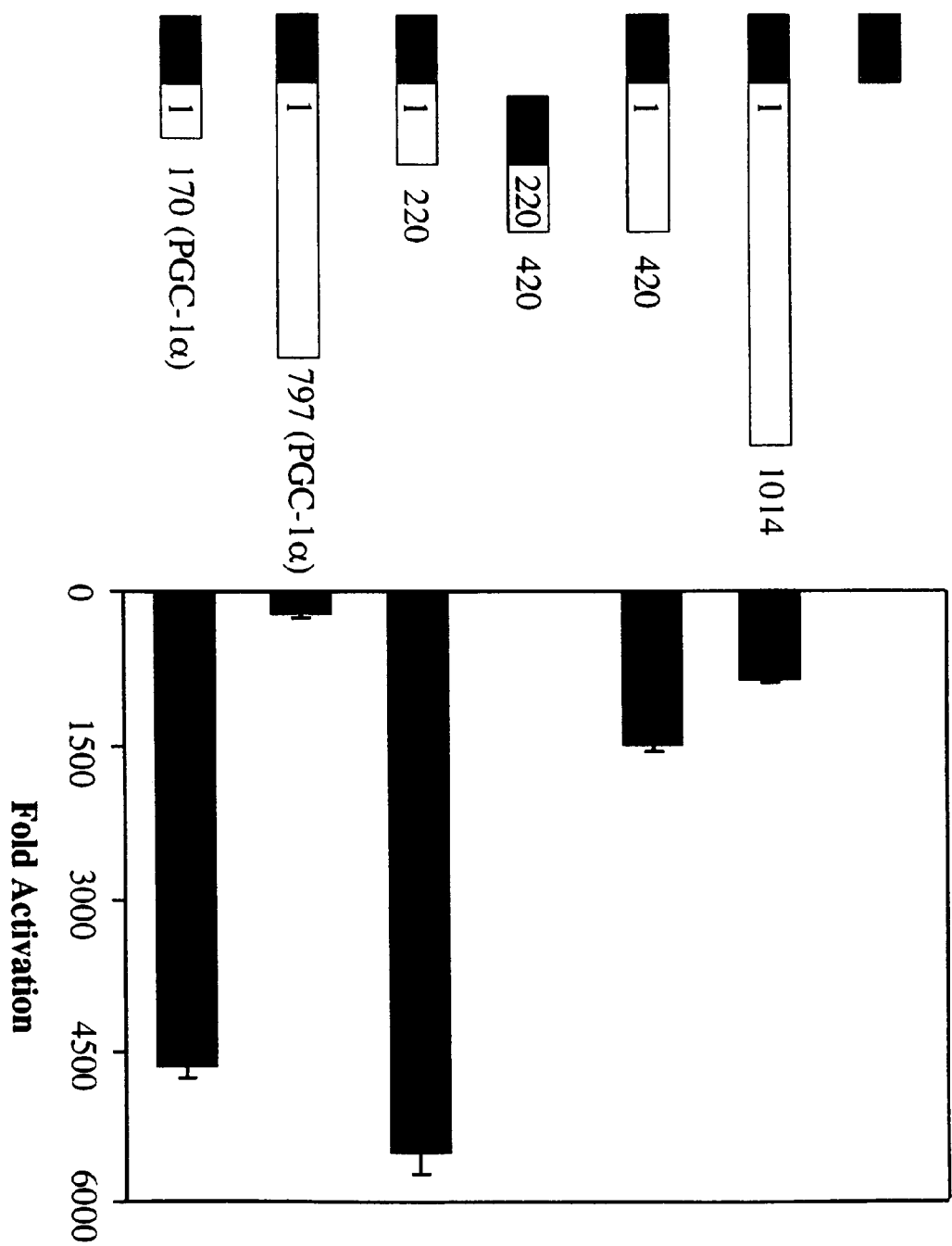
FIG. 8 depicts the mapping of the transcriptional activation domain of murine PGC-1β. Full-length PGC-1β or fragments thereof were fused to GAL4-DBD and assayed for the activation of transcription from a 5×UAS-luciferase reporter construct (5×UAS, five copies of the upstream activation sequence) in transiently transfected BOSC cells. GAL4-DBD-PGC1α fusion plasmids were included for comparison. Luciferase activity was expressed as fold activation over vector alone. Error bars indicate SEM of three independent experiments performed in duplicate.

This example examines whether PGC-1β has autonomous transcriptional activity when fused to a heterologous DNA binding domain. PGC-1β potently activates transcription from a UAS-luciferase reporter construct when fused to the DNA binding domain of yeast GAL4 (FIG. 8). Deletion of the C-terminus further increases its transcriptional activity. The transactivation domain of PGC-1β is localized to the N-terminus of the protein.

Sequence alignment of all PGC-1 family members revealed several conserved patches of amino acids that may be important for their function. One such region contains a tetrapeptide motif, DHDY (SEQ ID NO:7), that is a putative HCF-binding motif (HBM) with a consensus sequence of [D/E]-H-X-Y, wherein [D/E] indicates either D or E, and X indicates any amino acid residue. Proteins containing this motif have been shown to associate with HCF, including HSV viral protein VP16 and a basic leucine-zipper protein, LZIP (Freiman, R. N. and Herr, W. (1997) Genes Dev. 11:3122-3127). HCF does not bind DNA by itself; however, it can be recruited by DNA-binding transcription factors such as Oct-1 and functions as a scaffold for the assembly of transactivation complexes (Vogel, J. L. and Kristie, T. M. (2000) EMBO J. 19:683-690).

Figures 9A, 9B:
In FIG. 9A, BOSC cells were transiently transfected with GAL4-PGC-1β and FLAG-HCF expression constructs as indicated.
In FIG. 9B, the N-terminal 380 amino acids of HCF were fused to GAL4-DBD. The resulting construct was transiently transfected into BOSC cells alone or in the presence of Flag-PGC-1β. Luciferase activity was expressed as fold activation over vector alone. Error bars indicate SEM of three independent experiments performed in duplicate.

PGC-1α and PGC-1β may mediate the recruitment of HCF-containing protein complexes to the NR binding sites, thereby modulating NR-regulated transcription. To test whether PGC-1α and PGC-1β are physically associated with HCF in vivo, Flag-tagged HCF was cotransfected with GAL-PGC-1α or PGC-1β and analyzed by immunoprecipitation followed by western blot analysis. HCF strongly interacts with both PGC-1α and PGC-1β, thus identifying a novel interaction partner for PGC-1-related coactivators. Recruitment of HCF to PGC-1β increases the transcriptional activity of PGC-1β three fold in a cotransfection assay (FIG. 9A). On the other hand, PGC-1β can be recruited by the N-terminal 380 amino acids of HCF, a domain that has been shown to interact with HBM-containing proteins, and potently increases the transcriptional activity of HCF fused to the GAL4 DBD (FIG. 9B). Coactivation of HCF was also observed for PGC-1α. These results demonstrate that HCF can function in complex with PGC-1α or PGC-1β to activate transcription from target genes.

Example 5

Expression of Recombinant PGC-1β Protein in Bacterial Cells

In this example, PGC-1β is expressed as a recombinant glutathione-S-transferase (GST) fusion polypeptide in E. coli and the fusion polypeptide is isolated and characterized. Specifically, PGC-1β is fused to GST and this fusion polypeptide is expressed in E. coli, e.g., strain PEB199. Expression of the GST-PGC-1β fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 6

Expression of Recombinant PGC-1β Protein in Mammalian Cells

To express the PGC-1β gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire PGC-1β protein and a FLAG tag fused in-frame to its 5' end of the fragment is cloned into the polylinker region of the vector, thereby placing the expression of the recombinant protein under the control of the CMV promoter.

To construct the plasmid, the PGC-1β DNA sequence is amplified by PCR using two primers. The 5' primer contains the restriction site of interest followed by approximately twenty nucleotides of the PGC-1β coding sequence starting from the initiation codon; the 3' end sequence contains complementary sequences to the other restriction site of interest, a translation stop codon, and the 3' untranslated region of the PGC-1β cDNA. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the PGC-1β gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

Mammalian cells are subsequently transfected with the PGC-1β-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the PGC-1β polypeptide is detected by radiolabeling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an FLAG specific monoclonal antibody. Briefly, the cells are labeled for 8 hours with $^{35}$S-methionine (or $^{35}$S-cysteine). The cells are lysed using detergents (RIPA buffer, 150 mM NaCl, 1% NP-40, 0.1% SDS, 0.5% DOC, 50 mM Tris, pH 7.5).and precipitated with an HA-specific monoclonal antibody. Precipitated polypeptides are then analyzed by SDS-PAGE using a PGC-1β specific monoclonal antibody.

Example 7

Role of PGC-1 in Cellular Defense

To test whether PGC-1β induces mitochondrial biogenesis in murine myotubes, C2C12 myotubes were infected with recombinant adenoviruses. Total RNA (FIG. 11A) or DNA (FIG. 11B) was isolated and examined for gene expression or mitochondrial content, respectively. The results showed that both PGC-1α and PGC-1β activate mitochondrial gene expression.

Figure 11:
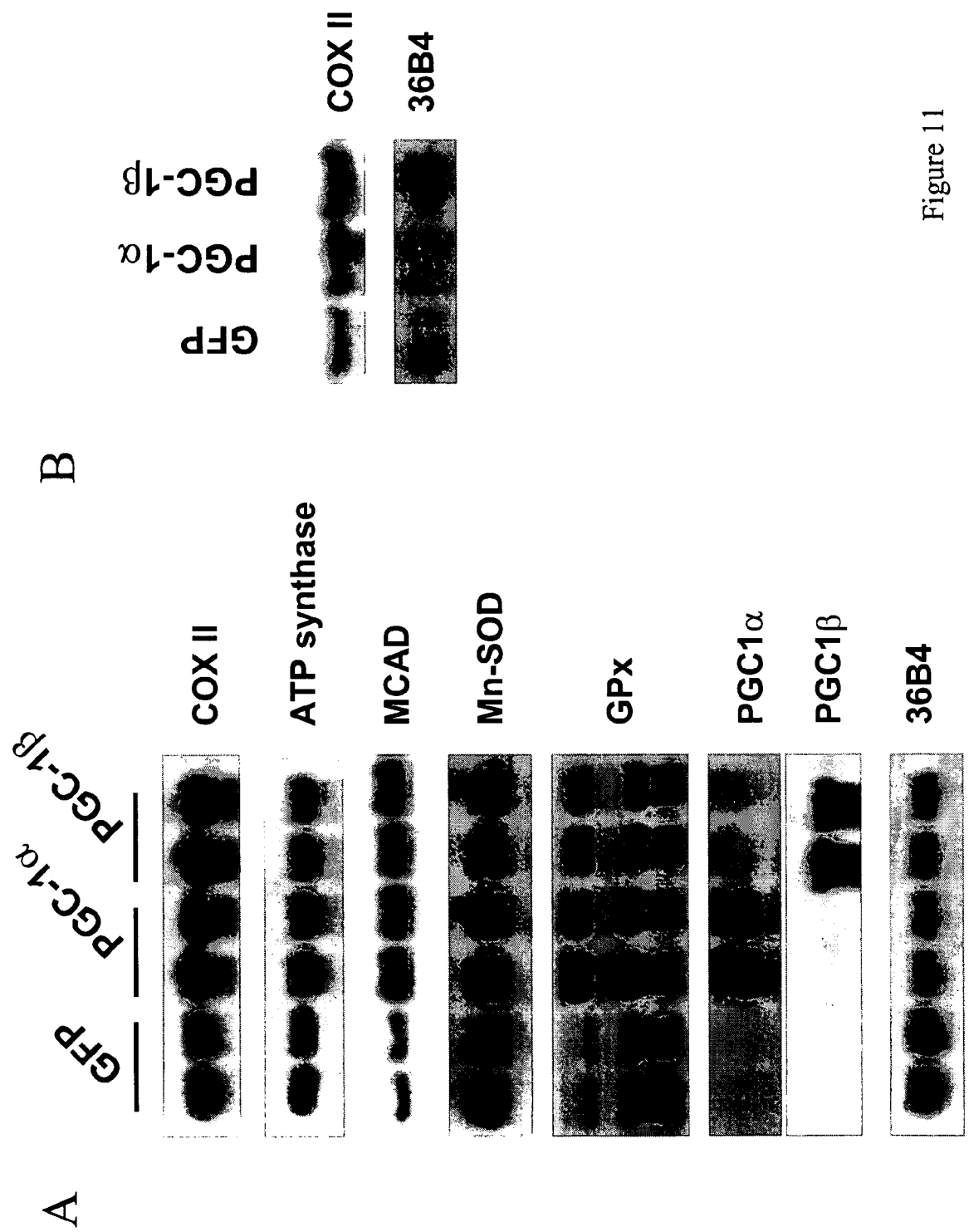
FIGS. 11A-11B depict that PGC-1β induces mitochondrial biogenesis in murine myotubes and that enzymes involved in free radical metabolism are highly elevated in response to PGC-1α and PGC-1β. C2C12 myotubes were infected with recombinant adenoviruses and total RNA (FIG. 11A) and total DNA (FIG. 11B) was isolated and examined for gene expression and mitochondrial DNA content, respectively.
Figure 12:
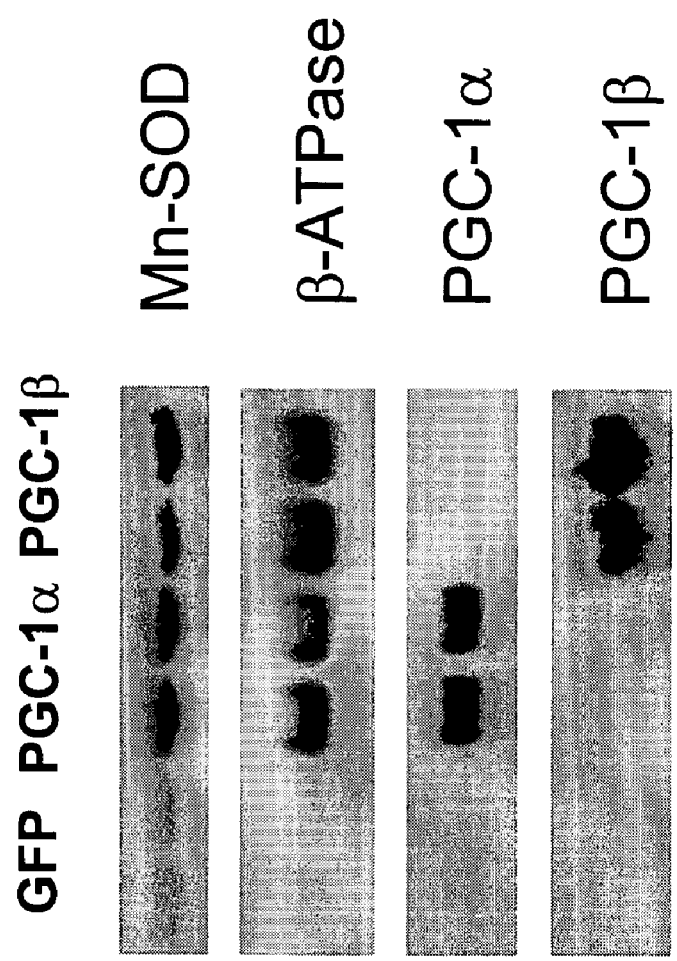
FIG. 12 depicts that PGC-1α and PGC-1β induce mitochondrial gene expression in neuroblastoma cells.

Expression of enzymes involved in free-radical metabolism such as superoxide dismutase (Mn-SOD) and glutathione peroxidase (GPx) in response to PGC-1α and PGC-1β was also tested (FIG. 11A). The results show that enzymes involved in free radical metabolism are highly elevated in response to both PGC-1α and PGC-1β. Thus, the PGC-1 family of coactivators play an important role in the cellular defense against free radical damage.

Example 8

Expression of PGC-1β Protein in Neuroblastoma Cells

To test whether PGC-1β induces mitochondrial gene expression in neuroblastoma cells, human neuroblastoma cells were cultured and infected with recombinant adenoviruses expressing PGC-1α and PGC-1β, respectively. Total RNA was isolated and analyzed by hybridization using specific probes. The results show that both PGC-1α and PGC-1β significantly increase mitochondrial gene expression. The ability of PGC-1 coactivators to regulate mitochondrial gene expression in neuronal cells indicates that PGC-1 may be an important regulator of brain energy metabolism. Since abnormal mitochondrial function is usually implicated in neurological disorders such as Parkinson's disease, PGC-1 may be an important therapeutic target in the arena of neurodegenerative diseases.

Equivalents

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

```
<160> NUMBER OF SEQ ID NOS: 6

<210> SEQ ID NO 1
<211> LENGTH: 3030
<212> TYPE: DNA
<213> ORGANISM: Mus musculus
<220> FEATURE:
<221> NAME/KEY: CDS
<222> LOCATION: (1)...(3030)

<400> SEQUENCE: 1 atg cct cct gtg tat gcc tct gag tat gtc ttg cca ctc cag ggt gga       48
Met Pro Pro Val Tyr Ala Ser Glu Tyr Val Leu Pro Leu Gln Gly Gly
 1               5                  10                  15 ggg tcc ggg gag gag caa ctc tat gct gac ttt cca gaa ctc gac ctc       96
Gly Ser Gly Glu Glu Gln Leu Tyr Ala Asp Phe Pro Glu Leu Asp Leu
            20                  25                  30 tcc cag ctg gat gcc agc gac ttt gac tcg gcc acc tgc ttt ggg gag      144
Ser Gln Leu Asp Ala Ser Asp Phe Asp Ser Ala Thr Cys Phe Gly Glu
        35                  40                  45 ctg cag tgg tgc cca gag aac tca gag act gaa ccc aac cag tac agc      192
Leu Gln Trp Cys Pro Glu Asn Ser Glu Thr Glu Pro Asn Gln Tyr Ser
    50                  55                  60 ccc gat gac tcc gag ctc ttc cag att gac agt gag aat gag gcc ctc      240
Pro Asp Asp Ser Glu Leu Phe Gln Ile Asp Ser Glu Asn Glu Ala Leu
65                  70                  75                  80 ctg gca gag ctc acc aag acc ctg gat gac atc cct gaa gat gac gtg      288
Leu Ala Glu Leu Thr Lys Thr Leu Asp Asp Ile Pro Glu Asp Asp Val
                85                  90                  95 ggt ctg gct gcc ttc cca gcc ctg gat ggt gga gac gct cta tca tgc      336
Gly Leu Ala Ala Phe Pro Ala Leu Asp Gly Gly Asp Ala Leu Ser Cys
            100                 105                 110 acc tca gct tcg cct gcc ccc tca tct gca ccc ccc agc cct gcc ccg      384
Thr Ser Ala Ser Pro Ala Pro Ser Ser Ala Pro Pro Ser Pro Ala Pro
        115                 120                 125
```

-continued

| | |
|---|---|
| gag aag ccc tcg gcc cca gcc cct gag gtg gac gag ctc tca ctg ctg<br>Glu Lys Pro Ser Ala Pro Ala Pro Glu Val Asp Glu Leu Ser Leu Leu<br>130                             135                       140 | 432 |
| cag aag ctc ctc ctg gcc aca tcc tac cca aca tca agc tct gac acc<br>Gln Lys Leu Leu Leu Ala Thr Ser Tyr Pro Thr Ser Ser Ser Asp Thr<br>145                     150                       155                   160 | 480 |
| cag aag gaa ggg acc gcc tgg cgc cag gca ggc ctc aga tct aaa agt<br>Gln Lys Glu Gly Thr Ala Trp Arg Gln Ala Gly Leu Arg Ser Lys Ser<br>                   165                     170                     175 | 528 |
| caa cgg cct tgt gtt aag gcg gac agc acc caa gac aag aag gct ccc<br>Gln Arg Pro Cys Val Lys Ala Asp Ser Thr Gln Asp Lys Lys Ala Pro<br>               180                     185                     190 | 576 |
| atg atg cag tct cag agc cga agt tgt aca gaa cta cat aag cac ctc<br>Met Met Gln Ser Gln Ser Arg Ser Cys Thr Glu Leu His Lys His Leu<br>             195                     200                     205 | 624 |
| acc tcg gca cag tgc tgc ctg cag gat cgg ggt ctg cag cca cca tgc<br>Thr Ser Ala Gln Cys Cys Leu Gln Asp Arg Gly Leu Gln Pro Pro Cys<br>210                             215                       220 | 672 |
| ctc cag agt ccc cgg ctc cct gcc aag gag gac aag gag ccg ggt gag<br>Leu Gln Ser Pro Arg Leu Pro Ala Lys Glu Asp Lys Glu Pro Gly Glu<br>225                           230                     235                 240 | 720 |
| gac tgc ccg agc ccc cag cca gct cca gcc tct ccc cgg gac tcc cta<br>Asp Cys Pro Ser Pro Gln Pro Ala Pro Ala Ser Pro Arg Asp Ser Leu<br>                     245                     250                     255 | 768 |
| gct ctg ggc agg gca gac ccc ggt gcc ccg gtt tcc cag gaa gac atg<br>Ala Leu Gly Arg Ala Asp Pro Gly Ala Pro Val Ser Gln Glu Asp Met<br>             260                     265                     270 | 816 |
| cag gcg atg gtg caa ctc ata cgc tac atg cac acc tac tgc ctc ccc<br>Gln Ala Met Val Gln Leu Ile Arg Tyr Met His Thr Tyr Cys Leu Pro<br>               275                     280                     285 | 864 |
| cag agg aag ctg ccc cca cag acc cct gag cca ctc ccc aag gcc tgc<br>Gln Arg Lys Leu Pro Pro Gln Thr Pro Glu Pro Leu Pro Lys Ala Cys<br>290                           295                     300 | 912 |
| agc aac ccc tcc cag cag gtc aga tcc cgg ccc tgg tcc cgg cac cac<br>Ser Asn Pro Ser Gln Gln Val Arg Ser Arg Pro Trp Ser Arg His His<br>305                           310                     315                 320 | 960 |
| tcc aaa gcc tcc tgg gct gag ttc tcc att ctg agg gaa ctt ctg gct<br>Ser Lys Ala Ser Trp Ala Glu Phe Ser Ile Leu Arg Glu Leu Leu Ala<br>                     325                     330                   335 | 1008 |
| caa gac gtg ctc tgt gat gtc agc aaa ccc tac cgt ctg gcc acg cct<br>Gln Asp Val Leu Cys Asp Val Ser Lys Pro Tyr Arg Leu Ala Thr Pro<br>                     340                     345                   350 | 1056 |
| gtt tat gcc tcc ctc aca cct cgg tca agg ccc agg ccc ccc aaa gac<br>Val Tyr Ala Ser Leu Thr Pro Arg Ser Arg Pro Arg Pro Pro Lys Asp<br>               355                     360                     365 | 1104 |
| agt cag gcc tcc cct ggt cgc cca tcc tcg gtg gag gag gta agg atc<br>Ser Gln Ala Ser Pro Gly Arg Pro Ser Ser Val Glu Glu Val Arg Ile<br>370                           375                     380 | 1152 |
| gca gct tca ccc aag agc acc ggg ccc aga cca agc ctg cgc cca ctg<br>Ala Ala Ser Pro Lys Ser Thr Gly Pro Arg Pro Ser Leu Arg Pro Leu<br>385                           390                     395                 400 | 1200 |
| cgg ctg gag gtg aaa agg gag gtc cgc cgg cct gcc aga ctg cag cag<br>Arg Leu Glu Val Lys Arg Glu Val Arg Arg Pro Ala Arg Leu Gln Gln<br>                     405                     410                   415 | 1248 |
| cag gag gag gaa gac gag gaa gag gag gag gaa gag gaa gaa gaa<br>Gln Glu Glu Glu Asp Glu Glu Glu Glu Glu Glu Glu Glu Glu Glu<br>                        420                     425                   430 | 1296 |
| aaa gag gag gag gag gag tgg ggc agg aaa agg cca ggc cga ggc ctg<br>Lys Glu Glu Glu Glu Glu Trp Gly Arg Lys Arg Pro Gly Arg Gly Leu | 1344 |

-continued

```
                435                 440                 445
cca tgg acg aag ctg ggg agg aag ctg gag agc tct gtg tgc ccc gtg    1392
Pro Trp Thr Lys Leu Gly Arg Lys Leu Glu Ser Ser Val Cys Pro Val
    450                 455                 460 cgg cgt tct cgg aga ctg aac cct gag ctg ggc ccc tgg ctg aca ttt    1440
Arg Arg Ser Arg Arg Leu Asn Pro Glu Leu Gly Pro Trp Leu Thr Phe
465                 470                 475                 480 gca gat gag ccg ctg gtc ccc tcg gag ccc caa ggt gct ctg ccc tca    1488
Ala Asp Glu Pro Leu Val Pro Ser Glu Pro Gln Gly Ala Leu Pro Ser
                485                 490                 495 ctg tgc ctg gct ccc aag gcc tac gac gta gag cgg gag ctg ggc agc    1536
Leu Cys Leu Ala Pro Lys Ala Tyr Asp Val Glu Arg Glu Leu Gly Ser
            500                 505                 510 ccc acg gac gag gac agt ggc caa gac cag cag ctc cta cgg gga ccc    1584
Pro Thr Asp Glu Asp Ser Gly Gln Asp Gln Gln Leu Leu Arg Gly Pro
        515                 520                 525 cag atc cct gcc ctg gag agc ccc tgt gag agt ggc gac cca act ttt    1632
Gln Ile Pro Ala Leu Glu Ser Pro Cys Glu Ser Gly Asp Pro Thr Phe
    530                 535                 540 ggc aag aag agc ttt gag cag acc ttg aca gtg gag ctc tgt ggc aca    1680
Gly Lys Lys Ser Phe Glu Gln Thr Leu Thr Val Glu Leu Cys Gly Thr
545                 550                 555                 560 gca ggt gag cca ggg ggc ttc cac tgg cag gtg cct tca gga aaa cac    1728
Ala Gly Glu Pro Gly Gly Phe His Trp Gln Val Pro Ser Gly Lys His
                565                 570                 575 ccg tgc atc tct gag ttt ttc atc atg cat ggg caa gga ctc acc cca    1776
Pro Cys Ile Ser Glu Phe Phe Ile Met His Gly Gln Gly Leu Thr Pro
            580                 585                 590 ccc acc aca cca ccg tac aag ccc aca gag gag gat ccc ttc aaa cca    1824
Pro Thr Thr Pro Pro Tyr Lys Pro Thr Glu Glu Asp Pro Phe Lys Pro
        595                 600                 605 gac atc aag cat agt cta ggc aaa gaa ata gct ctc agc ctc ccc tcc    1872
Asp Ile Lys His Ser Leu Gly Lys Glu Ile Ala Leu Ser Leu Pro Ser
    610                 615                 620 cct gag ggc ctc tca ctc aag gcc acc cca ggg gct gcc cac aag ctg    1920
Pro Glu Gly Leu Ser Leu Lys Ala Thr Pro Gly Ala Ala His Lys Leu
625                 630                 635                 640 cca aag aag cac cca gag cga agt gag ctc ctg tcc cac ctg cga cat    1968
Pro Lys Lys His Pro Glu Arg Ser Glu Leu Leu Ser His Leu Arg His
                645                 650                 655 gcc aca gcc cag cca gcc tcc cag gct ggc cag aag cgt ccc ttc tcc    2016
Ala Thr Ala Gln Pro Ala Ser Gln Ala Gly Gln Lys Arg Pro Phe Ser
            660                 665                 670 tgt tcc ttt gga gac cat gac tac tgc cag gtg ctc cga cca gaa ggc    2064
Cys Ser Phe Gly Asp His Asp Tyr Cys Gln Val Leu Arg Pro Glu Gly
        675                 680                 685 gtc ctg caa agg aag gtg ctg agg tcc tgg gag ccg tct ggg gtt cac    2112
Val Leu Gln Arg Lys Val Leu Arg Ser Trp Glu Pro Ser Gly Val His
    690                 695                 700 ctt gag gac tgg ccc cag cag ggt gcc cct tgg gct gag gca cag gcc    2160
Leu Glu Asp Trp Pro Gln Gln Gly Ala Pro Trp Ala Glu Ala Gln Ala
705                 710                 715                 720 cct ggc agg gag gaa gac aga agc tgt gat gct ggc gcc cca ccc aag    2208
Pro Gly Arg Glu Glu Asp Arg Ser Cys Asp Ala Gly Ala Pro Pro Lys
                725                 730                 735 gac agc acg ctg ctg aga gac cat gag atc cgt gcc agc ctc acc aaa    2256
Asp Ser Thr Leu Leu Arg Asp His Glu Ile Arg Ala Ser Leu Thr Lys
            740                 745                 750 cac ttt ggg ctg ctg gag acc gcc ctg gag gag gaa gac ctg gcc tcc    2304
```

|  |  |  |  |  |  |  |  |  |  |  |  |  |  |  |  |
|---|---|---|---|---|---|---|---|---|---|---|---|---|---|---|---|
| His | Phe | Gly | Leu | Leu | Glu | Thr | Ala | Leu | Glu | Glu | Asp | Leu | Ala | Ser |  |
|  |  | 755 |  |  |  | 760 |  |  |  | 765 |  |  |  |  |  |

```
tgc aag agc cct gag tat gac act gtc ttt gaa gac agc agc agc agc     2352
Cys Lys Ser Pro Glu Tyr Asp Thr Val Phe Glu Asp Ser Ser Ser Ser
    770             775             780 agc ggc gag agc agc ttc ctc cca gag gag gaa gag gaa ggg gag         2400
Ser Gly Glu Ser Ser Phe Leu Pro Glu Glu Glu Glu Glu Gly Glu
785             790             795             800 gag gag gag gag gac gat gaa gaa gag gac tca ggg gtc agc ccc act     2448
Glu Glu Glu Glu Asp Asp Glu Glu Glu Asp Ser Gly Val Ser Pro Thr
                805             810             815 tgc tct gac cac tgc ccc tac cag agc cca cca agc aag gcc aac cgg     2496
Cys Ser Asp His Cys Pro Tyr Gln Ser Pro Pro Ser Lys Ala Asn Arg
            820             825             830 cag ctc tgt tcc cgc agc cgc tca agc tct ggc tct tca ccc tgc cac     2544
Gln Leu Cys Ser Arg Ser Arg Ser Ser Ser Gly Ser Ser Pro Cys His
        835             840             845 tcc tgg tca cca gcc act cga agg aac ttc aga tgt gag agc aga ggg     2592
Ser Trp Ser Pro Ala Thr Arg Arg Asn Phe Arg Cys Glu Ser Arg Gly
    850             855             860 ccg tgt tca gac aga acg cca agc atc cgg cac gcc agg aag cgg cgg     2640
Pro Cys Ser Asp Arg Thr Pro Ser Ile Arg His Ala Arg Lys Arg Arg
865             870             875             880 gaa aag gcc att ggg gaa ggc cgc gtg gtg tac att caa aat ctc tcc     2688
Glu Lys Ala Ile Gly Glu Gly Arg Val Val Tyr Ile Gln Asn Leu Ser
                885             890             895 agc gac atg agc tcc cga gag ctg aag agg cgc ttt gaa gtg ttt ggt     2736
Ser Asp Met Ser Ser Arg Glu Leu Lys Arg Arg Phe Glu Val Phe Gly
            900             905             910 gag att gag gag tgc gag gtg ctg aca aga aat agg aga ggc gag aag     2784
Glu Ile Glu Glu Cys Glu Val Leu Thr Arg Asn Arg Arg Gly Glu Lys
        915             920             925 tac ggc ttc atc acc tac cgg tgt tct gag cac gcg gcc ctc tct ttg     2832
Tyr Gly Phe Ile Thr Tyr Arg Cys Ser Glu His Ala Ala Leu Ser Leu
    930             935             940 aca aag ggc gct gcc ctg agg aag cgc aac gag ccc tcc ttc cag ctg     2880
Thr Lys Gly Ala Ala Leu Arg Lys Arg Asn Glu Pro Ser Phe Gln Leu
945             950             955             960 agc tac gga ggg ctc cgg cac ttc tgc tgg ccc aga tac act gac tac     2928
Ser Tyr Gly Gly Leu Arg His Phe Cys Trp Pro Arg Tyr Thr Asp Tyr
                965             970             975 gat tcc aat tca gaa gag gcc ctt cct gcg tca ggg aaa agc aag tat     2976
Asp Ser Asn Ser Glu Glu Ala Leu Pro Ala Ser Gly Lys Ser Lys Tyr
            980             985             990 gaa gcc atg gat ttt gac agc tta ctg aaa gag gcc cag cag agc ctg     3024
Glu Ala Met Asp Phe Asp Ser Leu Leu Lys Glu Ala Gln Gln Ser Leu
        995             1000            1005 cat tga                                                              3030
His *

<210> SEQ ID NO 2
<211> LENGTH: 1009
<212> TYPE: PRT
<213> ORGANISM: Mus musculus

<400> SEQUENCE: 2

Met Pro Pro Val Tyr Ala Ser Glu Tyr Val Leu Pro Leu Gln Gly Gly
1               5                   10                  15

Gly Ser Gly Glu Glu Gln Leu Tyr Ala Asp Phe Pro Glu Leu Asp Leu
            20                  25                  30
```

-continued

```
Ser Gln Leu Asp Ala Ser Asp Phe Asp Ser Ala Thr Cys Phe Gly Glu
         35                  40                  45
Leu Gln Trp Cys Pro Glu Asn Ser Glu Thr Glu Pro Asn Gln Tyr Ser
 50                  55                  60
Pro Asp Asp Ser Glu Leu Phe Gln Ile Asp Ser Glu Asn Glu Ala Leu
 65                  70                  75                  80
Leu Ala Glu Leu Thr Lys Thr Leu Asp Asp Ile Pro Glu Asp Asp Val
                 85                  90                  95
Gly Leu Ala Ala Phe Pro Ala Leu Asp Gly Asp Ala Leu Ser Cys
            100                 105                 110
Thr Ser Ala Ser Pro Ala Pro Ser Ala Pro Pro Ser Pro Ala Pro
            115                 120                 125
Glu Lys Pro Ser Ala Pro Ala Pro Glu Val Asp Glu Leu Ser Leu Leu
            130                 135                 140
Gln Lys Leu Leu Leu Ala Thr Ser Tyr Pro Thr Ser Ser Ser Asp Thr
145                 150                 155                 160
Gln Lys Glu Gly Thr Ala Trp Arg Gln Ala Gly Leu Arg Ser Lys Ser
                165                 170                 175
Gln Arg Pro Cys Val Lys Ala Asp Ser Thr Gln Asp Lys Lys Ala Pro
            180                 185                 190
Met Met Gln Ser Gln Ser Arg Ser Cys Thr Glu Leu His Lys His Leu
            195                 200                 205
Thr Ser Ala Gln Cys Cys Leu Gln Asp Arg Gly Leu Gln Pro Pro Cys
        210                 215                 220
Leu Gln Ser Pro Arg Leu Pro Ala Lys Glu Asp Lys Glu Pro Gly Glu
225                 230                 235                 240
Asp Cys Pro Ser Pro Gln Pro Ala Pro Ala Ser Pro Arg Asp Ser Leu
                245                 250                 255
Ala Leu Gly Arg Ala Asp Pro Gly Ala Pro Val Ser Gln Glu Asp Met
            260                 265                 270
Gln Ala Met Val Gln Leu Ile Arg Tyr Met His Thr Tyr Cys Leu Pro
            275                 280                 285
Gln Arg Lys Leu Pro Pro Gln Thr Pro Glu Pro Leu Pro Lys Ala Cys
        290                 295                 300
Ser Asn Pro Ser Gln Gln Val Arg Ser Arg Pro Trp Ser Arg His His
305                 310                 315                 320
Ser Lys Ala Ser Trp Ala Glu Phe Ser Ile Leu Arg Glu Leu Leu Ala
                325                 330                 335
Gln Asp Val Leu Cys Asp Val Ser Lys Pro Tyr Arg Leu Ala Thr Pro
            340                 345                 350
Val Tyr Ala Ser Leu Thr Pro Arg Ser Arg Pro Arg Pro Pro Lys Asp
            355                 360                 365
Ser Gln Ala Ser Pro Gly Arg Pro Ser Val Glu Glu Val Arg Ile
            370                 375                 380
Ala Ala Ser Pro Lys Ser Thr Gly Pro Arg Pro Ser Leu Arg Pro Leu
385                 390                 395                 400
Arg Leu Glu Val Lys Arg Glu Val Arg Arg Pro Ala Arg Leu Gln Gln
                405                 410                 415
Gln Glu Glu Glu Asp Glu Glu Glu Glu Glu Glu Glu Glu Glu Glu Glu
            420                 425                 430
Lys Glu Glu Glu Glu Trp Gly Arg Lys Arg Pro Gly Arg Gly Leu
            435                 440                 445
```

-continued

```
Pro Trp Thr Lys Leu Gly Arg Lys Leu Glu Ser Ser Val Cys Pro Val
    450                 455                 460
Arg Arg Ser Arg Arg Leu Asn Pro Glu Leu Gly Pro Trp Leu Thr Phe
465                 470                 475                 480
Ala Asp Glu Pro Leu Val Pro Ser Glu Pro Gln Gly Ala Leu Pro Ser
                485                 490                 495
Leu Cys Leu Ala Pro Lys Ala Tyr Asp Val Glu Arg Glu Leu Gly Ser
                500                 505                 510
Pro Thr Asp Glu Asp Ser Gly Gln Asp Gln Gln Leu Leu Arg Gly Pro
            515                 520                 525
Gln Ile Pro Ala Leu Glu Ser Pro Cys Glu Ser Gly Asp Pro Thr Phe
    530                 535                 540
Gly Lys Lys Ser Phe Glu Gln Thr Leu Thr Val Glu Leu Cys Gly Thr
545                 550                 555                 560
Ala Gly Glu Pro Gly Gly Phe His Trp Gln Val Pro Ser Gly Lys His
                565                 570                 575
Pro Cys Ile Ser Glu Phe Phe Ile Met His Gly Gln Gly Leu Thr Pro
                580                 585                 590
Pro Thr Thr Pro Pro Tyr Lys Pro Thr Glu Glu Asp Pro Phe Lys Pro
            595                 600                 605
Asp Ile Lys His Ser Leu Gly Lys Glu Ile Ala Leu Ser Leu Pro Ser
    610                 615                 620
Pro Glu Gly Leu Ser Leu Lys Ala Thr Pro Gly Ala Ala His Lys Leu
625                 630                 635                 640
Pro Lys Lys His Pro Glu Arg Ser Glu Leu Leu Ser His Leu Arg His
                645                 650                 655
Ala Thr Ala Gln Pro Ala Ser Gln Ala Gly Gln Lys Arg Pro Phe Ser
                660                 665                 670
Cys Ser Phe Gly Asp His Asp Tyr Cys Gln Val Leu Arg Pro Glu Gly
            675                 680                 685
Val Leu Gln Arg Lys Val Leu Arg Ser Trp Glu Pro Ser Gly Val His
    690                 695                 700
Leu Glu Asp Trp Pro Gln Gln Gly Ala Pro Trp Ala Glu Ala Gln Ala
705                 710                 715                 720
Pro Gly Arg Glu Glu Asp Arg Ser Cys Asp Ala Gly Ala Pro Pro Lys
                725                 730                 735
Asp Ser Thr Leu Leu Arg Asp His Glu Ile Arg Ala Ser Leu Thr Lys
                740                 745                 750
His Phe Gly Leu Leu Glu Thr Ala Leu Glu Glu Glu Asp Leu Ala Ser
            755                 760                 765
Cys Lys Ser Pro Glu Tyr Asp Thr Val Phe Glu Asp Ser Ser Ser Ser
    770                 775                 780
Ser Gly Glu Ser Ser Phe Leu Pro Glu Glu Glu Glu Glu Glu Gly Glu
785                 790                 795                 800
Glu Glu Glu Glu Asp Asp Glu Glu Asp Ser Gly Val Ser Pro Thr
                805                 810                 815
Cys Ser Asp His Cys Pro Tyr Gln Pro Pro Ser Lys Ala Asn Arg
            820                 825                 830
Gln Leu Cys Ser Arg Ser Arg Ser Ser Gly Ser Ser Pro Cys His
    835                 840                 845
Ser Trp Ser Pro Ala Thr Arg Arg Asn Phe Arg Cys Glu Ser Arg Gly
850                 855                 860
Pro Cys Ser Asp Arg Thr Pro Ser Ile Arg His Ala Arg Lys Arg Arg
```

```
                    865                 870                 875                 880

Glu Lys Ala Ile Gly Glu Gly Arg Val Val Tyr Ile Gln Asn Leu Ser
                                    885                 890                 895

Ser Asp Met Ser Ser Arg Glu Leu Lys Arg Arg Phe Glu Val Phe Gly
                                900                 905                 910

Glu Ile Glu Glu Cys Glu Val Leu Thr Arg Asn Arg Arg Gly Glu Lys
                            915                 920                 925

Tyr Gly Phe Ile Thr Tyr Arg Cys Ser Glu His Ala Ala Leu Ser Leu
                        930                 935                 940

Thr Lys Gly Ala Ala Leu Arg Lys Arg Asn Glu Pro Ser Phe Gln Leu
                945                 950                 955                 960

Ser Tyr Gly Gly Leu Arg His Phe Cys Trp Pro Arg Tyr Thr Asp Tyr
                                965                 970                 975

Asp Ser Asn Ser Glu Glu Ala Leu Pro Ala Ser Gly Lys Ser Lys Tyr
                            980                 985                 990

Glu Ala Met Asp Phe Asp Ser Leu Leu Lys Glu Ala Gln Gln Ser Leu
                        995                 1000                1005

His

<210> SEQ ID NO 3
<211> LENGTH: 3027
<212> TYPE: DNA
<213> ORGANISM: Mus musculus
<220> FEATURE:
<221> NAME/KEY: CDS
<222> LOCATION: (1)...(3027)

<400> SEQUENCE: 3 atg cct cct gtg tat gcc tct gag tat gtc ttg cca ctc cag ggt gga          48
Met Pro Pro Val Tyr Ala Ser Glu Tyr Val Leu Pro Leu Gln Gly Gly
 1               5                  10                  15 ggg tcc ggg gag gag caa ctc tat gct gac ttt cca gaa ctc gac ctc          96
Gly Ser Gly Glu Glu Gln Leu Tyr Ala Asp Phe Pro Glu Leu Asp Leu
             20                  25                  30 tcc cag ctg gat gcc agc gac ttt gac tcg gcc acc tgc ttt ggg gag         144
Ser Gln Leu Asp Ala Ser Asp Phe Asp Ser Ala Thr Cys Phe Gly Glu
         35                  40                  45 ctg cag tgg tgc cca gag aac tca gag act gaa ccc aac cag tac agc         192
Leu Gln Trp Cys Pro Glu Asn Ser Glu Thr Glu Pro Asn Gln Tyr Ser
     50                  55                  60 ccc gat gac tcc gag ctc ttc cag att gac agt gag aat gag gcc ctc         240
Pro Asp Asp Ser Glu Leu Phe Gln Ile Asp Ser Glu Asn Glu Ala Leu
 65                  70                  75                  80 ctg gca gag ctc acc aag acc ctg gat gac atc cct gaa gat gac gtg         288
Leu Ala Glu Leu Thr Lys Thr Leu Asp Asp Ile Pro Glu Asp Asp Val
                 85                  90                  95 ggt ctg gct gcc ttc cca gcc ctg gat ggt gga gac gct cta tca tgc         336
Gly Leu Ala Ala Phe Pro Ala Leu Asp Gly Gly Asp Ala Leu Ser Cys
            100                 105                 110 acc tca gct tcg cct gcc ccc tca tct gca ccc ccc agc cct gcc ccg         384
Thr Ser Ala Ser Pro Ala Pro Ser Ser Ala Pro Pro Ser Pro Ala Pro
        115                 120                 125 gag aag ccc tcg gcc cca gcc cct gag gtg gac gag ctc tca ctg ctg         432
Glu Lys Pro Ser Ala Pro Ala Pro Glu Val Asp Glu Leu Ser Leu Leu
    130                 135                 140 cag aag ctc ctc ctg gcc aca tcc tac cca aca tca agc tct gac acc         480
Gln Lys Leu Leu Leu Ala Thr Ser Tyr Pro Thr Ser Ser Ser Asp Thr
145                 150                 155                 160
```

```
cag aag gaa ggg acc gcc tgg cgc cag gca ggc ctc aga tct aaa agt      528
Gln Lys Glu Gly Thr Ala Trp Arg Gln Ala Gly Leu Arg Ser Lys Ser
            165                 170                 175 caa cgg cct tgt gtt aag gcg gac agc acc caa gac aag aag gct ccc      576
Gln Arg Pro Cys Val Lys Ala Asp Ser Thr Gln Asp Lys Lys Ala Pro
        180                 185                 190 atg atg cag tct cag agc cga agt tgt aca gaa cta cat aag cac ctc      624
Met Met Gln Ser Gln Ser Arg Ser Cys Thr Glu Leu His Lys His Leu
        195                 200                 205 acc tcg gca cag tgc tgc ctg cag gat cgg ggt ctg cag cca cca tgc      672
Thr Ser Ala Gln Cys Cys Leu Gln Asp Arg Gly Leu Gln Pro Pro Cys
    210                 215                 220 ctc cag agt ccc cgg ctc cct gcc aag gag gac aag gag ccg ggt gag      720
Leu Gln Ser Pro Arg Leu Pro Ala Lys Glu Asp Lys Glu Pro Gly Glu
225                 230                 235                 240 gac tgc ccg agc ccc cag cca gct cca gcc tct ccc cgg gac tcc cta      768
Asp Cys Pro Ser Pro Gln Pro Ala Pro Ala Ser Pro Arg Asp Ser Leu
                245                 250                 255 gct ctg ggc agg gca gac ccc ggt gcc ccg gtt tcc cag gaa gac atg      816
Ala Leu Gly Arg Ala Asp Pro Gly Ala Pro Val Ser Gln Glu Asp Met
            260                 265                 270 cag gcg atg gtg caa ctc ata cgc tac atg cac acc tac tgc ctc ccc      864
Gln Ala Met Val Gln Leu Ile Arg Tyr Met His Thr Tyr Cys Leu Pro
        275                 280                 285 cag agg aag ctg ccc cca cag acc cct gag cca ctc ccc aag gcc tgc      912
Gln Arg Lys Leu Pro Pro Gln Thr Pro Glu Pro Leu Pro Lys Ala Cys
        290                 295                 300 agc aac ccc tcc cag cag gtc aga tcc cgg ccc tgg tcc cgg cac cac      960
Ser Asn Pro Ser Gln Gln Val Arg Ser Arg Pro Trp Ser Arg His His
305                 310                 315                 320 tcc aaa gcc tcc tgg gct gag ttc tcc att ctg agg gaa ctt ctg gct     1008
Ser Lys Ala Ser Trp Ala Glu Phe Ser Ile Leu Arg Glu Leu Leu Ala
                325                 330                 335 caa gac gtg ctc tgt gat gtc agc aaa ccc tac cgt ctg gcc acg cct     1056
Gln Asp Val Leu Cys Asp Val Ser Lys Pro Tyr Arg Leu Ala Thr Pro
            340                 345                 350 gtt tat gcc tcc ctc aca cct cgg tca agg ccc agg ccc ccc aaa gac     1104
Val Tyr Ala Ser Leu Thr Pro Arg Ser Arg Pro Arg Pro Pro Lys Asp
        355                 360                 365 agt cag gcc tcc cct ggt cgc cca tcc tcg gtg gag gag gta agg atc     1152
Ser Gln Ala Ser Pro Gly Arg Pro Ser Ser Val Glu Glu Val Arg Ile
        370                 375                 380 gca gct tca ccc aag agc acc ggg ccc aga cca agc ctg cgc cca ctg     1200
Ala Ala Ser Pro Lys Ser Thr Gly Pro Arg Pro Ser Leu Arg Pro Leu
385                 390                 395                 400 cgg ctg gag gtg aaa agg gag gtc cgc cgg cct gcc aga ctg cag cag     1248
Arg Leu Glu Val Lys Arg Glu Val Arg Arg Pro Ala Arg Leu Gln Gln
                405                 410                 415 cag gag gag gaa gac gag gaa gaa gag gag gaa gag gaa gaa gaa         1296
Gln Glu Glu Glu Asp Glu Glu Glu Glu Glu Glu Glu Glu Glu Glu
                420                 425                 430 aaa gag gag gag gag gag tgg ggc agg aaa agg cca ggc cga ggc ctg     1344
Lys Glu Glu Glu Glu Glu Trp Gly Arg Lys Arg Pro Gly Arg Gly Leu
            435                 440                 445 cca tgg acg aag ctg ggg agg aag ctg gag agc tct gtg tgc ccc gtg     1392
Pro Trp Thr Lys Leu Gly Arg Lys Leu Glu Ser Ser Val Cys Pro Val
450                 455                 460 cgg cgt tct cgg aga ctg aac cct gag ctg ggc ccc tgg ctg aca ttt     1440
Arg Arg Ser Arg Arg Leu Asn Pro Glu Leu Gly Pro Trp Leu Thr Phe
465                 470                 475                 480
```

```
gca gat gag ccg ctg gtc ccc tcg gag ccc caa ggt gct ctg ccc tca    1488
Ala Asp Glu Pro Leu Val Pro Ser Glu Pro Gln Gly Ala Leu Pro Ser
            485                 490                 495 ctg tgc ctg gct ccc aag gcc tac gac gta gag cgg gag ctg ggc agc    1536
Leu Cys Leu Ala Pro Lys Ala Tyr Asp Val Glu Arg Glu Leu Gly Ser
        500                 505                 510 ccc acg gac gag gac agt ggc caa gac cag cag ctc cta cgg gga ccc    1584
Pro Thr Asp Glu Asp Ser Gly Gln Asp Gln Gln Leu Leu Arg Gly Pro
            515                 520                 525 cag atc cct gcc ctg gag agc ccc tgt gag agt ggc gac cca act ttt    1632
Gln Ile Pro Ala Leu Glu Ser Pro Cys Glu Ser Gly Asp Pro Thr Phe
530                 535                 540 ggc aag aag agc ttt gag cag acc ttg aca gtg gag ctc tgt ggc aca    1680
Gly Lys Lys Ser Phe Glu Gln Thr Leu Thr Val Glu Leu Cys Gly Thr
545                 550                 555                 560 gca ggt gag cca ggg ggc ttc cac tgg cag gtg cct tca gga aaa cac    1728
Ala Gly Glu Pro Gly Gly Phe His Trp Gln Val Pro Ser Gly Lys His
                565                 570                 575 ccg tgc atc tct gag ttt ttc atc atg cat ggg caa gga ctc acc cca    1776
Pro Cys Ile Ser Glu Phe Phe Ile Met His Gly Gln Gly Leu Thr Pro
            580                 585                 590 ccc acc aca cca ccg tac aag ccc aca gag gag gat ccc ttc aaa cca    1824
Pro Thr Thr Pro Pro Tyr Lys Pro Thr Glu Glu Asp Pro Phe Lys Pro
        595                 600                 605 gac atc aag cat agt cta ggc aaa gaa ata gct ctc agc ctc ccc tcc    1872
Asp Ile Lys His Ser Leu Gly Lys Glu Ile Ala Leu Ser Leu Pro Ser
    610                 615                 620 cct gag ggc ctc tca ctc aag gcc acc cca ggg gct gcc cac aag ctg    1920
Pro Glu Gly Leu Ser Leu Lys Ala Thr Pro Gly Ala Ala His Lys Leu
625                 630                 635                 640 cca aag aag cac cca gag cga agt gag ctc ctg tcc cac ctg cga cat    1968
Pro Lys Lys His Pro Glu Arg Ser Glu Leu Leu Ser His Leu Arg His
                645                 650                 655 gcc aca gcc cag cca gcc tcc cag gct ggc cag aag cgt ccc ttc tcc    2016
Ala Thr Ala Gln Pro Ala Ser Gln Ala Gly Gln Lys Arg Pro Phe Ser
            660                 665                 670 tgt tcc ttt gga gac cat gac tac tgc cag gtg ctc cga cca gaa ggc    2064
Cys Ser Phe Gly Asp His Asp Tyr Cys Gln Val Leu Arg Pro Glu Gly
        675                 680                 685 gtc ctg caa agg aag gtg ctg agg tcc tgg gag ccg tct ggg gtt cac    2112
Val Leu Gln Arg Lys Val Leu Arg Ser Trp Glu Pro Ser Gly Val His
    690                 695                 700 ctt gag gac tgg ccc cag cag ggt gcc cct tgg gct gag gca cag gcc    2160
Leu Glu Asp Trp Pro Gln Gln Gly Ala Pro Trp Ala Glu Ala Gln Ala
705                 710                 715                 720 cct ggc agg gag gaa gac aga agc tgt gat gct ggc gcc cca ccc aag    2208
Pro Gly Arg Glu Glu Asp Arg Ser Cys Asp Ala Gly Ala Pro Pro Lys
                725                 730                 735 gac agc acg ctg ctg aga gac cat gag atc cgt gcc agc ctc acc aaa    2256
Asp Ser Thr Leu Leu Arg Asp His Glu Ile Arg Ala Ser Leu Thr Lys
            740                 745                 750 cac ttt ggg ctg ctg gag acc gcc ctg gag gag gaa gac ctg gcc tcc    2304
His Phe Gly Leu Leu Glu Thr Ala Leu Glu Glu Glu Asp Leu Ala Ser
        755                 760                 765 tgc aag agc cct gag tat gac act gtc ttt gaa gac agc agc agc            2352
Cys Lys Ser Pro Glu Tyr Asp Thr Val Phe Glu Asp Ser Ser Ser
    770                 775                 780 agc ggc gag agc agc ttc ctc cca gag gag gaa gag gaa gaa ggg gag    2400
Ser Gly Glu Ser Ser Phe Leu Pro Glu Glu Glu Glu Glu Glu Gly Glu
```

```
                785            790            795            800
gag gag gag gag gac gat gaa gaa gag gac tca ggg gtc agc ccc act        2448
Glu Glu Glu Glu Asp Asp Glu Glu Glu Asp Ser Gly Val Ser Pro Thr
                    805            810            815 tgc tct gac cac tgc ccc tac cag agc cca cca agc aag gcc aac cgg        2496
Cys Ser Asp His Cys Pro Tyr Gln Ser Pro Pro Ser Lys Ala Asn Arg
820                 825            830 cag ctc tgt tcc cgc agc cgc tca agc tct ggc tct tca ccc tgc cac        2544
Gln Leu Cys Ser Arg Ser Arg Ser Ser Ser Gly Ser Ser Pro Cys His
        835            840            845 tcc tgg tca cca gcc act cga agg aac ttc aga tgt gag agc aga ggg        2592
Ser Trp Ser Pro Ala Thr Arg Arg Asn Phe Arg Cys Glu Ser Arg Gly
850            855            860 ccg tgt tca gac aga acg cca agc atc cgg cac gcc agg aag cgg cgg        2640
Pro Cys Ser Asp Arg Thr Pro Ser Ile Arg His Ala Arg Lys Arg Arg
865            870            875            880 gaa aag gcc att ggg gaa ggc cgc gtg gtg tac att caa aat ctc tcc        2688
Glu Lys Ala Ile Gly Glu Gly Arg Val Val Tyr Ile Gln Asn Leu Ser
                885            890            895 agc gac atg agc tcc cga gag ctg aag agg cgc ttt gaa gtg ttt ggt        2736
Ser Asp Met Ser Ser Arg Glu Leu Lys Arg Arg Phe Glu Val Phe Gly
            900            905            910 gag att gag gag tgc gag gtg ctg aca aga aat agg aga ggc gag aag        2784
Glu Ile Glu Glu Cys Glu Val Leu Thr Arg Asn Arg Arg Gly Glu Lys
        915            920            925 tac ggc ttc atc acc tac cgg tgt tct gag cac gcg gcc ctc tct ttg        2832
Tyr Gly Phe Ile Thr Tyr Arg Cys Ser Glu His Ala Ala Leu Ser Leu
930            935            940 aca aag ggc gct gcc ctg agg aag cgc aac gag ccc tcc ttc cag ctg        2880
Thr Lys Gly Ala Ala Leu Arg Lys Arg Asn Glu Pro Ser Phe Gln Leu
945            950            955            960 agc tac gga ggg ctc cgg cac ttc tgc tgg ccc aga tac act gac tac        2928
Ser Tyr Gly Gly Leu Arg His Phe Cys Trp Pro Arg Tyr Thr Asp Tyr
                965            970            975 gat tcc aat tca gaa gag gcc ctt cct gcg tca ggg aaa agc aag tat        2976
Asp Ser Asn Ser Glu Glu Ala Leu Pro Ala Ser Gly Lys Ser Lys Tyr
            980            985            990 gaa gcc atg gat ttt gac agc tta ctg aaa gag gcc cag cag agc ctg        3024
Glu Ala Met Asp Phe Asp Ser Leu Leu Lys Glu Ala Gln Gln Ser Leu
        995            1000            1005 cat                                                                     3027
His <210> SEQ ID NO 4
<211> LENGTH: 3030
<212> TYPE: DNA
<213> ORGANISM: Homo sapiens
<220> FEATURE:
<221> NAME/KEY: CDS
<222> LOCATION: (1)...(3030)

<400> SEQUENCE: 4 atg cct cct gtg tat gcc tct gag tat gtc ttg cca ctc cag ggt gga        48
Met Pro Pro Val Tyr Ala Ser Glu Tyr Val Leu Pro Leu Gln Gly Gly
1               5               10              15 ggg tcc ggg gag gag caa ctc tat gct gac ttt cca gaa ctc gac ctc        96
Gly Ser Gly Glu Glu Gln Leu Tyr Ala Asp Phe Pro Glu Leu Asp Leu
            20              25              30 tcc cag ctg gat gcc agc gac ttt gac tcg gcc acc tgc ttt ggg gag        144
Ser Gln Leu Asp Ala Ser Asp Phe Asp Ser Ala Thr Cys Phe Gly Glu
        35              40              45
```

-continued

| | | |
|---|---|---|
| ctg cag tgg tgc cca gag aac tca gag act gaa ccc aac cag tac agc<br>Leu Gln Trp Cys Pro Glu Asn Ser Glu Thr Glu Pro Asn Gln Tyr Ser<br>50              55              60 | | 192 |
| ccc gat gac tcc gag ctc ttc cag att gac agt gag aat gag gcc ctc<br>Pro Asp Asp Ser Glu Leu Phe Gln Ile Asp Ser Glu Asn Glu Ala Leu<br>65              70              75              80 | | 240 |
| ctg gca gag ctc acc aag acc ctg gat gac atc cct gaa gat gac gtg<br>Leu Ala Glu Leu Thr Lys Thr Leu Asp Asp Ile Pro Glu Asp Asp Val<br>              85              90              95 | | 288 |
| ggt ctg gct gcc ttc cca gcc ctg gat ggt gga gac gct cta tca tgc<br>Gly Leu Ala Ala Phe Pro Ala Leu Asp Gly Gly Asp Ala Leu Ser Cys<br>100             105             110 | | 336 |
| acc tca gct tcg cct gcc ccc tca tct gca ccc ccc agc cct gcc ccg<br>Thr Ser Ala Ser Pro Ala Pro Ser Ser Ala Pro Pro Ser Pro Ala Pro<br>115             120             125 | | 384 |
| gag aag ccc tcg gcc cca gcc cct gag gtg gac gag ctc tca ctg ctg<br>Glu Lys Pro Ser Ala Pro Ala Pro Glu Val Asp Glu Leu Ser Leu Leu<br>130             135             140 | | 432 |
| cag aag ctc ctc ctg gcc aca tcc tac cca aca tca agc tct gac acc<br>Gln Lys Leu Leu Leu Ala Thr Ser Tyr Pro Thr Ser Ser Ser Asp Thr<br>145             150             155             160 | | 480 |
| cag aag gaa ggg acc gcc tgg cgc cag gca ggc ctc aga tct aaa agt<br>Gln Lys Glu Gly Thr Ala Trp Arg Gln Ala Gly Leu Arg Ser Lys Ser<br>              165             170             175 | | 528 |
| caa cgg cct tgt gtt aag gcg gac agc acc caa gac aag aag gct ccc<br>Gln Arg Pro Cys Val Lys Ala Asp Ser Thr Gln Asp Lys Lys Ala Pro<br>              180             185             190 | | 576 |
| atg atg cag tct cag agc cga agt tgt aca gaa cta cat aag cac ctc<br>Met Met Gln Ser Gln Ser Arg Ser Cys Thr Glu Leu His Lys His Leu<br>              195             200             205 | | 624 |
| acc tcg gca cag tgc tgc ctg cag gat cgg ggt ctg cag cca cca tgc<br>Thr Ser Ala Gln Cys Cys Leu Gln Asp Arg Gly Leu Gln Pro Pro Cys<br>210             215             220 | | 672 |
| ctc cag agt ccc cgg ctc cct gcc aag gag gac aag gag ccg ggt gag<br>Leu Gln Ser Pro Arg Leu Pro Ala Lys Glu Asp Lys Glu Pro Gly Glu<br>225             230             235             240 | | 720 |
| gac tgc ccg agc ccc cag cca gct cca gcc tct ccc cgg gac tcc cta<br>Asp Cys Pro Ser Pro Gln Pro Ala Pro Ala Ser Pro Arg Asp Ser Leu<br>              245             250             255 | | 768 |
| gct ctg ggc agg gca gac ccc ggt gcc ccg gtt tcc cag gaa gac atg<br>Ala Leu Gly Arg Ala Asp Pro Gly Ala Pro Val Ser Gln Glu Asp Met<br>              260             265             270 | | 816 |
| cag gcg atg gtg caa ctc ata cgc tac atg cac acc tac tgc ctc ccc<br>Gln Ala Met Val Gln Leu Ile Arg Tyr Met His Thr Tyr Cys Leu Pro<br>275             280             285 | | 864 |
| cag agg aag ctg ccc cca cag acc cct gag cca ctc ccc aag gcc tgc<br>Gln Arg Lys Leu Pro Pro Gln Thr Pro Glu Pro Leu Pro Lys Ala Cys<br>290             295             300 | | 912 |
| agc aac ccc tcc cag cag gtc aga tcc cgg ccc tgg tcc cgg cac cac<br>Ser Asn Pro Ser Gln Gln Val Arg Ser Arg Pro Trp Ser Arg His His<br>305             310             315             320 | | 960 |
| tcc aaa gcc tcc tgg gct gag ttc tcc att ctg agg gaa ctt ctg gct<br>Ser Lys Ala Ser Trp Ala Glu Phe Ser Ile Leu Arg Glu Leu Leu Ala<br>              325             330             335 | | 1008 |
| caa gac gtg ctc tgt gat gtc agc aaa ccc tac cgt ctg gcc acg cct<br>Gln Asp Val Leu Cys Asp Val Ser Lys Pro Tyr Arg Leu Ala Thr Pro<br>              340             345             350 | | 1056 |
| gtt tat gcc tcc ctc aca cct cgg tca agg ccc agg ccc ccc aaa gac<br>Val Tyr Ala Ser Leu Thr Pro Arg Ser Arg Pro Arg Pro Pro Lys Asp | | 1104 |

-continued

```
                355                 360                 365
agt cag gcc tcc cct ggt cgc cca tcc tcg gtg gag gag gta agg atc      1152
Ser Gln Ala Ser Pro Gly Arg Pro Ser Ser Val Glu Glu Val Arg Ile
        370                 375                 380 gca gct tca ccc aag agc acc ggg ccc aga cca agc ctg cgc cca ctg      1200
Ala Ala Ser Pro Lys Ser Thr Gly Pro Arg Pro Ser Leu Arg Pro Leu
385                 390                 395                 400 cgg ctg gag gtg aaa agg gag gtc cgc cgg cct gcc aga ctg cag cag      1248
Arg Leu Glu Val Lys Arg Glu Val Arg Arg Pro Ala Arg Leu Gln Gln
        405                 410                 415 cag gag gag gaa gac gag gaa gaa gag gag gaa gag gaa gaa gaa          1296
Gln Glu Glu Glu Asp Glu Glu Glu Glu Glu Glu Glu Glu Glu Glu
            420                 425                 430 aaa gag gag gag gag gag tgg ggc agg aaa agg cca ggc cga ggc ctg      1344
Lys Glu Glu Glu Glu Glu Trp Gly Arg Lys Arg Pro Gly Arg Gly Leu
        435                 440                 445 cca tgg acg aag ctg ggg agg aag ctg gag agc tct gtg tgc ccc gtg      1392
Pro Trp Thr Lys Leu Gly Arg Lys Leu Glu Ser Ser Val Cys Pro Val
450                 455                 460 cgg cgt tct cgg aga ctg aac cct gag ctg ggc ccc tgg ctg aca ttt      1440
Arg Arg Ser Arg Arg Leu Asn Pro Glu Leu Gly Pro Trp Leu Thr Phe
465                 470                 475                 480 gca gat gag ccg ctg gtc ccc tcg gag ccc caa ggt gct ctg ccc tca      1488
Ala Asp Glu Pro Leu Val Pro Ser Glu Pro Gln Gly Ala Leu Pro Ser
                485                 490                 495 ctg tgc ctg gct ccc aag gcc tac gac gta gag cgg gag ctg ggc agc      1536
Leu Cys Leu Ala Pro Lys Ala Tyr Asp Val Glu Arg Glu Leu Gly Ser
        500                 505                 510 ccc acg gac gag gac agt ggc caa gac cag cag ctc cta cgg gga ccc      1584
Pro Thr Asp Glu Asp Ser Gly Gln Asp Gln Gln Leu Leu Arg Gly Pro
            515                 520                 525 cag atc cct gcc ctg gag agc ccc tgt gag agt ggc gac cca act ttt      1632
Gln Ile Pro Ala Leu Glu Ser Pro Cys Glu Ser Gly Asp Pro Thr Phe
        530                 535                 540 ggc aag aag agc ttt gag cag acc ttg aca gtg gag ctc tgt ggc aca      1680
Gly Lys Lys Ser Phe Glu Gln Thr Leu Thr Val Glu Leu Cys Gly Thr
545                 550                 555                 560 gca ggt gag cca ggg ggc ttc cac tgg cag gtg cct tca gga aaa cac      1728
Ala Gly Glu Pro Gly Gly Phe His Trp Gln Val Pro Ser Gly Lys His
                565                 570                 575 ccg tgc atc tct gag ttt ttc atc atg cat ggg caa gga ctc acc cca      1776
Pro Cys Ile Ser Glu Phe Phe Ile Met His Gly Gln Gly Leu Thr Pro
                580                 585                 590 ccc acc aca cca ccg tac aag ccc aca gag gag gat ccc ttc aaa cca      1824
Pro Thr Thr Pro Pro Tyr Lys Pro Thr Glu Glu Asp Pro Phe Lys Pro
        595                 600                 605 gac atc aag cat agt cta ggc aaa gaa ata gct ctc agc ctc ccc tcc      1872
Asp Ile Lys His Ser Leu Gly Lys Glu Ile Ala Leu Ser Leu Pro Ser
610                 615                 620 cct gag ggc ctc tca ctc aag gcc acc cca ggg gct gcc cac aag ctg      1920
Pro Glu Gly Leu Ser Leu Lys Ala Thr Pro Gly Ala Ala His Lys Leu
625                 630                 635                 640 cca aag aag cac cca gag cga agt gag ctc ctg tcc cac ctg cga cat      1968
Pro Lys Lys His Pro Glu Arg Ser Glu Leu Leu Ser His Leu Arg His
                645                 650                 655 gcc aca gcc cag cca gcc tcc cag gct ggc cag aag cgt ccc ttc tcc      2016
Ala Thr Ala Gln Pro Ala Ser Gln Ala Gly Gln Lys Arg Pro Phe Ser
        660                 665                 670 tgt tcc ttt gga gac cat gac tac tgc cag gtg ctc cga cca gaa ggc      2064
```

```
                Cys Ser Phe Gly Asp His Asp Tyr Cys Gln Val Leu Arg Pro Glu Gly
                        675                 680                 685 gtc ctg caa agg aag gtg ctg agg tcc tgg gag ccg tct ggg gtt cac              2112
Val Leu Gln Arg Lys Val Leu Arg Ser Trp Glu Pro Ser Gly Val His
690                 695                 700 ctt gag gac tgg ccc cag cag ggt gcc cct tgg gct gag gca cag gcc              2160
Leu Glu Asp Trp Pro Gln Gln Gly Ala Pro Trp Ala Glu Ala Gln Ala
705                 710                 715                 720 cct ggc agg gag gaa gac aga agc tgt gat gct ggc gcc cca ccc aag              2208
Pro Gly Arg Glu Glu Asp Arg Ser Cys Asp Ala Gly Ala Pro Pro Lys
                725                 730                 735 gac agc acg ctg ctg aga gac cat gag atc cgt gcc agc ctc acc aaa              2256
Asp Ser Thr Leu Leu Arg Asp His Glu Ile Arg Ala Ser Leu Thr Lys
            740                 745                 750 cac ttt ggg ctg ctg gag acc gcc ctg gag gag gaa gac ctg gcc tcc              2304
His Phe Gly Leu Leu Glu Thr Ala Leu Glu Glu Glu Asp Leu Ala Ser
        755                 760                 765 tgc aag agc cct gag tat gac act gtc ttt gaa gac agc agc agc agc              2352
Cys Lys Ser Pro Glu Tyr Asp Thr Val Phe Glu Asp Ser Ser Ser Ser
    770                 775                 780 agc ggc gag agc agc ttc ctc cca gag gag gaa gag gaa ggg gag              2400
Ser Gly Glu Ser Ser Phe Leu Pro Glu Glu Glu Glu Glu Gly Glu
785                 790                 795                 800 gag gag gag gag gac gat gaa gaa gag gac tca ggg gtc agc ccc act              2448
Glu Glu Glu Glu Asp Asp Glu Glu Glu Asp Ser Gly Val Ser Pro Thr
                805                 810                 815 tgc tct gac cac tgc ccc tac cag agc cca cca agc aag gcc aac cgg              2496
Cys Ser Asp His Cys Pro Tyr Gln Ser Pro Pro Ser Lys Ala Asn Arg
            820                 825                 830 cag ctc tgt tcc cgc agc cgc tca agc tct ggc tct tca ccc tgc cac              2544
Gln Leu Cys Ser Arg Ser Arg Ser Ser Ser Gly Ser Ser Pro Cys His
        835                 840                 845 tcc tgg tca cca gcc act cga agg aac ttc aga tgt gag agc aga ggg              2592
Ser Trp Ser Pro Ala Thr Arg Arg Asn Phe Arg Cys Glu Ser Arg Gly
    850                 855                 860 ccg tgt tca gac aga acg cca agc atc cgg cac gcc agg aag cgg cgg              2640
Pro Cys Ser Asp Arg Thr Pro Ser Ile Arg His Ala Arg Lys Arg Arg
865                 870                 875                 880 gaa aag gcc att ggg gaa ggc cgc gtg gtg tac att caa aat ctc tcc              2688
Glu Lys Ala Ile Gly Glu Gly Arg Val Val Tyr Ile Gln Asn Leu Ser
                885                 890                 895 agc gac atg agc tcc cga gag ctg aag agg cgc ttt gaa gtg ttt ggt              2736
Ser Asp Met Ser Ser Arg Glu Leu Lys Arg Arg Phe Glu Val Phe Gly
            900                 905                 910 gag att gag gag tgc gag gtg ctg aca aga aat agg aga ggc gag aag              2784
Glu Ile Glu Glu Cys Glu Val Leu Thr Arg Asn Arg Arg Gly Glu Lys
        915                 920                 925 tac ggc ttc atc acc tac cgg tgt tct gag cac gcg gcc ctc tct ttg              2832
Tyr Gly Phe Ile Thr Tyr Arg Cys Ser Glu His Ala Ala Leu Ser Leu
    930                 935                 940 aca aag ggc gct gcc ctg agg aag cgc aac gag ccc tcc ttc cag ctg              2880
Thr Lys Gly Ala Ala Leu Arg Lys Arg Asn Glu Pro Ser Phe Gln Leu
945                 950                 955                 960 agc tac gga ggg ctc cgg cac ttc tgc tgg ccc aga tac act gac tac              2928
Ser Tyr Gly Gly Leu Arg His Phe Cys Trp Pro Arg Tyr Thr Asp Tyr
                965                 970                 975 gat tcc aat tca gaa gag gcc ctt cct gcg tca ggg aaa agc aag tat              2976
Asp Ser Asn Ser Glu Glu Ala Leu Pro Ala Ser Gly Lys Ser Lys Tyr
            980                 985                 990
```

```
gaa gcc atg gat ttt gac agc tta ctg aaa gag gcc cag cag agc ctg    3024
Glu Ala Met Asp Phe Asp Ser Leu Leu Lys Glu Ala Gln Gln Ser Leu
            995                 1000                1005 cat tga                                                            3030
His *
```

<210> SEQ ID NO 5
<211> LENGTH: 1009
<212> TYPE: PRT
<213> ORGANISM: Homo sapiens

<400> SEQUENCE: 5

```
Met Pro Pro Val Tyr Ala Ser Glu Tyr Val Leu Pro Leu Gln Gly Gly
 1               5                  10                  15

Gly Ser Gly Glu Glu Gln Leu Tyr Ala Asp Phe Pro Glu Leu Asp Leu
            20                  25                  30

Ser Gln Leu Asp Ala Ser Asp Phe Asp Ser Ala Thr Cys Phe Gly Glu
        35                  40                  45

Leu Gln Trp Cys Pro Glu Asn Ser Glu Thr Glu Pro Asn Gln Tyr Ser
    50                  55                  60

Pro Asp Asp Ser Glu Leu Phe Gln Ile Asp Ser Glu Asn Glu Ala Leu
65                  70                  75                  80

Leu Ala Glu Leu Thr Lys Thr Leu Asp Asp Ile Pro Glu Asp Asp Val
                85                  90                  95

Gly Leu Ala Ala Phe Pro Ala Leu Asp Gly Gly Asp Ala Leu Ser Cys
            100                 105                 110

Thr Ser Ala Ser Pro Ala Pro Ser Ser Ala Pro Pro Ser Pro Ala Pro
        115                 120                 125

Glu Lys Pro Ser Ala Pro Ala Pro Glu Val Asp Glu Leu Ser Leu Leu
    130                 135                 140

Gln Lys Leu Leu Leu Ala Thr Ser Tyr Pro Thr Ser Ser Ser Asp Thr
145                 150                 155                 160

Gln Lys Glu Gly Thr Ala Trp Arg Gln Ala Gly Leu Arg Ser Lys Ser
                165                 170                 175

Gln Arg Pro Cys Val Lys Ala Asp Ser Thr Gln Asp Lys Lys Ala Pro
            180                 185                 190

Met Met Gln Ser Gln Ser Arg Ser Cys Thr Glu Leu His Lys His Leu
        195                 200                 205

Thr Ser Ala Gln Cys Cys Leu Gln Asp Arg Gly Leu Gln Pro Pro Cys
    210                 215                 220

Leu Gln Ser Pro Arg Leu Pro Ala Lys Glu Asp Lys Glu Pro Gly Glu
225                 230                 235                 240

Asp Cys Pro Ser Pro Gln Pro Ala Pro Ser Pro Arg Asp Ser Leu
                245                 250                 255

Ala Leu Gly Arg Ala Asp Pro Gly Ala Pro Val Ser Gln Glu Asp Met
            260                 265                 270

Gln Ala Met Val Gln Leu Ile Arg Tyr Met His Thr Tyr Cys Leu Pro
        275                 280                 285

Gln Arg Lys Leu Pro Pro Gln Thr Pro Glu Pro Pro Lys Ala Cys
    290                 295                 300

Ser Asn Pro Ser Gln Gln Val Arg Ser Arg Pro Trp Ser Arg His His
305                 310                 315                 320

Ser Lys Ala Ser Trp Ala Glu Phe Ser Ile Leu Arg Glu Leu Leu Ala
                325                 330                 335

Gln Asp Val Leu Cys Asp Val Ser Lys Pro Tyr Arg Leu Ala Thr Pro
```

-continued

```
               340                 345                 350
Val Tyr Ala Ser Leu Thr Pro Arg Ser Arg Pro Arg Pro Pro Lys Asp
            355                 360                 365

Ser Gln Ala Ser Pro Gly Arg Pro Ser Ser Val Glu Glu Val Arg Ile
    370                 375                 380

Ala Ala Ser Pro Lys Ser Thr Gly Pro Arg Pro Ser Leu Arg Pro Leu
385                 390                 395                 400

Arg Leu Glu Val Lys Arg Glu Val Arg Arg Pro Ala Arg Leu Gln Gln
                405                 410                 415

Gln Glu Glu Glu Asp Glu Glu Glu Glu Glu Glu Glu Glu Glu Glu Glu
            420                 425                 430

Lys Glu Glu Glu Glu Trp Gly Arg Lys Arg Pro Gly Arg Gly Leu
            435                 440                 445

Pro Trp Thr Lys Leu Gly Arg Lys Leu Glu Ser Ser Val Cys Pro Val
            450                 455                 460

Arg Arg Ser Arg Arg Leu Asn Pro Glu Leu Gly Pro Trp Leu Thr Phe
465                 470                 475                 480

Ala Asp Glu Pro Leu Val Pro Ser Glu Pro Gln Gly Ala Leu Pro Ser
                485                 490                 495

Leu Cys Leu Ala Pro Lys Ala Tyr Asp Val Glu Arg Glu Leu Gly Ser
                500                 505                 510

Pro Thr Asp Glu Asp Ser Gly Gln Asp Gln Leu Leu Arg Gly Pro
            515                 520                 525

Gln Ile Pro Ala Leu Glu Ser Pro Cys Glu Ser Gly Asp Pro Thr Phe
            530                 535                 540

Gly Lys Lys Ser Phe Glu Gln Thr Leu Thr Val Glu Leu Cys Gly Thr
545                 550                 555                 560

Ala Gly Glu Pro Gly Gly Phe His Trp Gln Val Pro Ser Gly Lys His
                565                 570                 575

Pro Cys Ile Ser Glu Phe Phe Ile Met His Gly Gln Gly Leu Thr Pro
                580                 585                 590

Pro Thr Thr Pro Pro Tyr Lys Pro Thr Glu Glu Asp Pro Phe Lys Pro
            595                 600                 605

Asp Ile Lys His Ser Leu Gly Lys Glu Ile Ala Leu Ser Leu Pro Ser
    610                 615                 620

Pro Glu Gly Leu Ser Leu Lys Ala Thr Pro Gly Ala Ala His Lys Leu
625                 630                 635                 640

Pro Lys Lys His Pro Glu Arg Ser Glu Leu Leu Ser His Leu Arg His
                645                 650                 655

Ala Thr Ala Gln Pro Ala Ser Gln Ala Gly Gln Lys Arg Pro Phe Ser
            660                 665                 670

Cys Ser Phe Gly Asp His Asp Tyr Cys Gln Val Leu Arg Pro Glu Gly
            675                 680                 685

Val Leu Gln Arg Lys Val Leu Arg Ser Trp Glu Pro Ser Gly Val His
            690                 695                 700

Leu Glu Asp Trp Pro Gln Gln Gly Ala Pro Trp Ala Glu Ala Gln Ala
705                 710                 715                 720

Pro Gly Arg Glu Glu Asp Arg Ser Cys Asp Ala Gly Ala Pro Pro Lys
                725                 730                 735

Asp Ser Thr Leu Leu Arg Asp His Glu Ile Arg Ala Ser Leu Thr Lys
            740                 745                 750

His Phe Gly Leu Leu Glu Thr Ala Leu Glu Glu Glu Asp Leu Ala Ser
            755                 760                 765
```

```
Cys Lys Ser Pro Glu Tyr Asp Thr Val Phe Glu Asp Ser Ser Ser
    770                 775                 780

Ser Gly Glu Ser Ser Phe Leu Pro Glu Glu Glu Glu Glu Gly Glu
785                 790                 795                 800

Glu Glu Glu Glu Asp Asp Glu Glu Asp Ser Gly Val Ser Pro Thr
                805                 810                 815

Cys Ser Asp His Cys Pro Tyr Gln Ser Pro Ser Lys Ala Asn Arg
            820                 825                 830

Gln Leu Cys Ser Arg Ser Arg Ser Ser Gly Ser Ser Pro Cys His
        835                 840                 845

Ser Trp Ser Pro Ala Thr Arg Arg Asn Phe Arg Cys Glu Ser Arg Gly
    850                 855                 860

Pro Cys Ser Asp Arg Thr Pro Ser Ile Arg His Ala Arg Lys Arg Arg
865                 870                 875                 880

Glu Lys Ala Ile Gly Glu Gly Arg Val Val Tyr Ile Gln Asn Leu Ser
                885                 890                 895

Ser Asp Met Ser Ser Arg Glu Leu Lys Arg Arg Phe Glu Val Phe Gly
            900                 905                 910

Glu Ile Glu Glu Cys Glu Val Leu Thr Arg Asn Arg Arg Gly Glu Lys
        915                 920                 925

Tyr Gly Phe Ile Thr Tyr Arg Cys Ser Glu His Ala Ala Leu Ser Leu
    930                 935                 940

Thr Lys Gly Ala Ala Leu Arg Lys Arg Asn Glu Pro Ser Phe Gln Leu
945                 950                 955                 960

Ser Tyr Gly Gly Leu Arg His Phe Cys Trp Pro Arg Tyr Thr Asp Tyr
                965                 970                 975

Asp Ser Asn Ser Glu Glu Ala Leu Pro Ala Ser Gly Lys Ser Lys Tyr
            980                 985                 990

Glu Ala Met Asp Phe Asp Ser Leu Leu Lys Glu Ala Gln Gln Ser Leu
        995                 1000                1005

His
```

```
<210> SEQ ID NO 6
<211> LENGTH: 3027
<212> TYPE: DNA
<213> ORGANISM: Homo sapiens
<220> FEATURE:
<221> NAME/KEY: CDS
<222> LOCATION: (1)...(3027)

<400> SEQUENCE: 6
```

```
atg cct cct gtg tat gcc tct gag tat gtc ttg cca ctc cag ggt gga      48
Met Pro Pro Val Tyr Ala Ser Glu Tyr Val Leu Pro Leu Gln Gly Gly
 1               5                  10                  15 ggg tcc ggg gag gag caa ctc tat gct gac ttt cca gaa ctc gac ctc      96
Gly Ser Gly Glu Glu Gln Leu Tyr Ala Asp Phe Pro Glu Leu Asp Leu
             20                  25                  30 tcc cag ctg gat gcc agc gac ttt gac tcg gcc acc tgc ttt ggg gag     144
Ser Gln Leu Asp Ala Ser Asp Phe Asp Ser Ala Thr Cys Phe Gly Glu
         35                  40                  45 ctg cag tgg tgc cca gag aac tca gag act gaa ccc aac cag tac agc     192
Leu Gln Trp Cys Pro Glu Asn Ser Glu Thr Glu Pro Asn Gln Tyr Ser
     50                  55                  60 ccc gat gac tcc gag ctc ttc cag att gac agt gag aat gag gcc ctc     240
Pro Asp Asp Ser Glu Leu Phe Gln Ile Asp Ser Glu Asn Glu Ala Leu
 65                  70                  75                  80
```

-continued

```
ctg gca gag ctc acc aag acc ctg gat gac atc cct gaa gat gac gtg      288
Leu Ala Glu Leu Thr Lys Thr Leu Asp Asp Ile Pro Glu Asp Asp Val
             85                  90                  95 ggt ctg gct gcc ttc cca gcc ctg gat ggt gga gac gct cta tca tgc      336
Gly Leu Ala Ala Phe Pro Ala Leu Asp Gly Gly Asp Ala Leu Ser Cys
            100                 105                 110 acc tca gct tcg cct gcc ccc tca tct gca ccc ccc agc cct gcc ccg      384
Thr Ser Ala Ser Pro Ala Pro Ser Ser Ala Pro Pro Ser Pro Ala Pro
        115                 120                 125 gag aag ccc tcg gcc cca gcc cct gag gtg gac gag ctc tca ctg ctg      432
Glu Lys Pro Ser Ala Pro Ala Pro Glu Val Asp Glu Leu Ser Leu Leu
    130                 135                 140 cag aag ctc ctc ctg gcc aca tcc tac cca aca tca agc tct gac acc      480
Gln Lys Leu Leu Leu Ala Thr Ser Tyr Pro Thr Ser Ser Ser Asp Thr
145                 150                 155                 160 cag aag gaa ggg acc gcc tgg cgc cag gca ggc ctc aga tct aaa agt      528
Gln Lys Glu Gly Thr Ala Trp Arg Gln Ala Gly Leu Arg Ser Lys Ser
                165                 170                 175 caa cgg cct tgt gtt aag gcg gac agc acc caa gac aag aag gct ccc      576
Gln Arg Pro Cys Val Lys Ala Asp Ser Thr Gln Asp Lys Lys Ala Pro
            180                 185                 190 atg atg cag tct cag agc cga agt tgt aca gaa cta cat aag cac ctc      624
Met Met Gln Ser Gln Ser Arg Ser Cys Thr Glu Leu His Lys His Leu
        195                 200                 205 acc tcg gca cag tgc tgc ctg cag gat cgg ggt ctg cag cca cca tgc      672
Thr Ser Ala Gln Cys Cys Leu Gln Asp Arg Gly Leu Gln Pro Pro Cys
    210                 215                 220 ctc cag agt ccc cgg ctc cct gcc aag gag gac aag gag ccg ggt gag      720
Leu Gln Ser Pro Arg Leu Pro Ala Lys Glu Asp Lys Glu Pro Gly Glu
225                 230                 235                 240 gac tgc ccg agc ccc cag cca gct cca gcc tct ccc cgg gac tcc cta      768
Asp Cys Pro Ser Pro Gln Pro Ala Pro Ala Ser Pro Arg Asp Ser Leu
                245                 250                 255 gct ctg ggc agg gca gac ccc ggt gcc ccg gtt tcc cag gaa gac atg      816
Ala Leu Gly Arg Ala Asp Pro Gly Ala Pro Val Ser Gln Glu Asp Met
            260                 265                 270 cag gcg atg gtg caa ctc ata cgc tac atg cac acc tac tgc ctc ccc      864
Gln Ala Met Val Gln Leu Ile Arg Tyr Met His Thr Tyr Cys Leu Pro
        275                 280                 285 cag agg aag ctg ccc cca cag acc cct gag cca ctc ccc aag gcc tgc      912
Gln Arg Lys Leu Pro Pro Gln Thr Pro Glu Pro Leu Pro Lys Ala Cys
    290                 295                 300 agc aac ccc tcc cag cag gtc aga tcc ggc ccc tgg tcc cgg cac cac      960
Ser Asn Pro Ser Gln Gln Val Arg Ser Arg Pro Trp Ser Arg His His
305                 310                 315                 320 tcc aaa gcc tcc tgg gct gag ttc tcc att ctg agg gaa ctt ctg gct     1008
Ser Lys Ala Ser Trp Ala Glu Phe Ser Ile Leu Arg Glu Leu Leu Ala
                325                 330                 335 caa gac gtg ctc tgt gat gtc agc aaa ccc tac cgt ctg gcc acg cct     1056
Gln Asp Val Leu Cys Asp Val Ser Lys Pro Tyr Arg Leu Ala Thr Pro
            340                 345                 350 gtt tat gcc tcc ctc aca cct cgg tca agg ccc agg ccc ccc aaa gac     1104
Val Tyr Ala Ser Leu Thr Pro Arg Ser Arg Pro Arg Pro Pro Lys Asp
        355                 360                 365 agt cag gcc tcc cct ggt cgc cca tcc tcg gtg gag gag gta agg atc     1152
Ser Gln Ala Ser Pro Gly Arg Pro Ser Ser Val Glu Glu Val Arg Ile
    370                 375                 380 gca gct tca ccc aag agc acc ggg ccc aga cca agc ctg cgc cca ctg     1200
Ala Ala Ser Pro Lys Ser Thr Gly Pro Arg Pro Ser Leu Arg Pro Leu
385                 390                 395                 400
```

-continued

| | |
|---|---|
| cgg ctg gag gtg aaa agg gag gtc cgc cgg cct gcc aga ctg cag cag<br>Arg Leu Glu Val Lys Arg Glu Val Arg Arg Pro Ala Arg Leu Gln Gln<br>405       410       415 | 1248 |
| cag gag gag gaa gac gag gaa gaa gag gag gaa gag gaa gaa gaa<br>Gln Glu Glu Glu Asp Glu Glu Glu Glu Glu Glu Glu Glu Glu<br>  420       425       430 | 1296 |
| aaa gag gag gag gag gag tgg ggc agg aaa agg cca ggc cga ggc ctg<br>Lys Glu Glu Glu Glu Glu Trp Gly Arg Lys Arg Pro Gly Arg Gly Leu<br>435       440       445 | 1344 |
| cca tgg acg aag ctg ggg agg aag ctg gag agc tct gtg tgc ccc gtg<br>Pro Trp Thr Lys Leu Gly Arg Lys Leu Glu Ser Ser Val Cys Pro Val<br>450       455       460 | 1392 |
| cgg cgt tct cgg aga ctg aac cct gag ctg ggc ccc tgg ctg aca ttt<br>Arg Arg Ser Arg Arg Leu Asn Pro Glu Leu Gly Pro Trp Leu Thr Phe<br>465       470       475       480 | 1440 |
| gca gat gag ccg ctg gtc ccc tcg gag ccc caa ggt gct ctg ccc tca<br>Ala Asp Glu Pro Leu Val Pro Ser Glu Pro Gln Gly Ala Leu Pro Ser<br>      485       490       495 | 1488 |
| ctg tgc ctg gct ccc aag gcc tac gac gta gag cgg gag ctg ggc agc<br>Leu Cys Leu Ala Pro Lys Ala Tyr Asp Val Glu Arg Glu Leu Gly Ser<br>    500       505       510 | 1536 |
| ccc acg gac gag gac agt ggc caa gac cag cag ctc cta cgg gga ccc<br>Pro Thr Asp Glu Asp Ser Gly Gln Asp Gln Gln Leu Leu Arg Gly Pro<br>      515       520       525 | 1584 |
| cag atc cct gcc ctg gag agc ccc tgt gag agt ggc gac cca act ttt<br>Gln Ile Pro Ala Leu Glu Ser Pro Cys Glu Ser Gly Asp Pro Thr Phe<br>530       535       540 | 1632 |
| ggc aag aag agc ttt gag cag acc ttg aca gtg gag ctc tgt ggc aca<br>Gly Lys Lys Ser Phe Glu Gln Thr Leu Thr Val Glu Leu Cys Gly Thr<br>545       550       555       560 | 1680 |
| gca ggt gag cca ggg ggc ttc cac tgg cag gtg cct tca gga aaa cac<br>Ala Gly Glu Pro Gly Gly Phe His Trp Gln Val Pro Ser Gly Lys His<br>      565       570       575 | 1728 |
| ccg tgc atc tct gag ttt ttc atc atg cat ggg caa gga ctc acc cca<br>Pro Cys Ile Ser Glu Phe Phe Ile Met His Gly Gln Gly Leu Thr Pro<br>    580       585       590 | 1776 |
| ccc acc aca cca ccg tac aag ccc aca gag gag gat ccc ttc aaa cca<br>Pro Thr Thr Pro Pro Tyr Lys Pro Thr Glu Glu Asp Pro Phe Lys Pro<br>      595       600       605 | 1824 |
| gac atc aag cat agt cta ggc aaa gaa ata gct ctc agc ctc ccc tcc<br>Asp Ile Lys His Ser Leu Gly Lys Glu Ile Ala Leu Ser Leu Pro Ser<br>610       615       620 | 1872 |
| cct gag ggc ctc tca ctc aag gcc acc cca ggg gct gcc cac aag ctg<br>Pro Glu Gly Leu Ser Leu Lys Ala Thr Pro Gly Ala Ala His Lys Leu<br>625       630       635       640 | 1920 |
| cca aag aag cac cca gag cga agt gag ctc ctg tcc cac ctg cga cat<br>Pro Lys Lys His Pro Glu Arg Ser Glu Leu Leu Ser His Leu Arg His<br>      645       650       655 | 1968 |
| gcc aca gcc cag cca gcc tcc cag gct ggc cag aag cgt ccc ttc tcc<br>Ala Thr Ala Gln Pro Ala Ser Gln Ala Gly Gln Lys Arg Pro Phe Ser<br>    660       665       670 | 2016 |
| tgt tcc ttt gga gac cat gac tac tgc cag gtg ctc cga cca gaa ggc<br>Cys Ser Phe Gly Asp His Asp Tyr Cys Gln Val Leu Arg Pro Glu Gly<br>      675       680       685 | 2064 |
| gtc ctg caa agg aag gtg ctg agg tcc tgg gag ccg tct ggg gtt cac<br>Val Leu Gln Arg Lys Val Leu Arg Ser Trp Glu Pro Ser Gly Val His<br>690       695       700 | 2112 |
| ctt gag gac tgg ccc cag cag ggt gcc cct tgg gct gag gca cag gcc<br>Leu Glu Asp Trp Pro Gln Gln Gly Ala Pro Trp Ala Glu Ala Gln Ala | 2160 |

-continued

| | | |
|---|---|---|
| cct ggc agg gag gaa gac aga agc tgt gat gct ggc gcc cca ccc aag<br>Pro Gly Arg Glu Glu Asp Arg Ser Cys Asp Ala Gly Ala Pro Pro Lys<br>725                                    730                           735 | 2208 |
| gac agc acg ctg ctg aga gac cat gag atc cgt gcc agc ctc acc aaa<br>Asp Ser Thr Leu Leu Arg Asp His Glu Ile Arg Ala Ser Leu Thr Lys<br>     740                       745                       750 | 2256 |
| cac ttt ggg ctg ctg gag acc gcc ctg gag gag gaa gac ctg gcc tcc<br>His Phe Gly Leu Leu Glu Thr Ala Leu Glu Glu Glu Asp Leu Ala Ser<br>755                          760                       765 | 2304 |
| tgc aag agc cct gag tat gac act gtc ttt gaa gac agc agc agc agc<br>Cys Lys Ser Pro Glu Tyr Asp Thr Val Phe Glu Asp Ser Ser Ser Ser<br>     770                       775                       780 | 2352 |
| agc ggc gag agc agc ttc ctc cca gag gag gaa gag gaa ggg gag<br>Ser Gly Glu Ser Ser Phe Leu Pro Glu Glu Glu Glu Glu Gly Glu<br>785                      790                      795                 800 | 2400 |
| gag gag gag gag gac gat gaa gaa gag gac tca ggg gtc agc ccc act<br>Glu Glu Glu Glu Asp Asp Glu Glu Glu Asp Ser Gly Val Ser Pro Thr<br>                       805                       810                       815 | 2448 |
| tgc tct gac cac tgc ccc tac cag agc cca cca agc aag gcc aac cgg<br>Cys Ser Asp His Cys Pro Tyr Gln Ser Pro Pro Ser Lys Ala Asn Arg<br>820                          825                       830 | 2496 |
| cag ctc tgt tcc cgc agc cgc tca agc tct ggc tct tca ccc tgc cac<br>Gln Leu Cys Ser Arg Ser Arg Ser Ser Ser Gly Ser Ser Pro Cys His<br>     835                       840                       845 | 2544 |
| tcc tgg tca cca gcc act cga agg aac ttc aga tgt gag agc aga ggg<br>Ser Trp Ser Pro Ala Thr Arg Arg Asn Phe Arg Cys Glu Ser Arg Gly<br>850                          855                       860 | 2592 |
| ccg tgt tca gac aga acg cca agc atc cgg cac gcc agg aag cgg cgg<br>Pro Cys Ser Asp Arg Thr Pro Ser Ile Arg His Ala Arg Lys Arg Arg<br>865                          870                       875                 880 | 2640 |
| gaa aag gcc att ggg gaa ggc cgc gtg gtg tac att caa aat ctc tcc<br>Glu Lys Ala Ile Gly Glu Gly Arg Val Val Tyr Ile Gln Asn Leu Ser<br>                       885                       890                       895 | 2688 |
| agc gac atg agc tcc cga gag ctg aag agg cgc ttt gaa gtg ttt ggt<br>Ser Asp Met Ser Ser Arg Glu Leu Lys Arg Arg Phe Glu Val Phe Gly<br>900                          905                       910 | 2736 |
| gag att gag gag tgc gag gtg ctg aca aga aat agg aga ggc gag aag<br>Glu Ile Glu Glu Cys Glu Val Leu Thr Arg Asn Arg Arg Gly Glu Lys<br>     915                       920                       925 | 2784 |
| tac ggc ttc atc acc tac cgg tgt tct gag cac gcg gcc ctc tct ttg<br>Tyr Gly Phe Ile Thr Tyr Arg Cys Ser Glu His Ala Ala Leu Ser Leu<br>930                          935                       940 | 2832 |
| aca aag ggc gct gcc ctg agg aag cgc aac gag ccc tcc ttc cag ctg<br>Thr Lys Gly Ala Ala Leu Arg Lys Arg Asn Glu Pro Ser Phe Gln Leu<br>945                          950                       955                 960 | 2880 |
| agc tac gga ggg ctc cgg cac ttc tgc tgg ccc aga tac act gac tac<br>Ser Tyr Gly Gly Leu Arg His Phe Cys Trp Pro Arg Tyr Thr Asp Tyr<br>                       965                       970                       975 | 2928 |
| gat tcc aat tca gaa gag gcc ctt cct gcg tca ggg aaa agc aag tat<br>Asp Ser Asn Ser Glu Glu Ala Leu Pro Ala Ser Gly Lys Ser Lys Tyr<br>980                          985                       990 | 2976 |
| gaa gcc atg gat ttt gac agc tta ctg aaa gag gcc cag cag agc ctg<br>Glu Ala Met Asp Phe Asp Ser Leu Leu Lys Glu Ala Gln Gln Ser Leu<br>               995                     1000                  1005 | 3024 |
| cat<br>His | 3027 |

What is claimed:

1. An isolated polypeptide comprising an amino acid sequence which is at least 97% identical to the amino acid sequence of SEQ ID NO: 5, wherein the polypeptide modulates one or more of the following biological activities: activity of a nuclear receptor and/or nuclear respiratory factor 1 (NRF1); brown adipose cell determination and/or differentiation; mitochondrial activity and/or biogenesis; or fatty acid β-oxidation.

2. The isolated polypeptide of claim 1 comprising the amino acid sequence of SEQ ID NO: 5.

3. The polypeptide of claim 1, further comprising a heterologous amino acid sequence.

4. An isolated polypeptide which is encoded by a nucleic acid molecule comprising a nucleotide sequence which is at least 97% identical to the nucleic acid sequence of SEQ ID NO: 4 or 6, wherein the polypeptide modulates one or more of the following biological activities: activity of a nuclear receptor and/or nuclear respiratory factor 1 (NRF1); brown adipose cell determination and/or differentiation; mitochondrial activity and/or biogenesis; or fatty acid β-oxidation.

5. The isolated polypeptide of claim 4, further comprising a heterologous amino acid sequence.

* * * * *